US008147455B2

(12) United States Patent
Butts et al.

(10) Patent No.: US 8,147,455 B2
(45) Date of Patent: Apr. 3, 2012

(54) INFUSION APPARATUSES AND METHODS OF USE

(75) Inventors: David M. Butts, Riverton, UT (US); Jason R. Stats, Layton, UT (US); Bret Hamatake, Grantsville, UT (US); Sandra J. Rome, Taylorsville, UT (US); Walter H. Shang, Irvine, CA (US)

(73) Assignee: C. R. Bard, Inc., Murray Hill, NJ (US)

( * ) Notice: Subject to any disclaimer, the term of this patent is extended or adjusted under 35 U.S.C. 154(b) by 272 days.

(21) Appl. No.: 11/380,621

(22) Filed: Apr. 27, 2006

(65) Prior Publication Data
US 2006/0253076 A1 Nov. 9, 2006

Related U.S. Application Data

(60) Provisional application No. 60/675,309, filed on Apr. 27, 2005.

(51) Int. Cl.
*A61M 5/178* (2006.01)

(52) U.S. Cl. ......... 604/167.02; 604/164.01; 604/164.02; 604/167.01; 604/167.06

(58) Field of Classification Search ............... 604/93.01, 604/164.01, 164.02, 166.01, 167.01, 167.02, 604/288.01, 523, 164.07, 164.08, 165.01, 604/165.02, 167.06, 288.02, 288.04, 48, 604/500, 506, 513, 117, 164.04, 174, 177, 604/201, 256, 264, 272, 524, 533, 534, 535, 604/537, 538, 539, 890.1; 128/DIG. 26
See application file for complete search history.

(56) References Cited

U.S. PATENT DOCUMENTS

| | | | |
|---|---|---|---|
| 4,196,731 A | 4/1980 | Laurin et al. | |
| 4,569,675 A | 2/1986 | Prosl et al. | |
| 4,668,221 A | 5/1987 | Luther | |
| 4,684,365 A | 8/1987 | Reinicke | |
| 4,743,231 A | 5/1988 | Kay et al. | |
| 4,755,173 A * | 7/1988 | Konopka et al. | ......... 604/167.02 |
| 4,861,341 A | 8/1989 | Woodburn | |
| 4,915,690 A | 4/1990 | Cone et al. | |

(Continued)

FOREIGN PATENT DOCUMENTS
EP 0619101 A1 10/1994
(Continued)

OTHER PUBLICATIONS
PCT Search Report and Written Opinion mailed on Nov. 8, 2007.
(Continued)

*Primary Examiner* — Kevin C. Sirmons
*Assistant Examiner* — Shefali Patel
(74) *Attorney, Agent, or Firm* — Rutan & Tucker, LLP

(57) ABSTRACT

An exemplary infusion system for accessing an implanted device is disclosed comprising an insertion assembly, a hub comprising a sealable path configured to receive at least a portion of the insertion assembly, a flexible catheter attached to the hub and configured to receive at least a portion of the insertion assembly, and an extension tube attached to the hub. The hub may comprise a manifold element configured to provide fluid communication between the flexible catheter and the extension tube. The hub may also comprise a septum configured to seal the sealable path upon removal of the insertion assembly from the flexible catheter. The extension tube may also be configured to receive at least a portion of the insertion assembly. Exemplary methods of providing a fluid communication path to an implanted device are also disclosed.

16 Claims, 56 Drawing Sheets

U.S. PATENT DOCUMENTS

| | | |
|---|---|---|
| 5,041,098 A | 8/1991 | Loiterman et al. |
| 5,108,377 A | 4/1992 | Cone et al. |
| 5,176,653 A * | 1/1993 | Metals .................. 604/167.02 |
| 5,176,662 A * | 1/1993 | Bartholomew et al. ....... 604/513 |
| 5,545,143 A | 8/1996 | Fischell |
| 5,607,407 A | 3/1997 | Tolkoff et al. |
| 5,704,915 A | 1/1998 | Melsky et al. |
| 5,709,668 A | 1/1998 | Wacks |
| 5,733,400 A * | 3/1998 | Gore et al. ................... 156/158 |
| 5,743,891 A | 4/1998 | Tolkoff et al. |
| 5,853,394 A | 12/1998 | Tolkoff et al. |
| 5,951,522 A | 9/1999 | Rosato et al. |
| 5,968,011 A * | 10/1999 | Larsen et al. ............ 604/288.02 |
| 5,989,239 A | 11/1999 | Finch et al. |
| 5,997,524 A | 12/1999 | Burbank et al. |
| 6,007,516 A | 12/1999 | Burbank et al. |
| 6,013,058 A * | 1/2000 | Prosl et al. ............... 604/167.03 |
| 6,017,331 A * | 1/2000 | Watts et al. .................. 604/232 |
| 6,120,492 A | 9/2000 | Finch et al. |
| 6,193,684 B1 | 2/2001 | Burbank et al. |
| 6,272,370 B1 | 8/2001 | Gillies et al. |
| 6,355,021 B1* | 3/2002 | Nielsen et al. ................. 604/263 |
| 6,473,638 B2 | 10/2002 | Ferek-Petric |
| 6,475,516 B2 | 11/2002 | DiCosmo et al. |
| 6,500,155 B2 | 12/2002 | Sasso |
| 6,537,255 B1 | 3/2003 | Raines |
| 6,652,486 B2* | 11/2003 | Bialecki et al. ............... 604/110 |
| 6,676,633 B2 | 1/2004 | Smith et al. |
| 6,719,721 B1 | 4/2004 | Okazaki et al. |
| 6,808,738 B2 | 10/2004 | DiTizio et al. |
| 6,878,136 B2 | 4/2005 | Fleury et al. |
| 6,949,084 B2* | 9/2005 | Marggi et al. .................. 604/174 |
| 7,214,207 B2 | 5/2007 | Lynch et al. |
| 7,214,215 B2 | 5/2007 | Heinzerling et al. |
| D554,253 S | 10/2007 | Kornerup |
| 7,318,816 B2 | 1/2008 | Bobroff et al. |
| 7,318,818 B2 | 1/2008 | Yashiro et al. |
| 7,347,838 B2* | 3/2008 | Kulli ........................ 604/164.08 |
| 7,947,022 B2 | 5/2011 | Amin et al. |
| 7,959,615 B2 | 6/2011 | Stats et al. |
| 8,025,639 B2 | 9/2011 | Powers et al. |
| 8,029,482 B2 | 10/2011 | Maniar et al. |
| 2001/0047165 A1 | 11/2001 | Makower et al. |
| 2001/0053889 A1* | 12/2001 | Marggi et al. ............ 604/164.11 |
| 2002/0173769 A1* | 11/2002 | Gray et al. ................... 604/506 |
| 2004/0006316 A1 | 1/2004 | Patton |
| 2004/0044306 A1 | 3/2004 | Lynch et al. |
| 2004/0078000 A1 | 4/2004 | Borchard et al. |
| 2004/0086568 A1 | 5/2004 | Ditizio et al. |
| 2004/0158207 A1* | 8/2004 | Hunn et al. ............... 604/164.01 |
| 2005/0038390 A1 | 2/2005 | Fago et al. |
| 2005/0049553 A1 | 3/2005 | Triplett et al. |
| 2006/0171980 A1 | 8/2006 | Helmus et al. |
| 2006/0173410 A1* | 8/2006 | Moberg et al. ................ 604/110 |
| 2006/0241465 A1 | 10/2006 | Huennekens et al. |
| 2006/0253076 A1 | 11/2006 | Butts et al. |
| 2007/0003603 A1 | 1/2007 | Karandikar et al. |
| 2007/0016162 A1 | 1/2007 | Burbank et al. |
| 2007/0078432 A1* | 4/2007 | Halseth et al. ................ 604/500 |
| 2007/0100302 A1 | 5/2007 | Dicarlo et al. |
| 2007/0120683 A1 | 5/2007 | Flippen et al. |
| 2007/0149920 A1 | 6/2007 | Michels et al. |
| 2007/0149921 A1 | 6/2007 | Michels et al. |
| 2007/0191773 A1 | 8/2007 | Wojcik |
| 2007/0207335 A1 | 9/2007 | Karandikar et al. |
| 2007/0276355 A1* | 11/2007 | Nielsen et al. ................ 604/533 |
| 2007/0293800 A1 | 12/2007 | McMaken et al. |
| 2007/0299408 A1 | 12/2007 | Alferness et al. |
| 2008/0108949 A1 | 5/2008 | Beasley et al. |
| 2008/0137923 A1 | 6/2008 | Spahn |
| 2009/0216216 A1 | 8/2009 | Powers et al. |
| 2010/0121283 A1 | 5/2010 | Hamatake et al. |
| 2010/0268165 A1 | 10/2010 | Maniar et al. |
| 2011/0118677 A1 | 5/2011 | Wiley et al. |

FOREIGN PATENT DOCUMENTS

| | | |
|---|---|---|
| EP | 1896117 A2 | 3/2008 |
| EP | 2324878 A2 | 5/2011 |
| EP | 2324879 A2 | 5/2011 |
| JP | 62155857 A | 7/1987 |
| JP | 62281966 A | 12/1987 |
| JP | 6296633 A | 10/1994 |
| JP | 2002500076 A | 1/2002 |
| WO | 8911309 A1 | 11/1989 |
| WO | WO-9706845 | 2/1997 |
| WO | WO-9817337 | 4/1998 |
| WO | 9934859 A1 | 7/1999 |
| WO | 2006134100 A1 | 12/2006 |
| WO | 2007092210 A1 | 8/2007 |
| WO | 2007094898 A2 | 8/2007 |
| WO | 2007098771 A2 | 9/2007 |
| WO | 2008062173 A1 | 5/2008 |

OTHER PUBLICATIONS

International Search Report from related International Application No. PCT/US2006/016056, dated Sep. 20, 2006.

International Application PCT/US2010/030256 filed Apr. 7, 2010 Search Report and Written Opinion dated Jun. 4, 2010.

U.S. Appl. No. 11/320,223, filed Dec. 28, 2005 Final Office Action dated Jun. 22, 2010.

U.S. Appl. No. 11/368,954, filed Mar. 6, 2006 Notice of Allowance dated Jun. 24, 2010.

AngioDynamics, Smart Port Guidelines for Health Care Providers, 1996.

EP Application No. 06845998.1 filed Dec. 21, 2006 Supplementary Search Report dated Jul. 22, 2010.

U.S. Appl. No. 11/380,124, filed Apr. 25, 2006 Final Office Action dated Aug. 13, 2010.

U.S. Appl. No. 11/937,302, filed Nov. 8, 2007 Non-Final Office Action dated Sep. 13, 2010.

U.S. Appl. No. 12/419,957, filed Apr. 7, 2009 Non-Final Office Action dated Jul. 29, 2010.

Coyle, Douglas et al, Power Injection of Contrast Media via Peripherally Inserted Central Catheters for CT, J Vasc Interv Radiol, pp. 809-814, vol. 15, 2004.

EP 06751411 filed Apr. 25, 2006 Office Action dated Aug. 10, 2009.

EP 06751411 filed Apr. 25, 2006 Office Action dated Sep. 2, 2008.

EP 06845998 filed Dec. 21, 2006 Office Action dated Mar. 10, 2011.

JP 2007-558331 filed Mar. 6, 2006 Office Action dated May 17, 2011.

JP 2008-509056 filed Apr. 25, 2006 Office Action dated Jun. 7, 2011.

L-CATH® For Ports, Luther Medical Products, Inc., Tustin, California, 2 pages, 1994.

PCT/US2006/049007 filed Dec. 21, 2006 Written Opinion dated Oct. 1, 2007.

PCT/US2009/062854 filed Oct. 30, 2009 International Preliminary Report on Patentability dated May 5, 2011.

PCT/US2010/030256 filed Apr. 7, 2010 Written Opinion dated Jun. 4, 2010.

PCT/US2010/054994 filed Nov. 1, 2010 Search Report dated Jan. 10, 2011.

PCT/US2010/054994 filed Nov. 1, 2010 Written Opinion dated Jan. 10, 2011.

U.S. Appl. No. 11/320,223, filed Dec. 28, 2005 Final Office Action dated Aug. 3, 2011.

U.S. Appl. No. 11/320,223, filed Dec. 28, 2005 Non-Final Office Action dated Mar. 16, 2011.

U.S. Appl. No. 11/380,124, filed Apr. 25, 2006 Non-Final Office Action dated Apr. 7, 2011.

U.S. Appl. No. 11/380,124, filed Apr. 25, 2006 Non-Final Office Action dated Oct. 28, 2010.

U.S. Appl. No. 11/937,302, filed Nov. 8, 2007 Final Office Action dated Feb. 11, 2011.

U.S. Appl. No. 11/937,302, filed Nov. 8, 2007 Non-Final Office Action dated Apr. 15, 2011.

U.S. Appl. No. 12/023,280, filed Jan. 31, 2008 Non-Final Office Action dated Dec. 13, 2010.

U.S. Appl. No. 12/023,280, filed Jan. 31, 2008 Notice of Allowance dated Mar. 28, 2011.

U.S. Appl. No. 12/419,854, filed Apr. 7, 2009 Non-Final Office Action dated Aug. 5, 2011.
U.S. Appl. No. 12/419,957, filed Apr. 7, 2009 Advisory Action dated Feb. 18, 2011.
U.S. Appl. No. 12/419,957, filed Apr. 7, 2009 Final Office Action dated Dec. 7, 2010.
U.S. Appl. No. 12/419,957, filed Apr. 7, 2009 Notice of Allowance dated Mar. 7, 2011.
U.S. Appl. No. 12/420,028, filed Apr. 7, 2009 Non-Final Office Action dated Jan. 5, 2011.
U.S. Appl. No. 12/420,028, filed Apr. 7, 2009 Notice of Allowance dated Apr. 1, 2011.
U.S. Appl. No. 12/617,981, filed Nov. 13, 2009 Advisory Action dated Sep. 15, 2011.
U.S. Appl. No. 12/617,981, filed Nov. 13, 2009 Final Office Action dated Jun. 21, 2011.
U.S. Appl. No. 12/617,981, filed Nov. 13, 2009 Non-Final Office Action dated Jan. 5, 2011.
U.S. Appl. No. 12/796,133, filed Jun. 8, 2010 Non-Final Office Action dated Feb. 17, 2011.
U.S. Appl. No. 12/796,133, filed Jun. 8, 2010 Notice of Allowance dated Jun. 9, 2011.
U.S. Appl. No. 12/419,854, filed Apr. 7, 2009 Non-Final Office Action dated Aug. 5, 2011.

\* cited by examiner

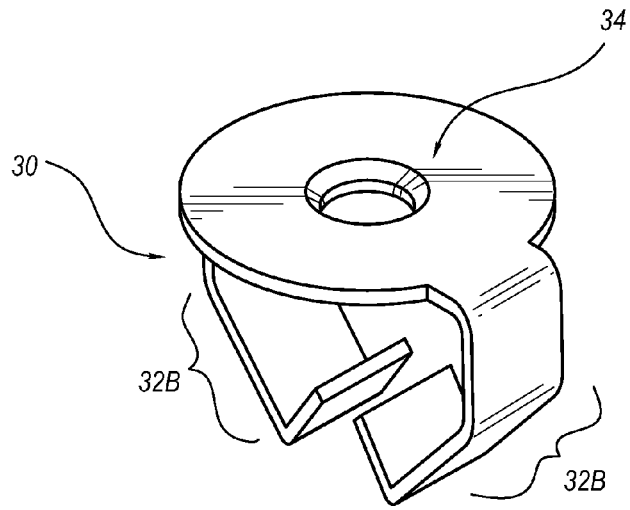
FIG. 24A
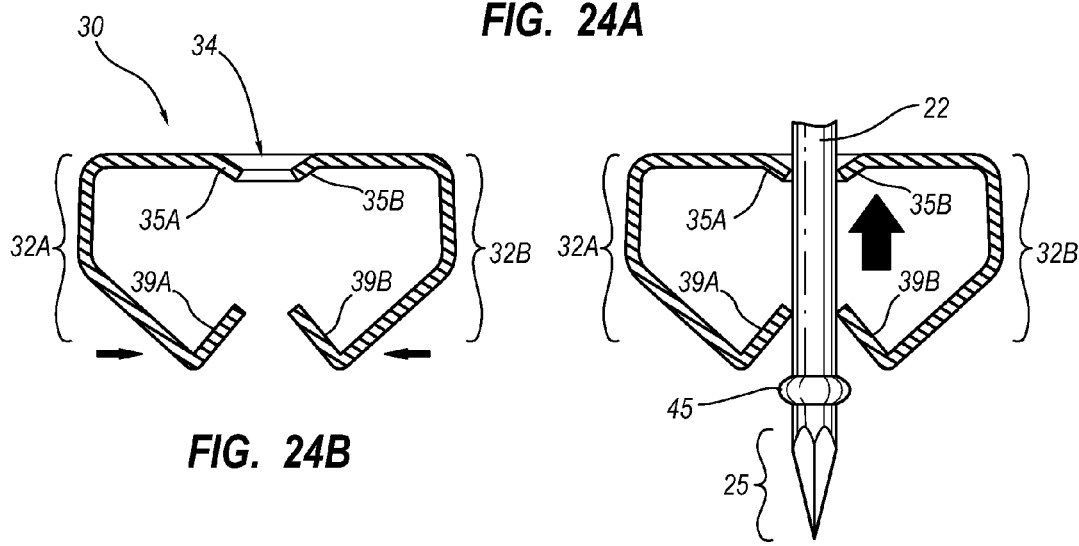
FIG. 24B
FIG. 24C
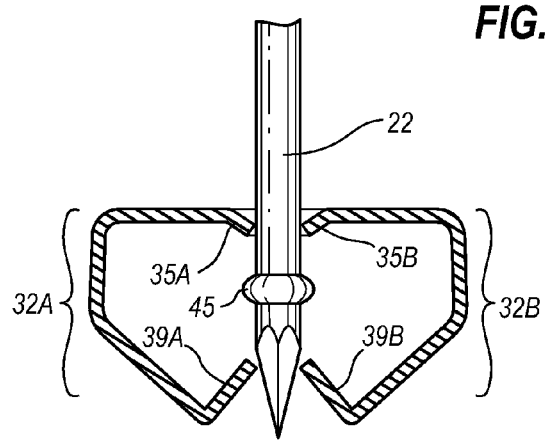
FIG. 24D

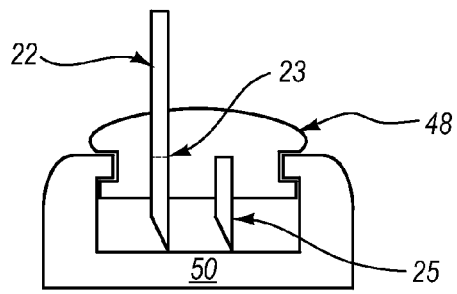
FIG. 29
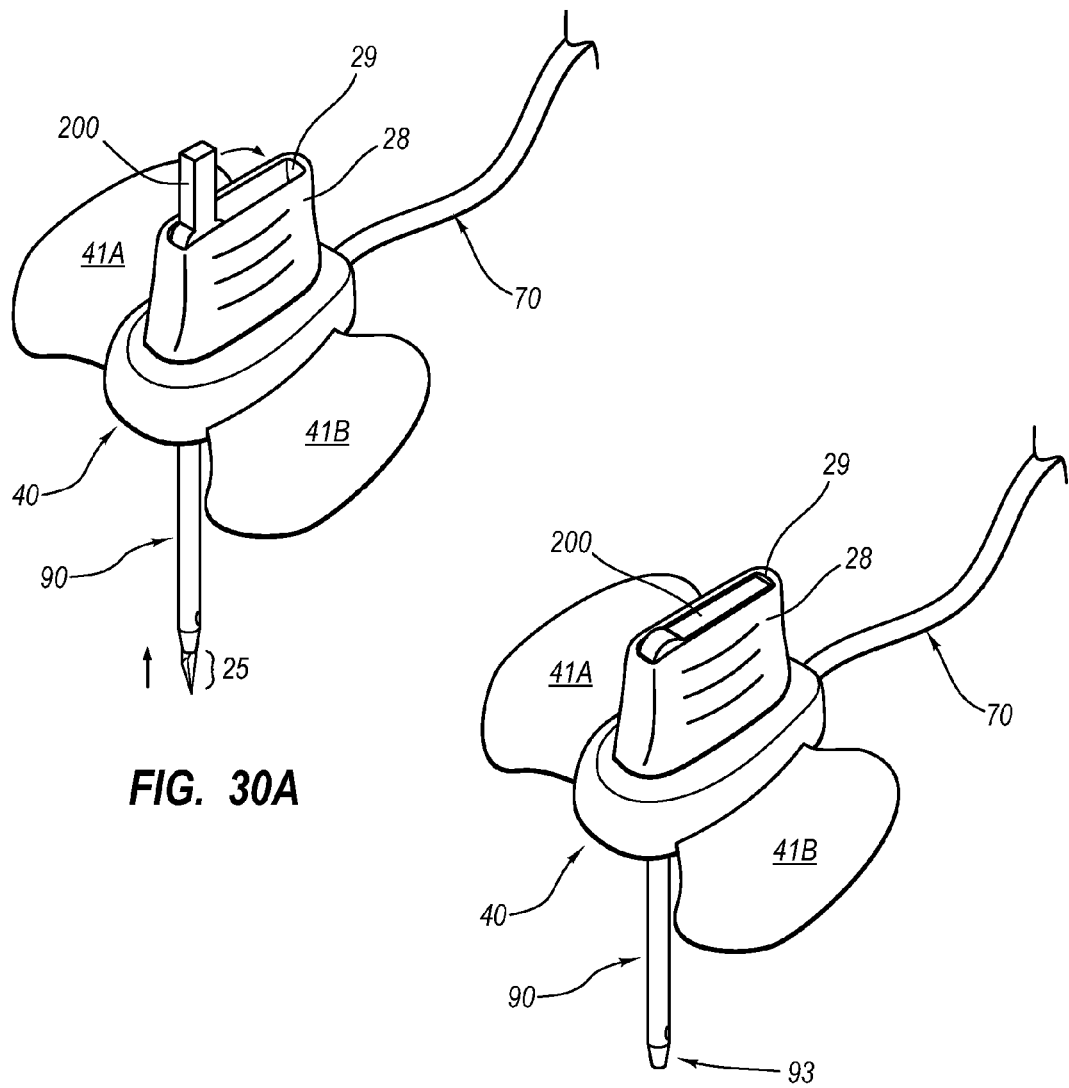
FIG. 30A
FIG. 30B

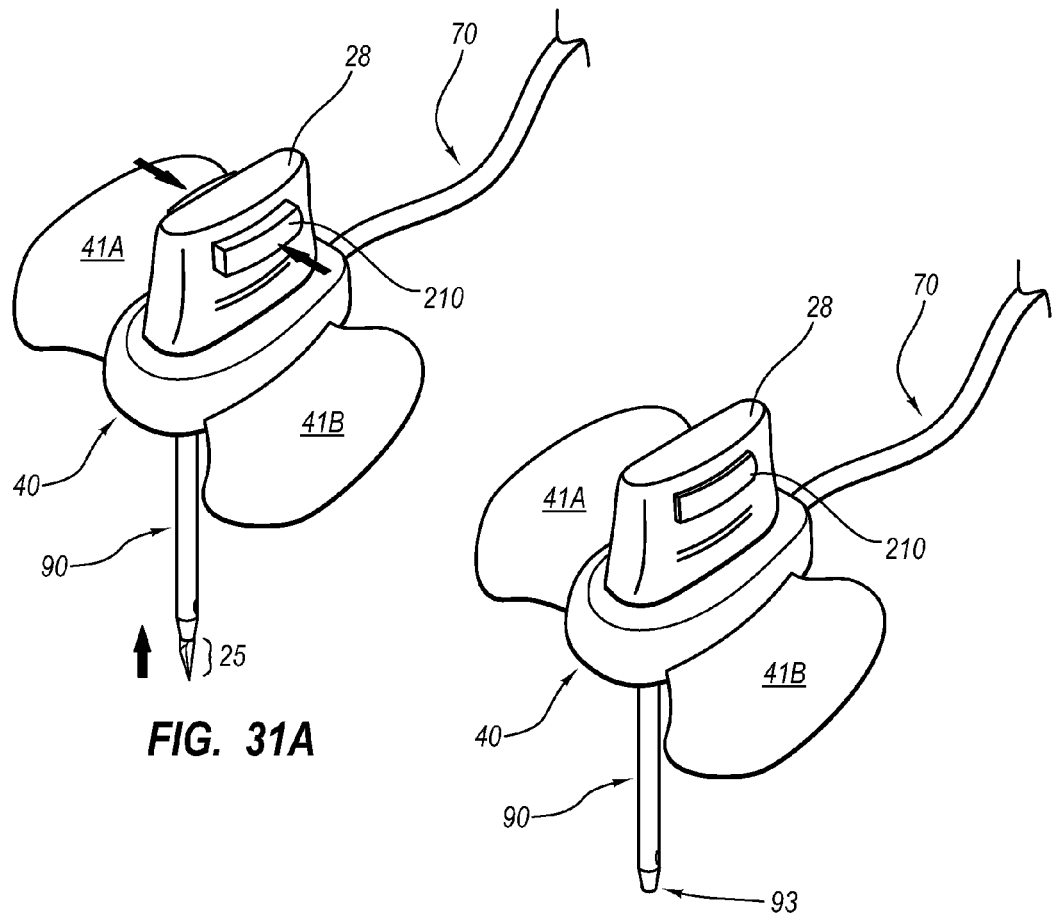
FIG. 31A
FIG. 31B
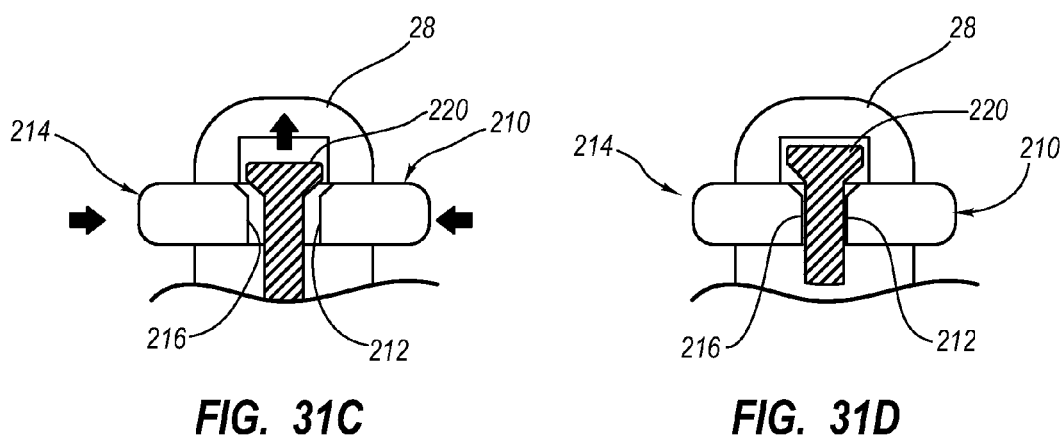
FIG. 31C  FIG. 31D

INFUSION APPARATUSES AND METHODS OF USE

CROSS REFERENCE TO RELATED APPLICATION

This application claims the benefit of U.S. Patent Application No. 60/675,309, filed 27 Apr. 2005, the disclosure of which is incorporated, in its entirety, by this reference.

BACKGROUND

Access to a patient's vascular system may be established by a variety of temporary or permanently implanted devices. For example, temporary access to a patient's vascular system may be accomplished by the direct percutaneous introduction of a needle into the patient's blood vessel. While such a temporary and direct approach may be relatively simple and suitable for applications that are limited in frequency or duration, such as intravenous feeding and/or intravenous drug delivery, this temporary approach may not be suitable for procedures that are frequently repeated or that require vascular access for relatively long time periods of time, such as hemodialysis or other similar extracorporeal procedures.

Accordingly, a variety of implantable devices have been proposed to provide a convenient method for repeatedly introducing fluids, such as medicaments, into the vasculature of a patient. Typically, such implantable device comprise a housing that encloses an internal fluid chamber or cavity. An access aperture defined through the housing and sealed by a penetrable septum provides access to the internal fluid chamber, which is typically in fluid communication with an implanted catheter attached to a patient's vasculature.

Quantities of fluid, such as medication, blood, or the like, may be introduced into, or withdrawn from, a patient's vasculature using conventional implantable device by: 1) penetrating the septum of the implanted device using a percutaneously inserted needle; 2) positioning at least the tip of the needle within the internal fluid reservoir or cavity enclosed in the device housing; and 3) discharging fluids through the needle into the internal fluid cavity. The discharged fluids may then be directed through the distal end of the implanted catheter connected to the implanted device to an entry point into the venous system of the body of the patient. Blood may also be aspirated through the implanted device in a similar manner.

SUMMARY

In at least one embodiment, an infusion apparatus for providing access to an implanted device, such as an access port or a pump (e.g., a so-called pain pump), may comprise an insertion assembly, a hub comprising a sealable path configured to receive at least a portion of the insertion assembly, a flexible catheter attached to the hub and configured to receive at least a portion of the insertion assembly, and an extension tube attached to the hub. In certain embodiments, the hub may comprise a plurality of wing structures and may be configured to provide fluid communication between the flexible catheter and the extension tube. The hub may also comprise a manifold element structured to provide fluid communication between the flexible catheter and the extension tube. In addition, the sealable path may comprise a septum configured to seal the sealable path upon removal of the insertion assembly from the flexible catheter. The extension tube may either be permanently or removably attached to the hub.

According to at least one embodiment, the insertion assembly may comprise a slender pointed element and both the sealable path and the flexible catheter may be configured to receive at least a portion of the slender pointed element. Similarly, the extension tube may be configured to receive at least a portion of the slender pointed element. The flexible catheter may also comprise at least one aperture defined proximate a distal end of the flexible catheter and the slender pointed element may comprise at least one longitudinally extending indentation defined along the slender pointed element. In at least one embodiment, a cross-sectional area defined between an exterior surface of the slender pointed element and an interior surface of the flexible catheter may approximate the cross-sectional area of a hollow needle gauge. In addition, the flexible catheter may comprise at least one aperture defined proximate a distal end of the flexible catheter and the slender pointed element may be at least partially hollow and comprise at least one aperture defined within the slender pointed element for communicating fluid with the at least one aperture defined in the flexible catheter.

In certain embodiments, at least a portion of the slender pointed element may be retractable into a recess defined in the insertion assembly. In addition, the flexible catheter may have a length that exceeds an anticipated insertion length such that, when the flexible catheter is fully inserted into a device implanted within a patient, a bendable portion of the flexible catheter may extend from a skin surface of the patient. The infusion apparatus may also comprise a receiving enclosure positioned substantially parallel to a skin surface of a patient and configured to receive at least a portion of the hub. Further, the infusion apparatus may comprise a safety clip configured to: 1) retain a pointed end of the slender pointed element within the safety clip when the slender pointed element is removed from the hub; and 2) allow the pointed end of the slender pointed element to pass through the safety clip when the slender pointed element is inserted into the hub. The infusion apparatus may also comprise a reinforcing member, which may be coiled, at least partially imbedded within the flexible catheter.

In at least one embodiment, an infusion device for use with an implanted device may comprise a slender pointed element comprising a pointed end, a flexible catheter comprising a sealable path configured to receive at least a portion of the slender pointed element, and an extension tube in fluid communication with the flexible catheter. In certain embodiments, the sealable path may be structured to seal upon removal of the slender pointed element from the flexible catheter.

In addition, an infusion apparatus for accessing an implanted device may comprise an insertion assembly comprising a slender pointed element, a hub comprising a sealable path configured to receive at least a portion of the slender pointed element, a flexible catheter attached to the hub and configured to receive at least a portion of the slender pointed element, and an extension tube attached to the hub. In certain embodiments, the hub may comprise a manifold element structured to provide fluid communication between the flexible catheter and the extension tube, and a septum configured to seal the sealable path upon removal of the slender pointed element from the flexible catheter.

In at least one embodiment, a method of providing a fluid communication path to an implanted device may comprise positioning at least a portion of a slender pointed element within a flexible catheter, penetrating a septum of an implanted device with the slender pointed element positioned within the flexible catheter, positioning at least a portion of the flexible catheter within the implanted device, removing the slender pointed element from the flexible catheter, and retaining at least a portion of the flexible catheter within the implanted device. The method may also comprise providing a hub in fluid communication with the flexible catheter, and removably attaching an extension tube to the hub to provide fluid communication between the flexible catheter and the extension tube. In addition, the method may comprise sealing a sealable path defined in the hub upon removal of the slender pointed element from the flexible catheter.

In certain embodiments, this exemplary method may further comprise positioning at least a portion of the slender pointed element within the extension tube. In addition, this method may further comprise retracting at least a portion of the slender pointed element into the flexible catheter. The method may also further comprise providing a safety clip proximate a pointed end of the slender pointed element, and retaining the pointed end of the slender pointed element within the safety clip upon removal of the slender pointed element from the flexible catheter.

Features from any of the above-mentioned embodiments may be used in combination with one another in accordance with the general principles described herein. These and other embodiments, features and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

FIGS. 24A-24D are perspective and cross-sectional side views of an additional embodiment of a safety clip;

FIG. 29 is a cross-sectional side view of an exemplary slender pointed element comprising a scored pointed end;

FIGS. 30A-30B are perspective views of an infusion system according to an additional embodiment;

FIGS. 31A-31B are perspective views of an infusion system according to an additional embodiment;

FIGS. 31C-31D are cross-sectional side views of the exemplary infusion system illustrated in FIGS. 31A-31B;

Figure 1:
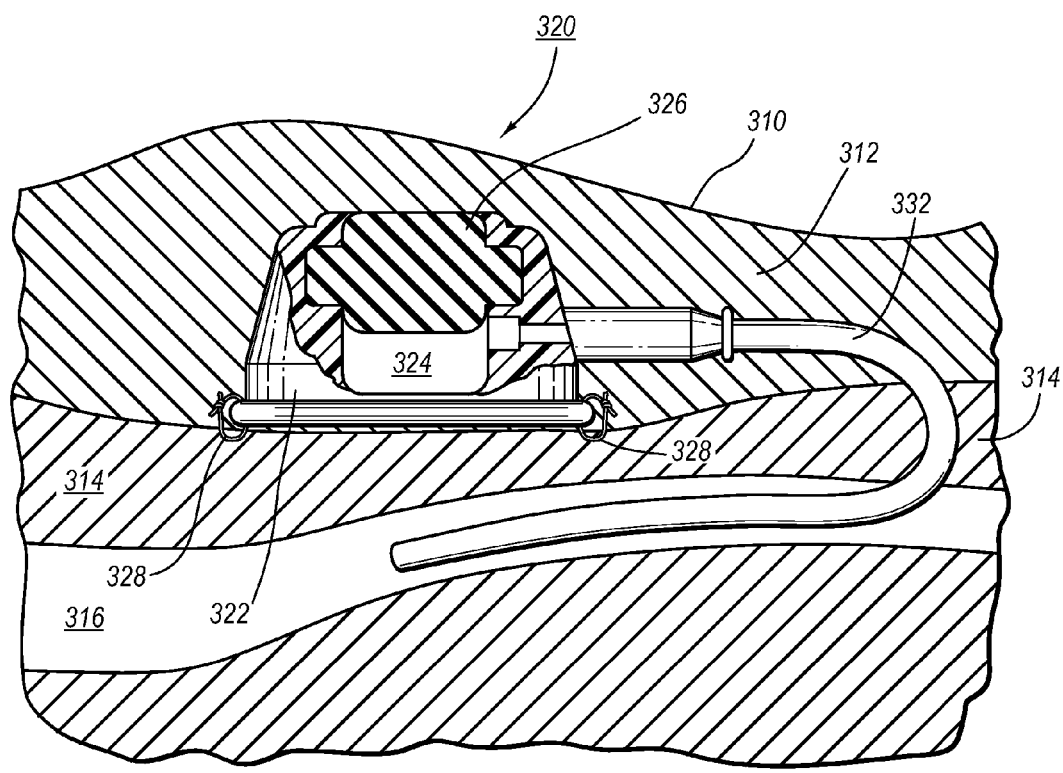
FIG. 1 is a schematic cross-sectional side view of an exemplary device implanted within a patient.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, one of skill in the art will understand that the exemplary embodiments described herein are not intended to be limited to the particular forms disclosed. Rather, the instant disclosure covers all modifications, equivalents, and alternatives falling within the scope defined by the appended claims.

DETAILED DESCRIPTION

Generally speaking, one or more of the exemplary apparatuses, devices, and/or methods described and illustrated herein may be employed for percutaneously accessing a device, such as an access port or pump (e.g., a so-called pain pump), implanted within a patient, such as exemplary access port 320 illustrated in FIG. 1. Access port 320 generally represents any device capable of being implanted within a patient, such as an access port, pump, or other device known to those of skill in the art. As illustrated in FIG. 1, exemplary access port 320 may comprise a housing 322 and a septum 326 defining a chamber 324. A catheter 332 in fluid communication with the vasculature 316 of a patient may be attached to housing 322 to provide a fluid communication path between exemplary access port 320 and vasculature 316. In at least one embodiment, access port 320 is implanted within the interior of a patient; namely, below skin surface 310 and within subcutaneous zone 312. In certain embodiments, access port 320 may be implanted beneath skin surface 310 by a distance in the range from about 3 mm to about 20 mm, and/or from about 5 mm to about 15 mm. Housing 322 of access port 320 may then be secured to deep fascia tissue 314 by a plurality of sutures 328. Catheter 332 may be surgically implanted, indwelling, or secured within the patient in any other manner known to those of skill in the art.

Figure 2:
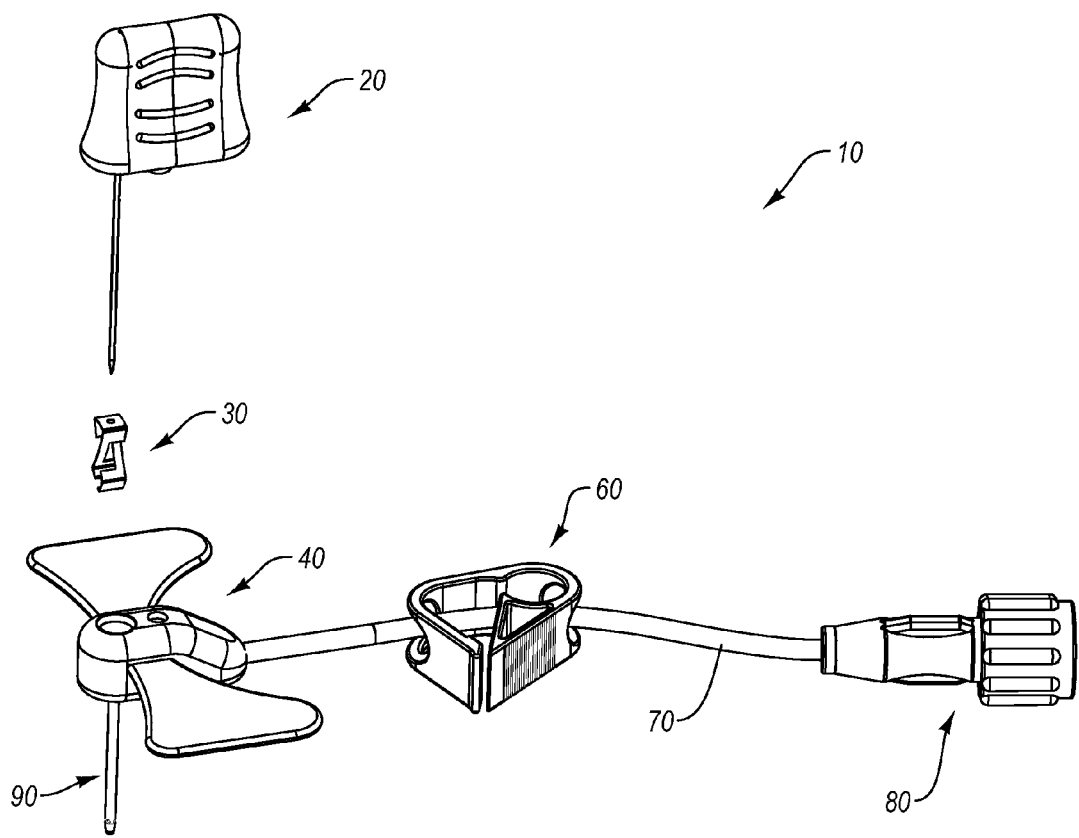
FIG. 2 is an exploded perspective view of an exemplary infusion system according to at least one embodiment.

FIG. 2 is an exploded perspective view of an exemplary infusion system 10 for accessing an implanted device, such as exemplary access port 320 illustrated in FIG. 1. As seen in FIG. 2, exemplary infusion system 10 may comprise an insertion assembly 20, a safety clip 30, a hub 40, a flexible catheter 90, an extension tube 70, a clamp device 60, and a tube connector 80. Generally, the various components of infusion system 10 may comprise any number or combination of suitable materials known to those of skill in the art, such as metals, plastics, or polymers. For example, the various components of infusion system 10 may comprise polytetrafluoroethylene (PTFE), polypropylene, silicone, stainless steel (e.g., AISI 304 stainless steel), fluorinatedethylenepropylene (FEP), perfluoroalkoxy (PFA), ethylenetetrafluoroethylene (ETFE), polyetheretherketone (PEEK®), polyurethane (including thermoplastic polyurethanes, such as ISOPLAST®, TECOFLEX®, TECOTHANE®, CARBOTHANE®, TECOPLAST®, or TECOPHILIC®-type polyurethanes), or any number of combinations thereof.

Figure 3A:
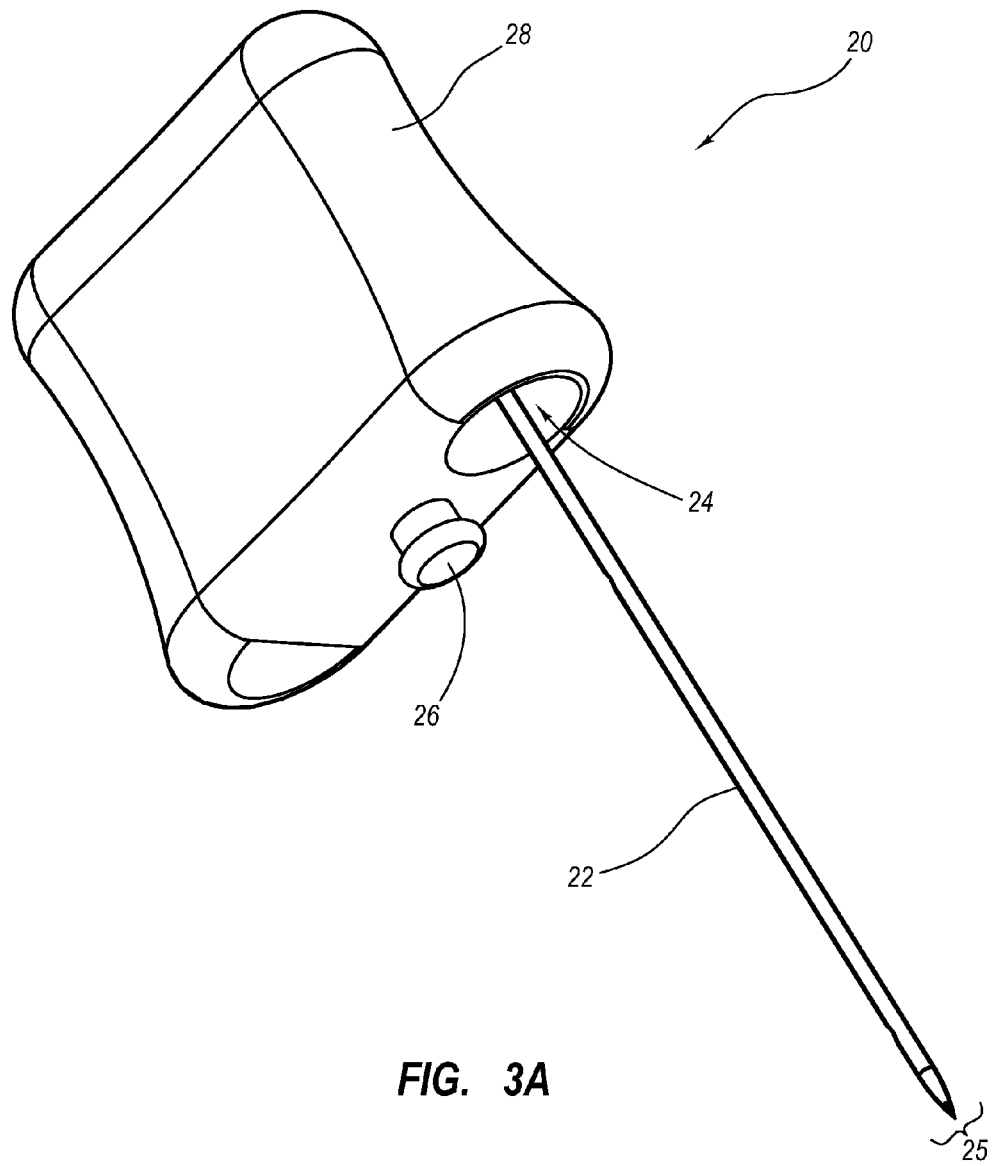
FIG. 3A is a perspective view of an exemplary insertion assembly according to at least one embodiment.
Figure 3B:
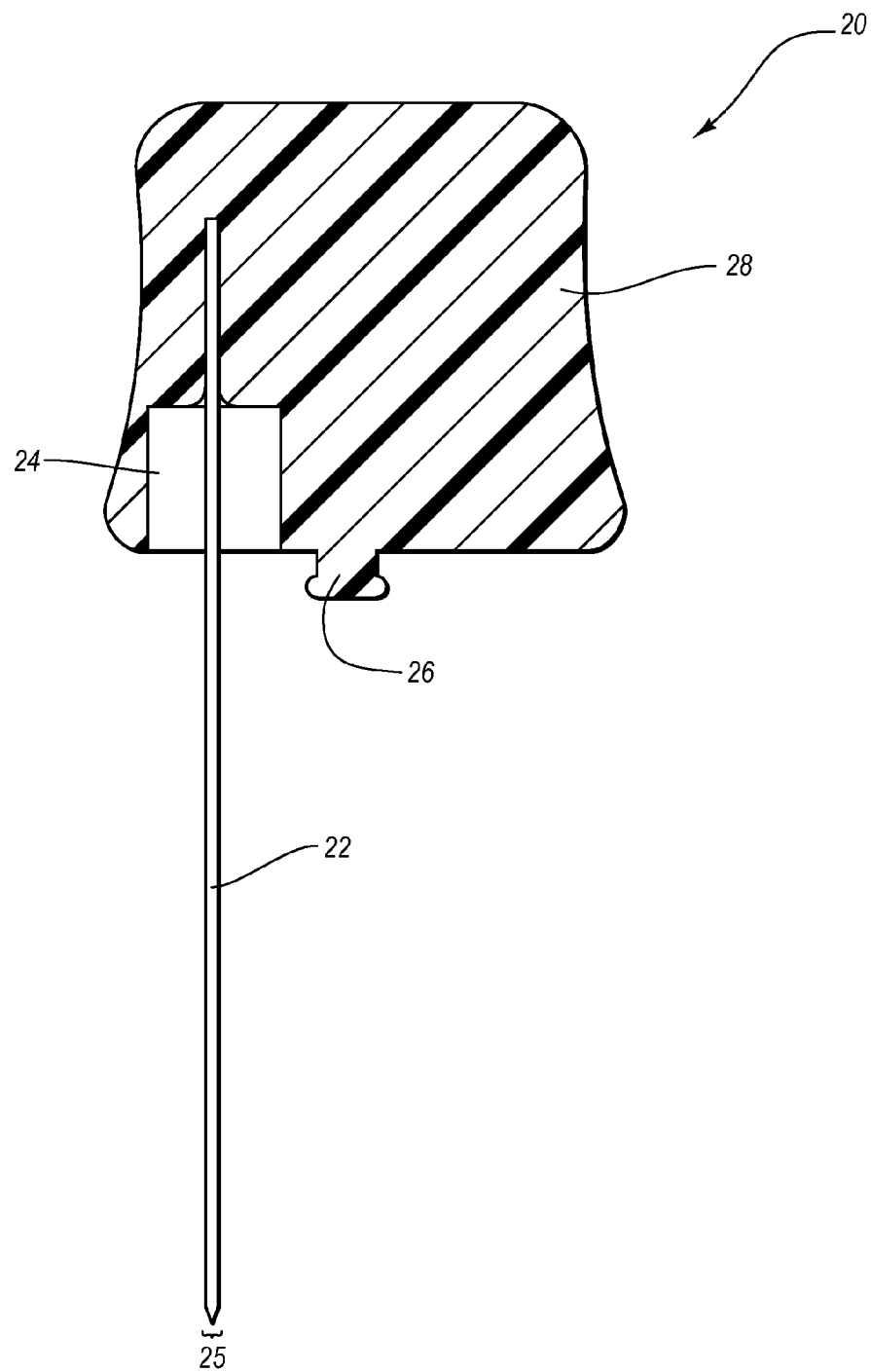
FIG. 3B is a cross-sectional side view of the exemplary insertion assembly illustrated in FIG. 3A.

FIGS. 3A and 3B are perspective and cross-sectional side views, respectively, of an exemplary insertion assembly 20. As seen in these figures, exemplary insertion assembly 20 may comprise a slender pointed element 22 attached to a base member 28. Slender pointed element 22 generally represents any structure capable of penetrating the septum of an implanted device, such as septum 326 of access port 320. For example, slender pointed element 22 may represent a trocar, a coring or non-coring needle, a cannula, or any other suitable hollow or solid structure. Slender pointed element 22 may be entirely solid, entirely hollow, or may include a solid pointed end 25 and an at least partially hollow body, as discussed in greater detail below. In addition, slender pointed element 22 may comprise any conventional needle, trocar, or cannula material, such as stainless steel (e.g., AISI 304 stainless steel), plastic, or the like.

As seen in FIGS. 3A and 3B, a recess 24 may be defined within base member 28. In at least one embodiment, recess 24 is configured to receive one or more structural elements, such as, for example, safety clip 30. Base member 28 may also comprise a coupling structure 26, which generally represents any structure (e.g., a protrusion) or recess capable of coupling base member 28 to an additional element, such as hub 40. In at least one embodiment, coupling structure 26 couples to a complimentary coupling recess 44 defined in hub 40 (illustrated in FIGS. 4A-4C). In certain embodiments, base member 28 may be injection molded or otherwise formed about slender pointed element 22 so as to capture a portion of slender pointed element 22 within the base member 28, as best seen in FIG. 3B.

Figure 4A:
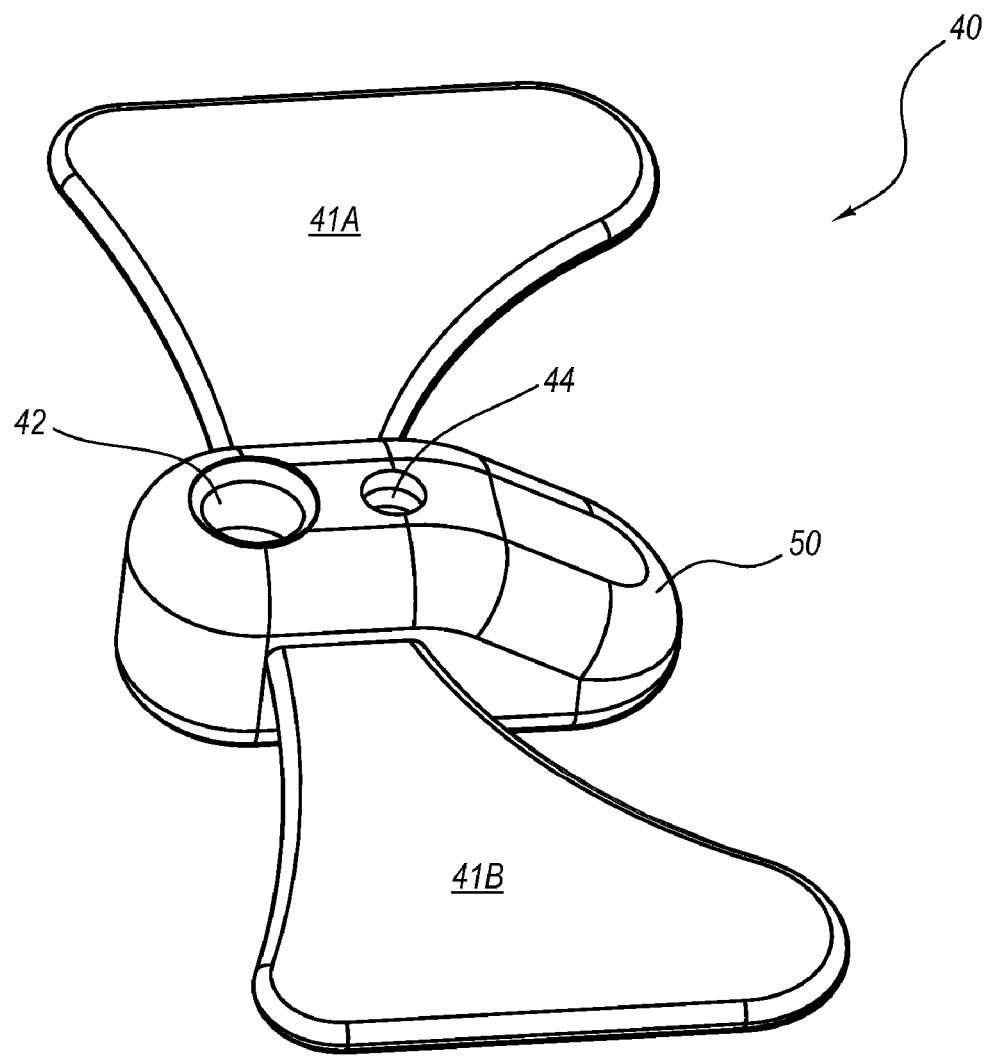
FIG. 4A is a perspective view of an exemplary hub according to at least one embodiment.
Figure 4B:
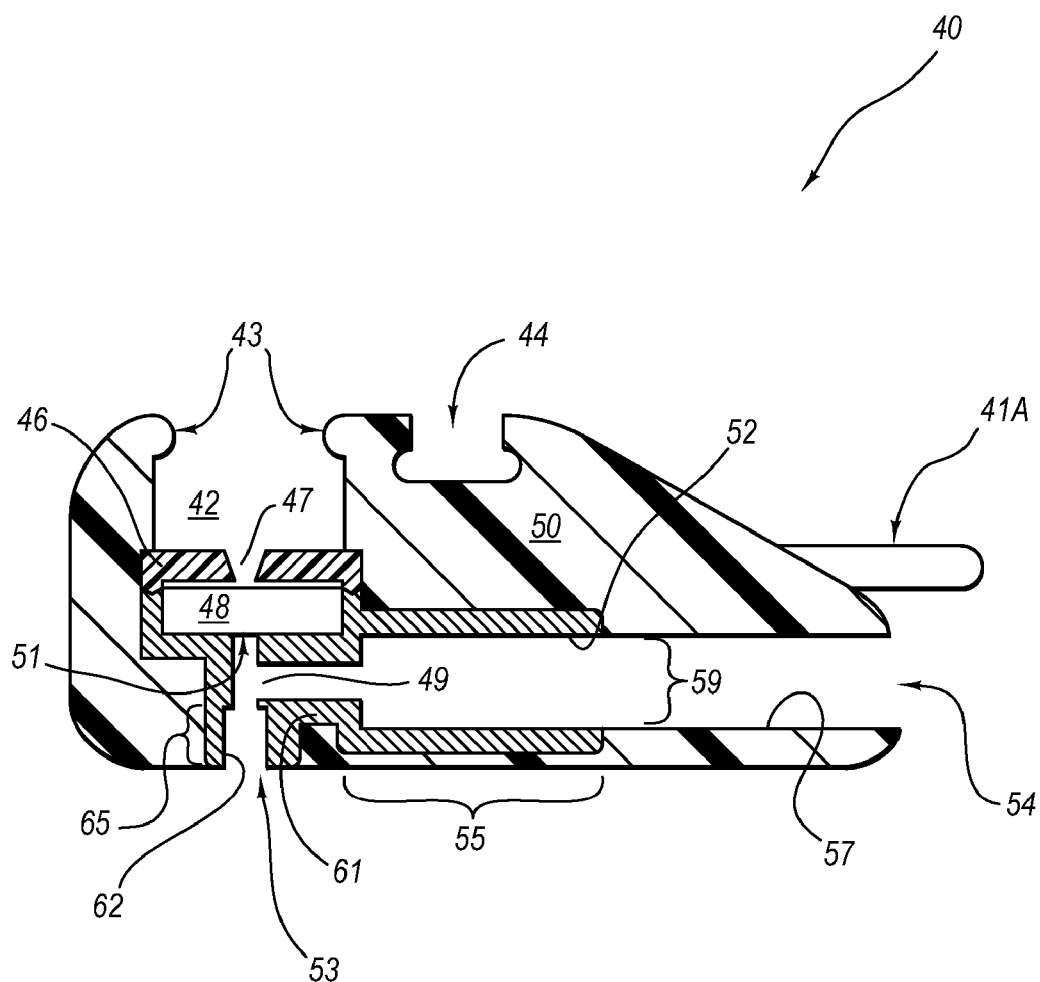
FIG. 4B is a cross-sectional side view of the exemplary hub illustrated in FIG. 4A.

FIGS. 4A and 4B are perspective and cross-sectional views, respectively, of an exemplary hub 40 according to at least one embodiment. As seen in these figures, exemplary hub 40 may comprise a plurality of wing structures 41A and 41B attached to a hub body 50. In at least one embodiment, wing structures 41A and 41B are configured to affix exemplary hub 40 to the skin of a patient. For example, wing structures 41A and 41B may be taped, adhesively affixed, or otherwise attached to the surface of a patient's skin, such as skin surface 310 in FIG. 1. Generally speaking, wing structures 41A and 41B may be formed in any number of shapes and sizes, including those illustrated in FIGS. 20A-20B, 22A-22B, 25A-25B, 26A-26C, 27A-27B, 30A-30B, 31A-31B, and 33A-33D. As detailed above, exemplary hub 40 and wing structures 41A and 41B may comprise any number or combination of suitable materials known to those of skill in the art, including, for example, TECOFLEX® 85A-B20.

As illustrated in FIG. 4B, in certain embodiments a coupling recess 44 may be defined within hub body 50 and structured to receive the complimentary coupling structure 26 provided on base member 28. Similarly, a recess 42 may be defined in hub body 50 and configured to receive both a slender pointed element (such as slender pointed element 22) and a safety clip (such as safety clip 30), as discussed in greater detail below. A retaining lip 43 may also be provided within recess 42 for retaining a safety clip, such as safety clip 30, within recess 42.

In at least one embodiment, a penetrable septum 48 may be provided in recess 42 and positioned above a manifold element 61 defined in exemplary hub body 50. A cap element 46 may also be positioned above septum 48 and configured to retain septum 48 within recess 42. As illustrated in FIG. 4B, manifold element 61 may define a plenum 49 in communication with a plurality of openings (e.g., openings 51, 53, and 59) sealed by at least one septum (e.g., septum 48). An aperture 47 may also be defined within cap element 46 generally opposite opening 51 of plenum 49. In certain embodiments, septum 48 may comprise any suitable material capable of suitably sealing opening 51 of plenum 49; including, for example, medical-grade polymers (such as silicone) and monomers (such as Ethylene Propylene Diene Monomer ("EPDM"), or other suitable materials.

In at least one embodiment, exemplary hub 40 may be structured to receive at least a portion of insertion assembly 20. For example, hub 40 may be configured to receive at least a portion of a slender pointed element, such as slender pointed element 22, within a sealable path defined within hub 40. In at least one embodiment, such a sealable path may be defined by, for example, recess 42, aperture 47, septum 48, opening 51, and opening 53. In this example, slender pointed element 22 may be inserted into aperture 47 in cap element 46 and passed through septum 48 and openings 51 and 53. In certain embodiments, penetrable septum 48 may be configured to seal opening 51 of plenum 49 upon removal of slender pointed element 22 from hub 40. Accordingly, slender pointed element 22 of insertion assembly 20 may be inserted through and removed from septum 48 without compromising the seal provided across opening 51. Further, the presence of cap element 46 may allow for so-called power or high-pressure injection to occur via manifold element 61, wherein pressures within manifold element 61 may reach about 400 psi or higher.

Figure 4C:
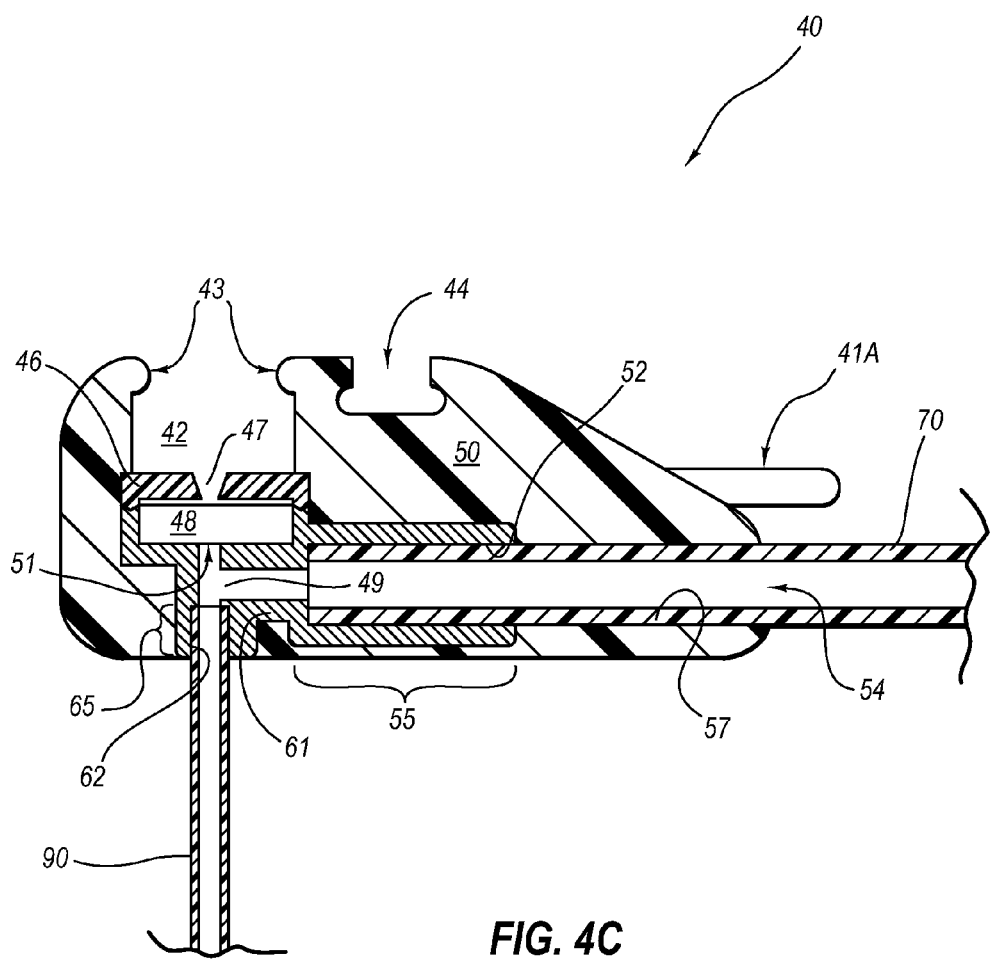
FIG. 4C is a cross-sectional side view of an exemplary flexible catheter and extension tube attached to the exemplary hub illustrated in FIG. 4A.

In embodiments, manifold element 61 may be configured to provide fluid communication between opening 53 and opening 59. More particularly, as illustrated in FIG. 4C, manifold element 61 may comprise a port extension 55 configured to receive at least a portion of an extension tube, such as extension tube 70, and a port extension 65 configured to receive at least a portion of a flexible catheter, such as flexible catheter 90. In at least one embodiment, an inner surface area 52 within port extension 55 of manifold element 61 may support the portion of extension tube 70 positioned within manifold element 61, such that relatively high pressures may be experienced without failure of extension tube 70. Similarly, an inner surface area 62 within port extension 65 of manifold element 61 may support the portion of flexible catheter 90 positioned within manifold element 61, such that relatively high pressures may be experienced without failure of flexible catheter 90.

As illustrated in FIG. 4B, hub 40 may also comprise a channel defined by a surface 57 and extending from opening 54 to opening 59 of manifold element 61. Such a channel may be sized and configured to receive at least a portion of an extension tube, such as extension tube 70, and may be formed prior to positioning of an extension tube within manifold element 61 or, in another embodiment, fabricated by forming (e.g., injection molding, curing, etc.) hub body 50 around extension tube 70. In an additional embodiment, hub body 50 of hub 40 may simply terminate substantially at opening 59 of manifold element 61.

In certain embodiments, flexible catheter 90 may be affixed to inner surface 62 of port extension 65. Similarly, extension tube 70 may be affixed to surface 52 of port extension 55. In one example, extension tube 70 and flexible catheter 90 may be chemically bonded to inner surfaces 52 and 62 of manifold element 61, respectively. In another example, an adhesive may be used to affix extension tube 70 and flexible catheter 90 to inner surfaces 52 and 62 of manifold element 61, respectively. Optionally, hub body 50 may be injection molded, cured, or otherwise formed around manifold element 61 (and, optionally septum 48, cap element 46, or both) and at least a portion of extension tube 70, as shown in FIG. 4C. Hub body 50 may also be formed around at least a portion of flexible catheter 90 in a similar manner. In addition, as discussed in greater detail below in connection with FIGS. 26A-26C and 27A-27B, extension tube 70 and/or flexible catheter 90 may be configured to be removably attached to manifold element 61 and/or hub 40.

Figure 5:
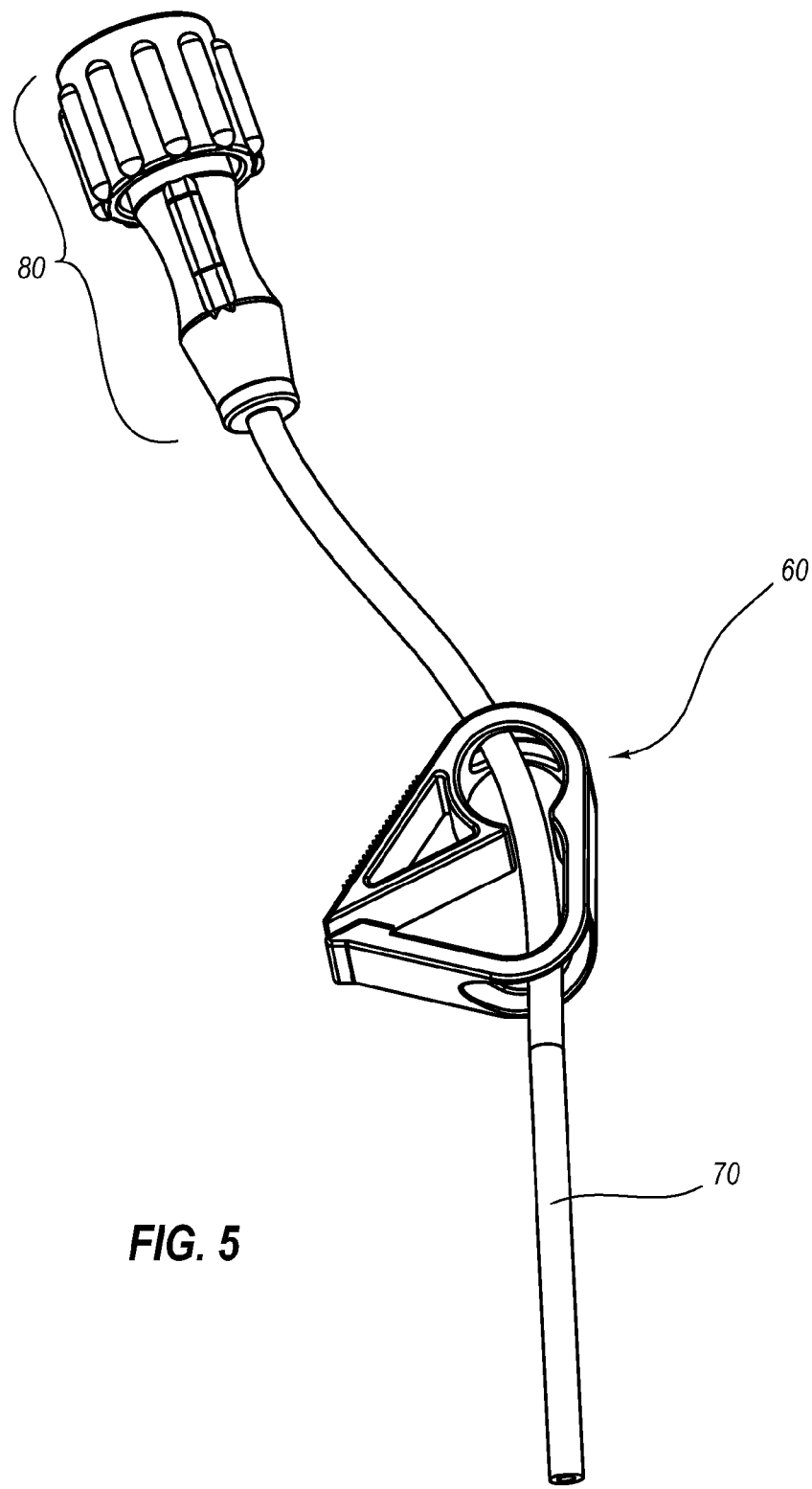
FIG. 5 is a perspective view of an extension tube, clamp device, and tube connector according to at least one embodiment.

FIG. 5 is a perspective view of an extension tube 70, a clamp device 60, and a tube connector 80 according to at least one embodiment. Extension tube 70 generally represents any form of medical tubing known to those of skill in the art. Similarly, clamp device 60 generally represents any form of tubing clamp known to those of skill in the art; including, for example, a slide clamp, a so-called pinch clamp, or the like. In addition, tube connector 80 generally represents any form of tubing connection or mechanism known to those of skill in the art; including, for example, a so-called Luer-type fitting or connector.

Figure 6:
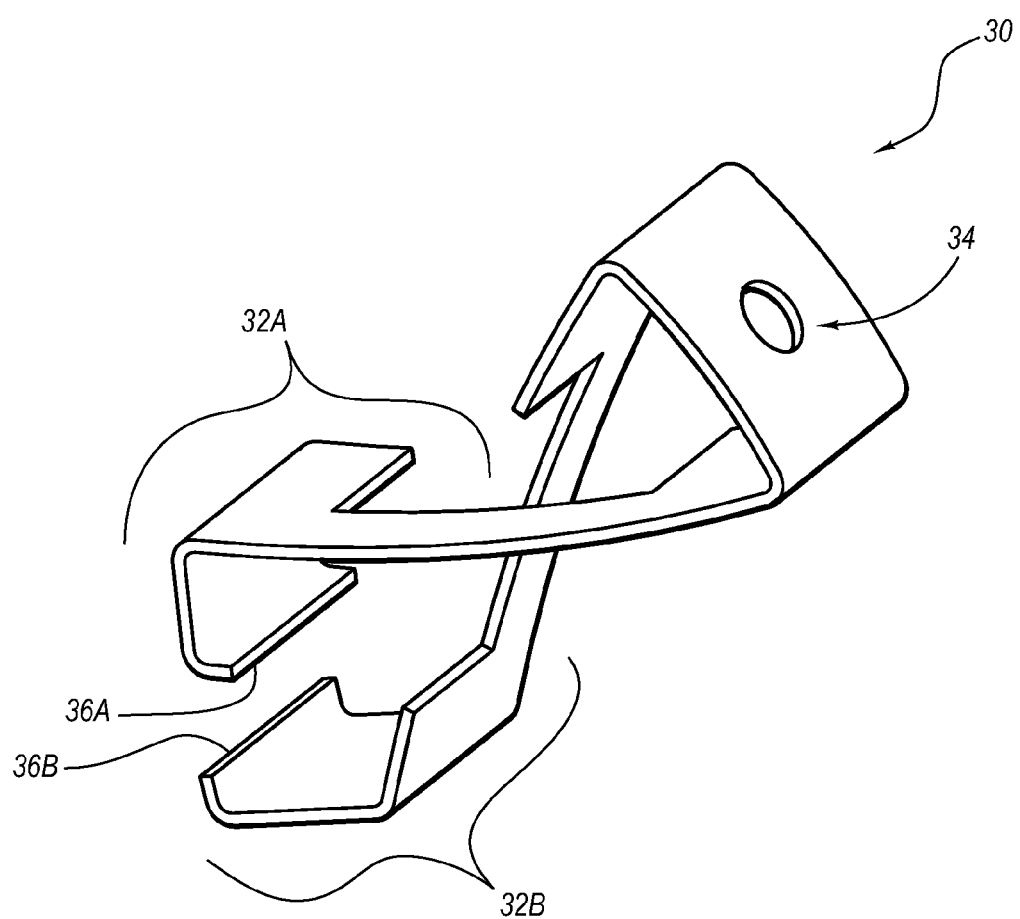
FIG. 6 is a perspective view of a safety clip according to at least one embodiment.

FIG. 6 is a perspective view of a safety clip 30 according to at least one embodiment. Safety clip 30 generally represents any self-actuating device for capturing a pointed end of a slender pointed element, such as pointed end 25 of slender pointed element 22. In the exemplary embodiment illustrated in FIG. 6, safety clip 30 may comprise a plurality of legs 32A and 32B having curved end regions 36A and 36B, respectively, and a hole 34 sized for receiving a slender pointed element, such as slender pointed element 22. Safety clip 30 may also be sized to fit within the retaining lips 43 provided in recess 42 of hub 40.

In at least one embodiment, safety clip 30 is attached to slender pointed element 22 by passing the pointed end 25 of slender pointed element 22 through hole 34 of safety clip 30, past legs 32A and 32B, and past curved end regions 36A and 36B. Once pointed end 25 of slender pointed element 22 has passed curved end regions 36A and 36B, legs 32A and 32B may clamp around slender pointed element 22 to removably affix the safety clip to slender pointed element 22. As slender pointed element 22, together with safety clip 30, is inserted into recess 42 defined in hub body 50, slender pointed element 22 may continue through safety clip 30 and into the sealable path defined in hub body 50. In addition, legs 32A and 32B of safety clip 30 may be biased such that, upon removal of slender pointed element 22 from the sealable path defined in hub body 50, curved end regions 36A and 36B may close around the pointed end 25 of slender pointed element 22 to retain this pointed end 25 within the body of safety clip 30. Such a safety clip 30 may prevent inadvertent insertion of slender pointed element 22 into another person, such as a medical practitioner utilizing infusion system 10.

Figure 7:
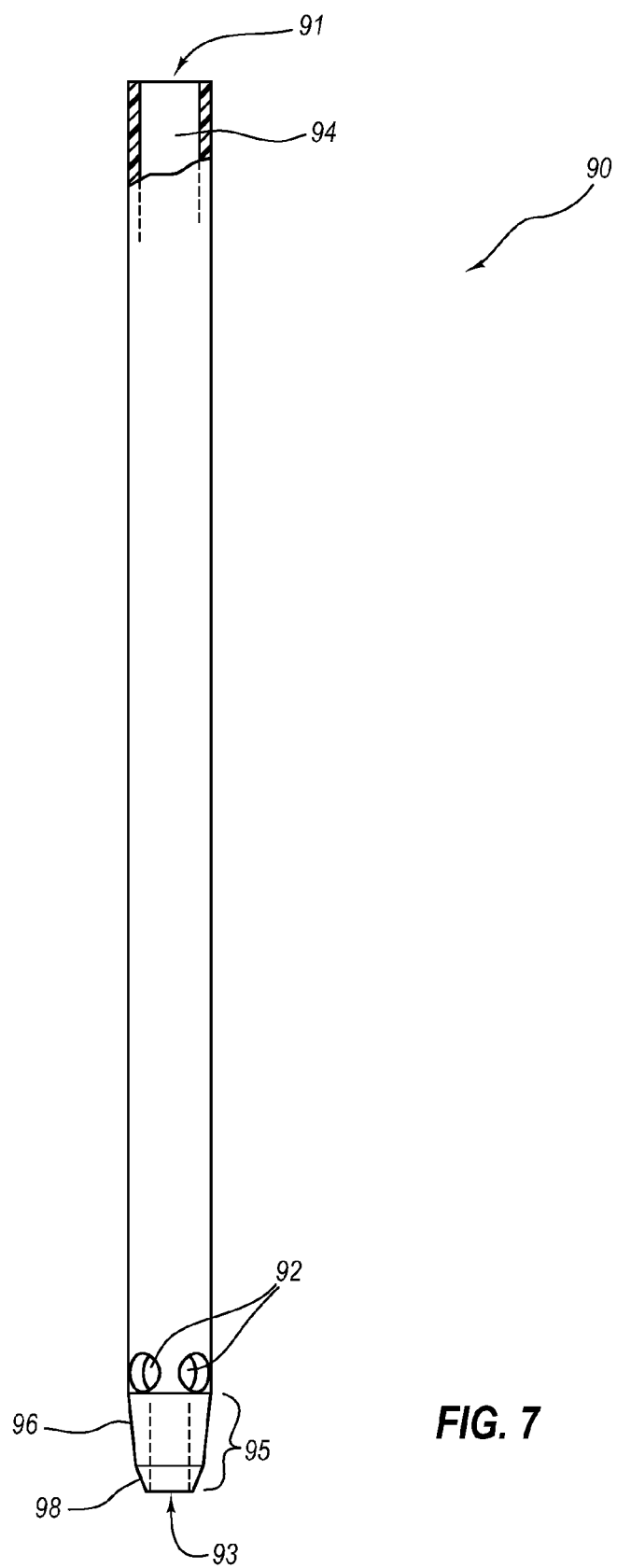
FIG. 7 is a partial perspective view and partial cross-sectional side view of a flexible catheter according to at least one embodiment.

FIG. 7 is a partial perspective view and partial cross-sectional side view of a flexible catheter 90 according to at least one embodiment. As seen in this figure, flexible catheter 90 may comprise an elongated lumen 94 extending between a first opening 91 and a second opening 93. Flexible catheter 90 may also comprise, proximate to second opening 93, a tapered transition region 95. As shown in FIG. 7, tapered transition region 95 may comprise a first tapered sub-region 96 and a second tapered sub-region 98. In certain embodiments, second tapered sub-region 98 is tapered more sharply than first tapered sub-region 96. Optionally, tapered transition region 95 may comprise a single taper and at least one arcuate surface. Exemplary flexible catheter 90 may also comprise at least one aperture 92 defined within flexible catheter 90 proximate second opening 93. In at least one embodiment, aperture 92 is defined through the tubular body of flexible catheter 90 to provide a fluid communication path between first opening 91 and aperture 92 through lumen 94. As detailed above, flexible catheter 90 may comprise any number or combination of suitable materials known to those of skill in the art, including, for example, TECOTHANE® (e.g., TECOTHANE® TT1055 D).

Figure 8A:
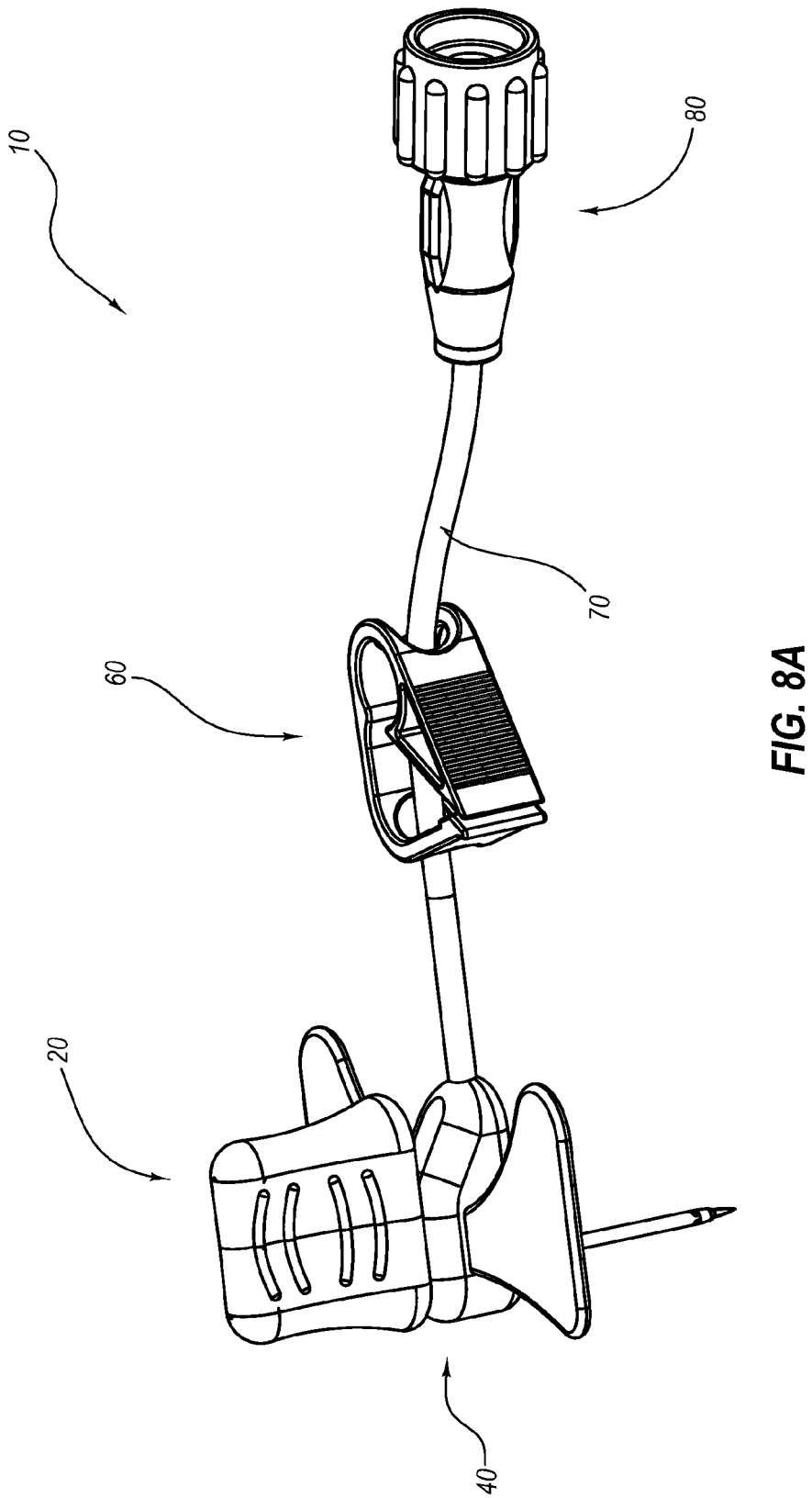
FIG. 8A is an assembled perspective view of the exemplary infusion system illustrated in FIG. 1.
Figure 8B:
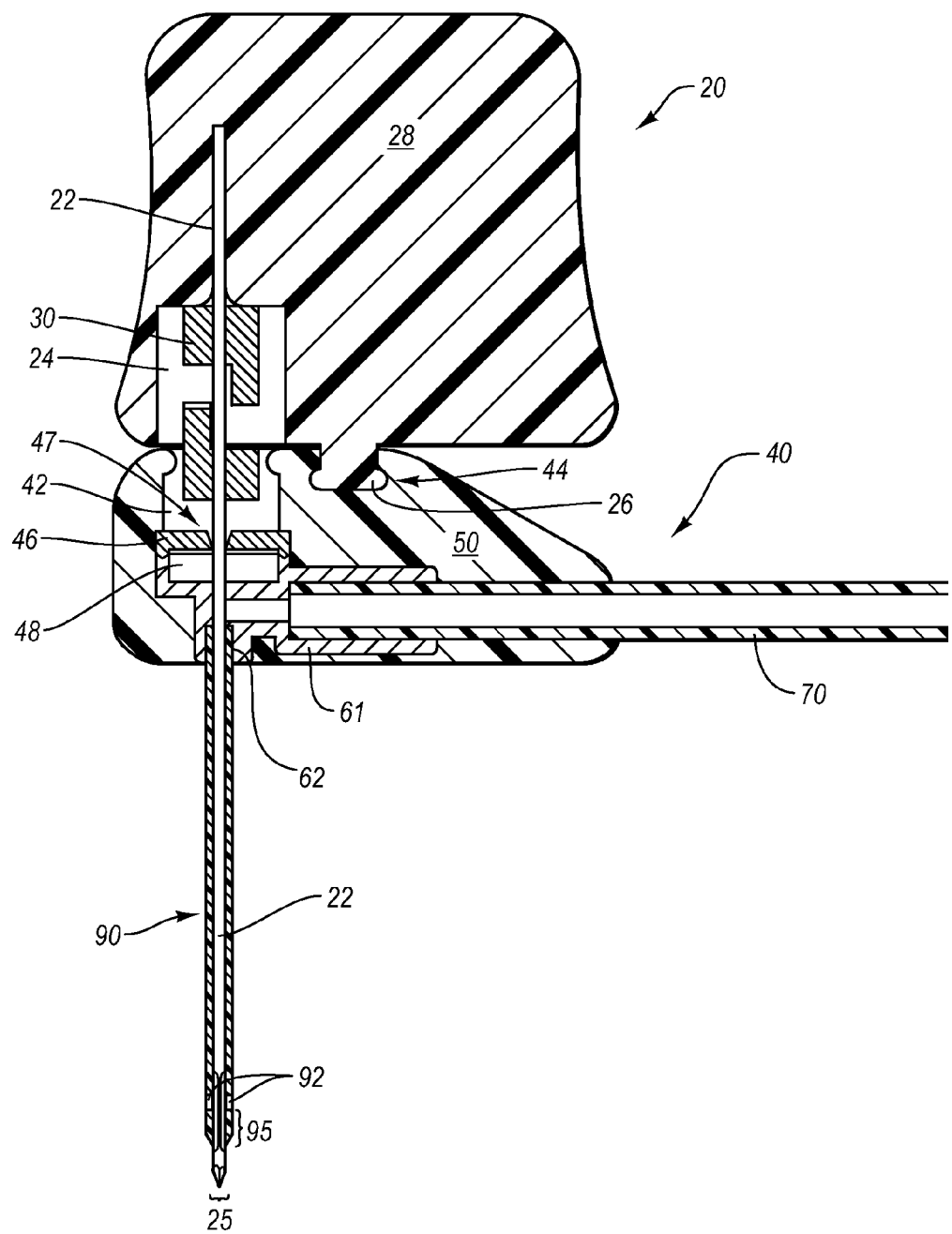
FIG. 8B is a partial cross-sectional side view of the exemplary infusion system illustrated in FIG. 8A.

FIGS. 8A and 8B are assembled perspective and cross-sectional views, respectively, of the exemplary infusion system 10 illustrated in FIG. 1. As seen in these figures, when insertion assembly 20 is coupled to exemplary hub 40 via coupling structure 26 and coupling recess 44, at least a portion of slender pointed element 22 may extend through safety clip 30, through aperture 47 of cap element 46, and into flexible catheter 90. In at least one embodiment, the length of slender pointed element 22 is chosen such that, when insertion assembly 20 is coupled to the hub body 50 of exemplary hub 40, the pointed end 25 of slender pointed element 22 extends beyond the second opening 93 of flexible catheter 90. Accordingly, when so assembled, slender pointed element 22 and flexible catheter 90 provide, in combination, a rigid, pointed structure capable of penetrating the septum of an implanted device, such as septum 326 of the exemplary access port 320 illustrated in FIG. 1.

Figure 8C:
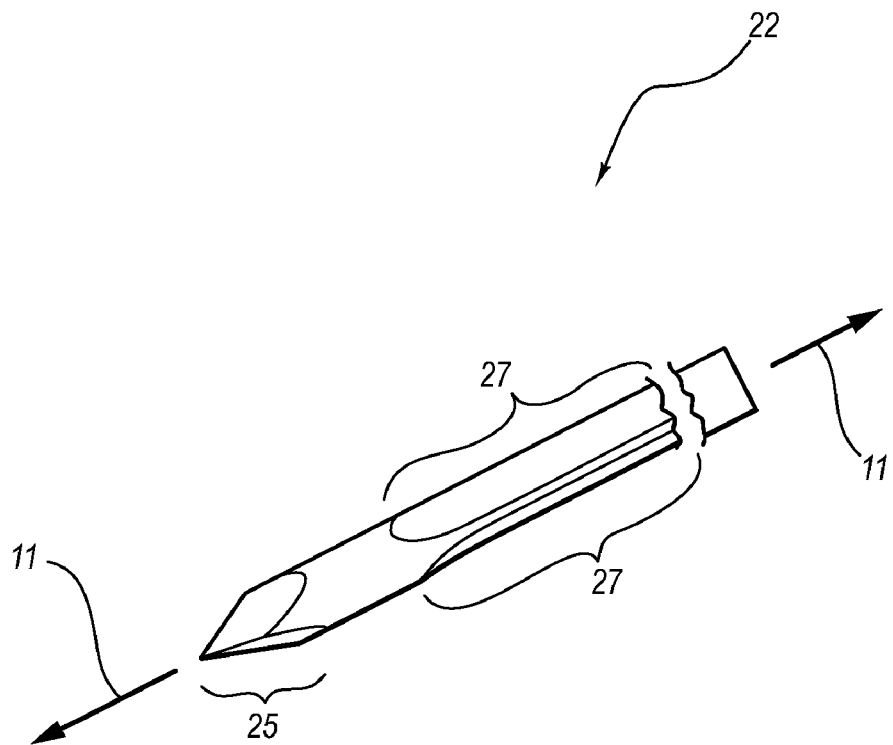
FIG. 8C is a partial perspective view of a slender pointed element according to at least one embodiment.
Figure 8D:
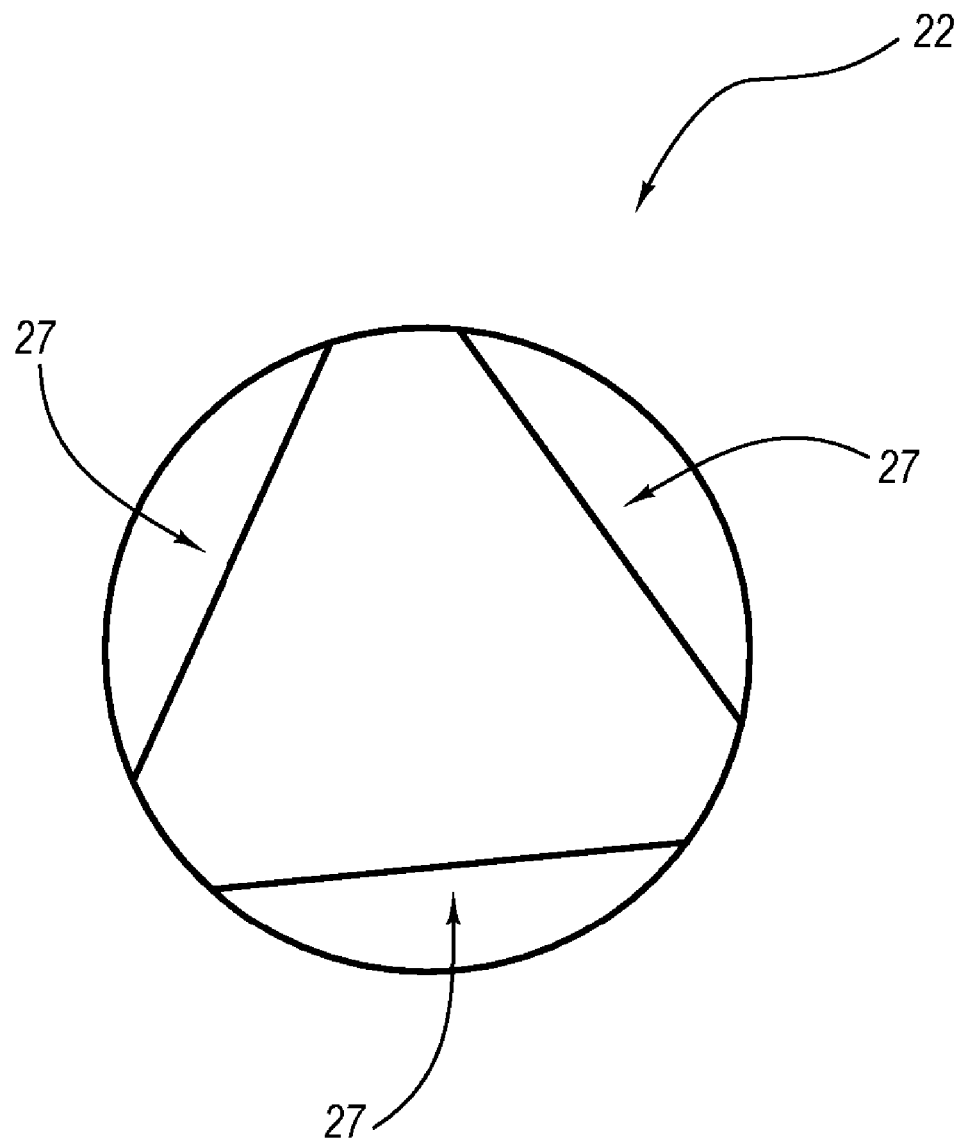
FIG. 8D is an end view of the exemplary slender pointed element illustrated in FIG. 8C.

FIGS. 8C and 8D are perspective and end views, respectively, of a slender pointed element 22 according to at least one embodiment. As seen in these figures, slender pointed element 22 may be structured to enable fluid communication within flexible catheter 90. More particularly, slender pointed element 22 may be sized to allow for clearance between an exterior surface of slender pointed element 22 and an interior surface (i.e., lumen 94) of flexible catheter 90. For example, in certain embodiments slender pointed element 22 may comprise at least one longitudinally extending indentation 27 defined along at least a portion of the length of slender pointed element 22. In particular, as shown in FIGS. 8C and 8D, slender pointed element 22 may comprise a plurality of longitudinally extending indentations 27 defined along a longitudinal axis 11 of slender pointed element 22. In addition, as seen in the end view of FIG. 8D, longitudinally extending indentations 27 may be defined along the generally circular slender pointed element 22 so as to form a substantially triangular cross section.

Figure 8E:
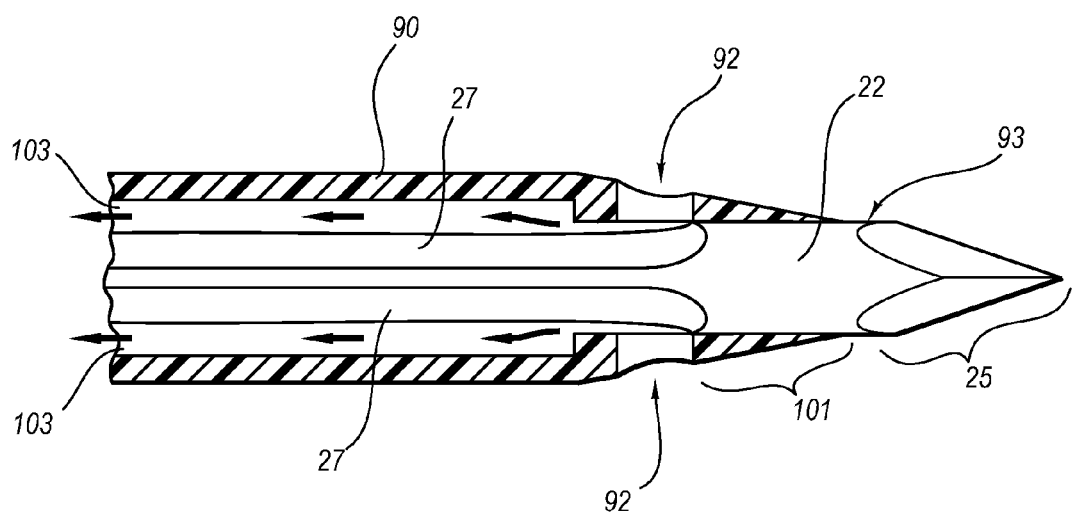
FIG. 8E is a cross-sectional side view of the exemplary slender pointed element illustrated in FIG. 8C positioned within an exemplary flexible catheter.

FIG. 8E is a cross-sectional side view of a slender pointed element 22 positioned within an exemplary flexible catheter 90. As shown in this figure, slender pointed element 22 may be configured such that its pointed end 25 extends from second opening 93 of flexible catheter 90. In addition, as illustrated in FIG. 8E, slender pointed element 22 and flexible catheter 90 may be sized such that, when slender pointed element 22 is fully inserted within flexible catheter 90, the exterior surface of slender pointed element 22 snugly fits within and contacts the interior surface of flexible catheter within region 101. In certain embodiments, longitudinally extending indentations 27 may be sized and positioned to provide a fluid communication path between apertures 92 and first opening 91 of flexible catheter 90. In other words, longitudinally extending indentations 27 may provide a fluid communication path within an annulus 103 defined by the exterior surface of slender pointed element 22 and the interior surface (i.e., lumen 94) of flexible catheter 90.

Figure 9A:
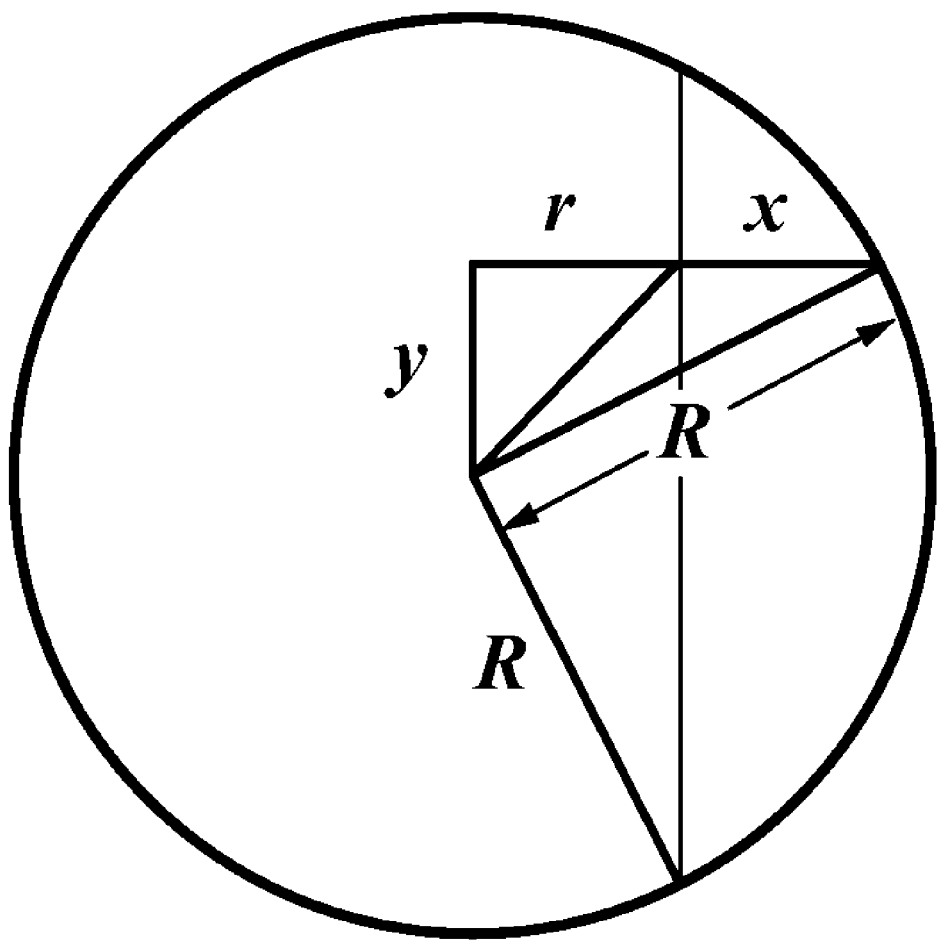
FIG. 9A illustrates various exemplary geometrical attributes of a longitudinally extending indentation defined along a slender pointed element according to at least one embodiment.

FIG. 9A illustrates various exemplary geometrical attributes of a longitudinally extending indentation defined along a slender pointed element according to at least one embodiment. As seen in this figure, the cross-sectional area defined between an exterior surface of slender pointed element 22 and an interior surface of flexible catheter 90 (hereafter, "the total effective cross-sectional area of annulus 103") may be sized so as to approximate the cross-sectional area of a selected hollow needle gauge. For example, the total effective cross-sectional area of annulus 103 may be defined by:

$$A = R^2 \tan^{-1}\left[\sqrt{\left(\frac{R^2}{r}\right) - 1}\right] - r\sqrt{R^2 - r^2}, \quad (1)$$

where, with reference to FIG. 9A, R is the radius of the circle (i.e., an interior surface of cylindrical flexible catheter 90) and r is a perpendicular distance from the center of the circle to the outer circumference of the circle. In contrast, the area of a hollow, cylindrical needle may be defined by:

$$A = \pi\left(\frac{ID}{2}\right)^2, \quad (2)$$

where ID is the diameter of the lumen of the needle.

Figure 9B:
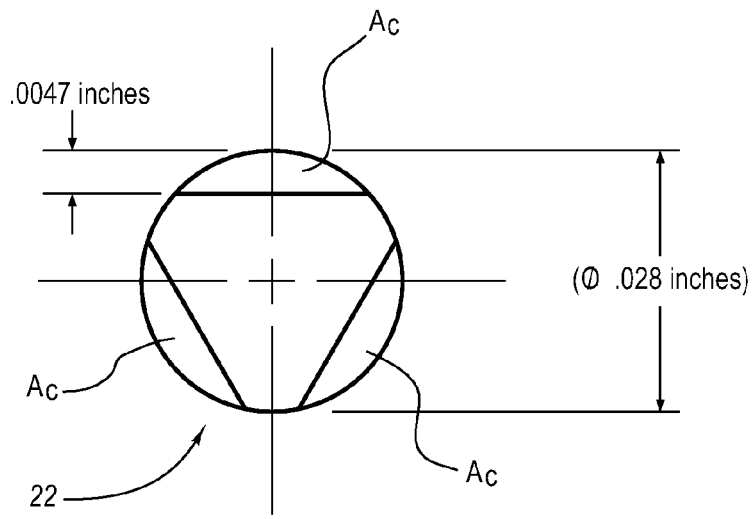
FIG. 9B is a schematic end view of a slender pointed element according to at least one embodiment.
Figure 9C:
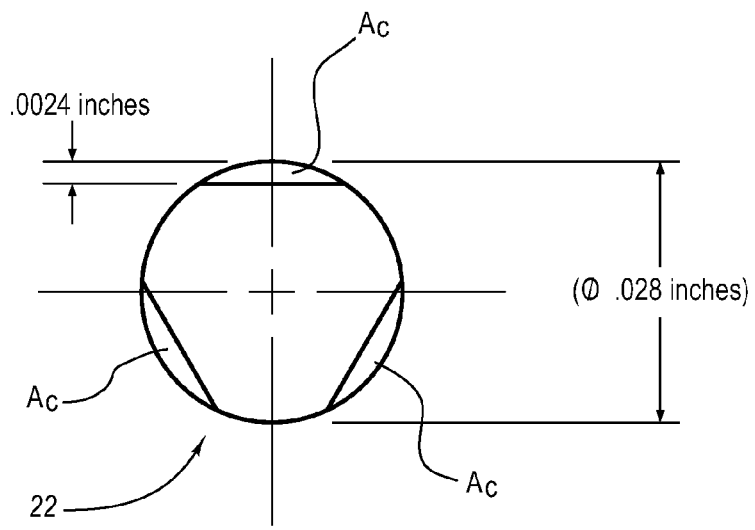
FIG. 9C is a schematic end view of a slender pointed element according to an additional embodiment.

Accordingly, in light of equations (1) and (2), longitudinally extending indentations 27 may be sized such that the total effective cross-sectional area of annulus 103 (represented by reference numeral Ac in FIGS. 9B and 9C) may approximate the cross-sectional area of a selected hollow needle gauge. For example, as illustrated in FIG. 9B, the approximate cross-sectional area of a 22 gauge needle may be approximated by forming three chord-shaped longitudinally extending depressions 27 to a depth of 0.0047 inches within a cylindrical slender pointed element 22 having a diameter of 0.028 inches. Similarly, as illustrated in FIG. 9C, the approximate cross-sectional area of a 25 gauge needle may be approximated by forming three chord-shaped longitudinally extending depressions 27 to a depth of 0.0024 inches within a cylindrical slender pointed element 22 having a diameter of 0.028 inches.

Figure 10A:
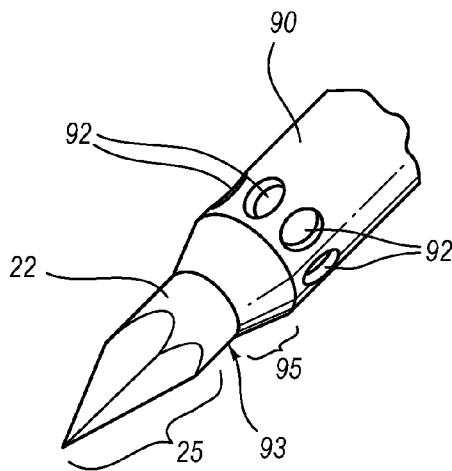
FIGS. 10A-10E are perspective views of various exemplary embodiments of a flexible catheter.
Figure 10B:
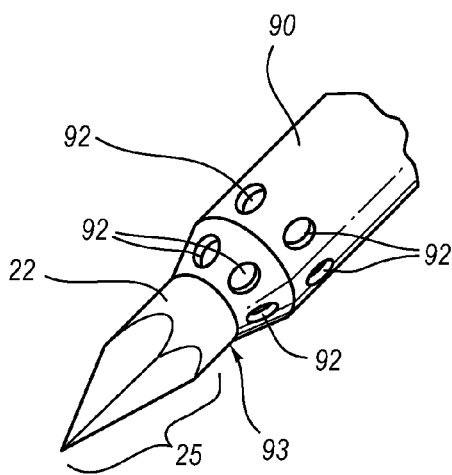
Figure 10C:
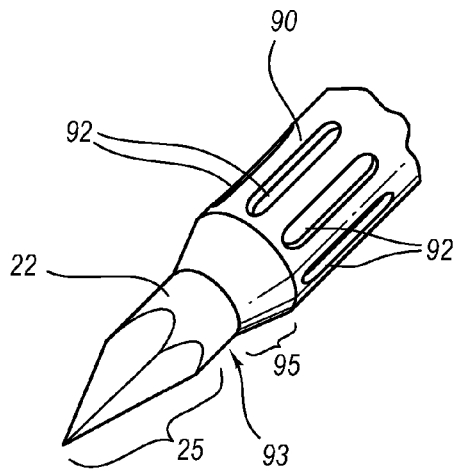
Figure 10D:
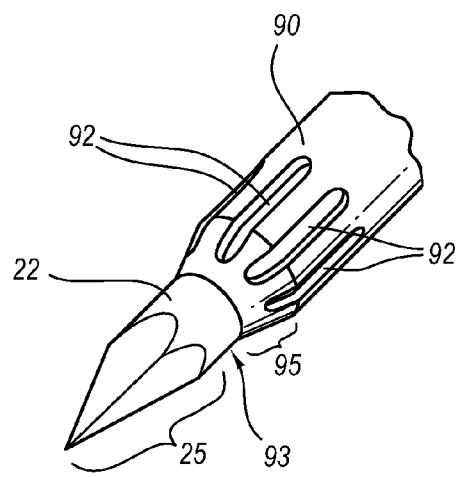
Figure 10E:
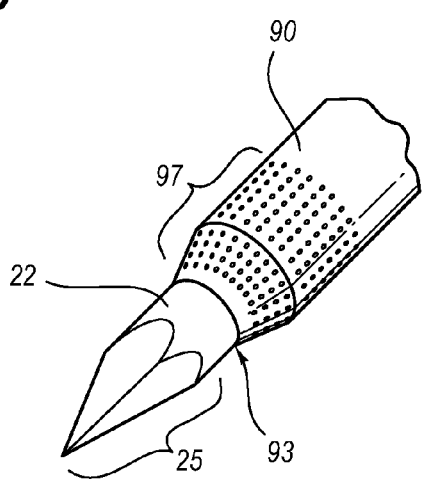

FIGS. 10A-10E are perspective views of various exemplary embodiments of a flexible catheter 90. As illustrated in these figures and as detailed above, one or more apertures 92 may be defined within flexible catheter 90 proximate a second opening 93. More particularly, as illustrated in FIGS. 10A-10D, one or more of apertures 92 may be generally circular, oval, or elongated in shape and may be formed within or proximate to tapered transition region 95. In addition, as illustrated in FIG. 10E, flexible catheter 90 may comprise a permeable region 97 defined proximate second opening 93. In at least one embodiment, permeable region 97 is configured to allow fluids, such as blood, to pass therethrough.

Figure 11A:
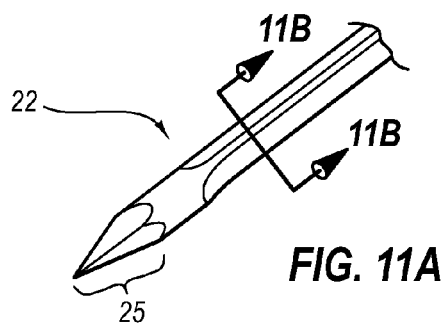
FIG. 11A is a perspective view of an exemplary embodiment of a slender pointed element.
Figure 11B:
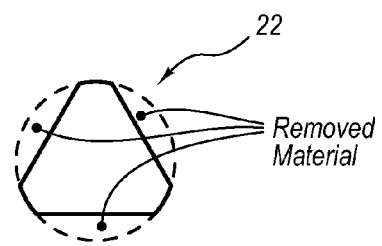
FIG. 11B is a cross-sectional end view of the exemplary slender pointed element illustrated in FIG. 11A, taken along the line 11B-11B.
Figure 11C:
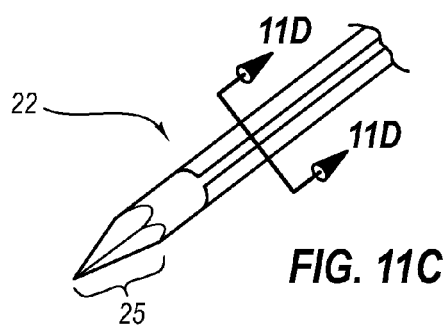
FIG. 11C is a perspective view of an additional embodiment of a slender pointed element.
Figure 11D:
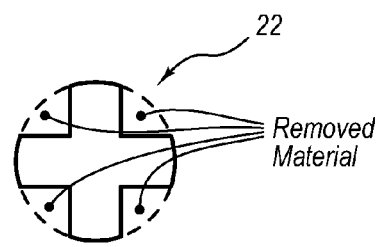
FIG. 11D is a cross-sectional end view of the exemplary slender pointed element illustrated in FIG. 11C, taken along the line 11D-11D.
Figure 11E:
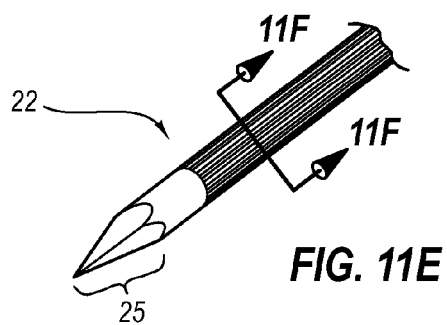
FIG. 11E is a perspective view of an additional embodiment of a slender pointed element.
Figure 11F:
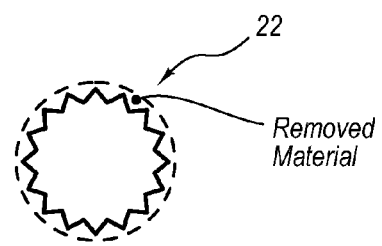
FIG. 11F is a cross-sectional end view of the exemplary slender pointed element illustrated in FIG. 11E, taken along the line 11F-11F.
Figure 11G:
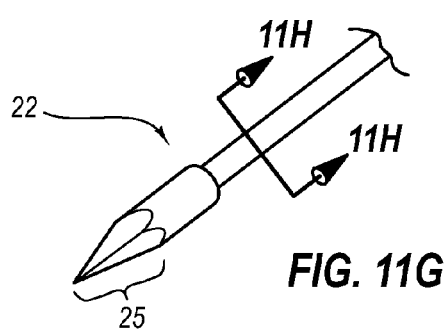
FIG. 11G is a perspective view of an additional embodiment of a slender pointed element.
Figure 11H:
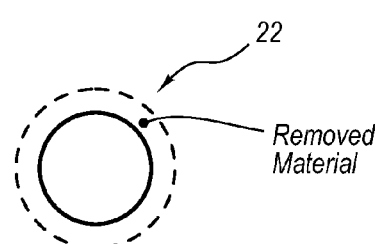
FIG. 11H is a cross-sectional end view of the exemplary slender pointed element illustrated in FIG. 11G, taken along the line 11H-11H.

As illustrated in FIGS. 11A-11H, slender pointed element 22 may be formed in a variety of shapes and configurations. For example, slender pointed element 22 may be formed to have a substantially triangular cross-section (as illustrated in FIG. 11B), a substantially cross-shaped cross-section (as illustrated in FIG. 11D), a substantially star-shaped cross-section (as illustrated in FIG. 11F), and/or a substantially circular cross-section (as illustrated in FIG. 11H). The total effective cross-sectional area of an annulus 103 defined by the interior surface of a flexible catheter 90 and the exterior surface of slender pointed element 22 positioned within the flexible catheter may be varied by varying the cross-sectional shape and size of slender pointed element 22. In other embodiments, flexible catheter 90 may be configured to allow fluid communication between an exterior surface of slender pointed element 22 and an interior surface of flexible catheter 90. In a particular embodiment, there is no need to remove material from slender pointed element 22 to provide fluid communication between the interior surface of flexible catheter 90 and the exterior surface of slender pointed element 22.

Figure 12A:
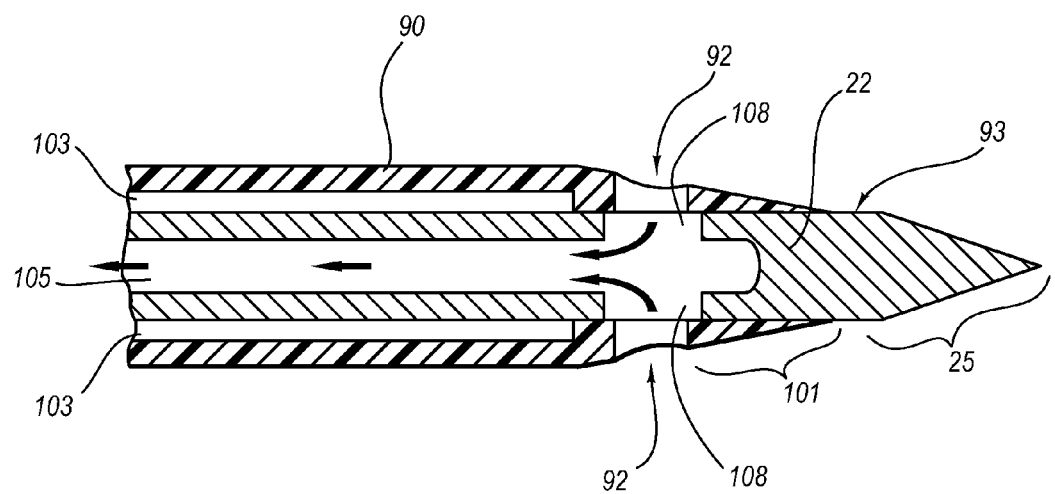
FIG. 12A is a cross-sectional side view of a portion of a slender pointed element and a flexible catheter according to at least one embodiment.
Figure 12B:
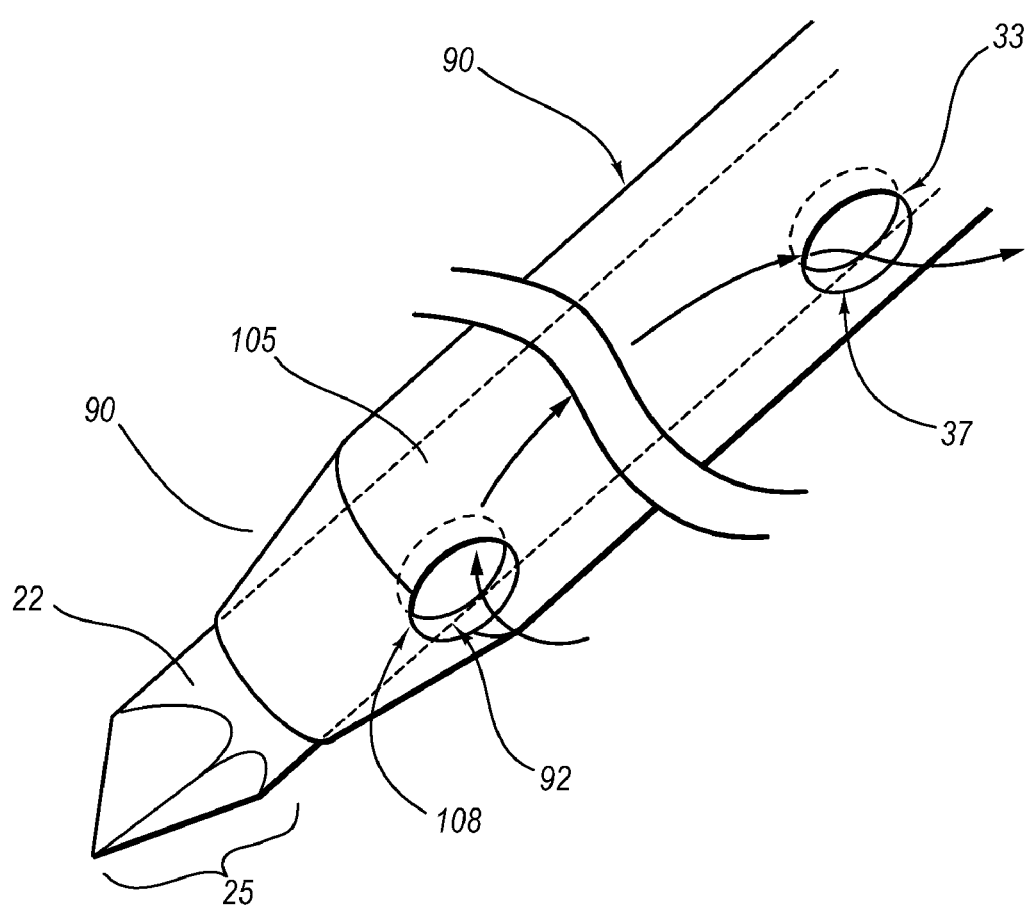
FIG. 12B is a schematic perspective view of the exemplary slender pointed element and flexible catheter illustrated in FIG. 12A.

FIGS. 12A and 12B are cross-sectional and perspective views, respectively, of an additional embodiment of a slender pointed element 22 positioned within an exemplary flexible catheter 90. As illustrated in these figures, slender pointed element 22 may comprise a solid pointed end 25 and a lumen 105 defined within at least a portion of the body of slender pointed element 22. In addition, a plurality of apertures 108 defined within slender pointed element 22 may provide fluid communication between one or more apertures 92 defined through flexible catheter 90 and lumen 105 of slender pointed element 22. In at least one embodiment, fluid may flow through at least one aperture 92 defined through flexible catheter 90 and through a corresponding aperture 108 defined in slender pointed element 22. In such a configuration, annulus 103 may be omitted, if desired.

In certain embodiments, apertures 108 may be defined such that, when insertion assembly 20 is coupled to hub 40, apertures 108 are positioned proximate manifold element 61 of hub 40. In this exemplary configuration, fluid may flow through apertures 92 and 108, into lumen 105, through an aperture 33 defined in slender pointed element 22 and a corresponding aperture 37 defined in flexible catheter 90, through opening 53 of manifold element 61, out of opening 49 of manifold element 49, and into an extension tube, such as extension tube 70. Such a configuration may be desirable for providing a simple and robust fluid communication path between extension tubing 70 and an internal fluid chamber of an implanted device, such as chamber 324 of exemplary access port 320.

Figure 13:
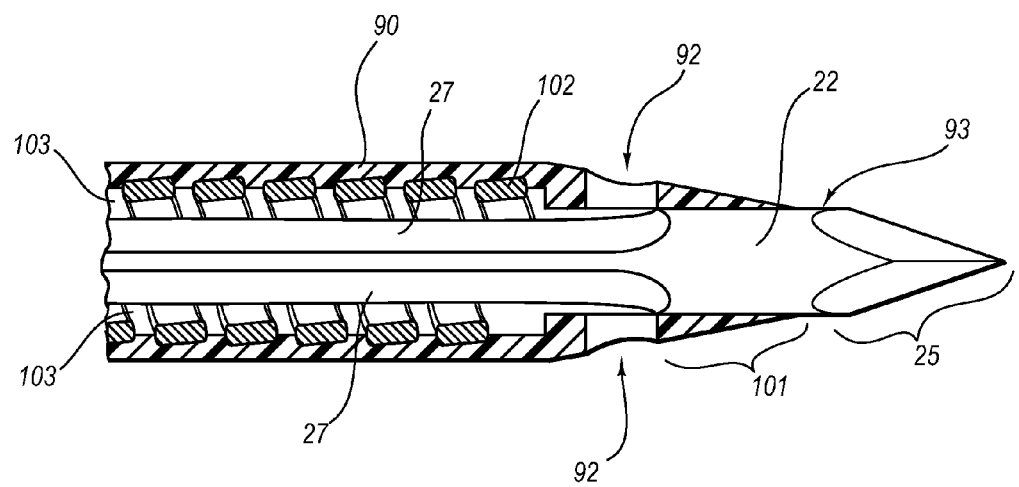
FIG. 13 is a partial cross-sectional side view of an additional embodiment of a flexible catheter.

FIG. 13 is a partial cross-sectional side view of an additional embodiment of a flexible catheter 90. As seen in this figure, flexible catheter 90 may further comprise a reinforcing member 102. In at least one embodiment, reinforcing member 102 may be at least partially imbedded within flexible catheter 90. Reinforcing member 102 may also comprise a coiled, stainless steel wire (formed of, for example, AISI 304 stainless steel) and may have a generally circular, generally oval, rectangular, triangular, or otherwise shaped cross-section. In certain embodiments, reinforcing member 102 may be coiled within flexible catheter 90 to extend in a substantially spiral or helical fashion. Reinforcing member 102 may also be structured for, among other reinforcing functions, resisting external radial forces applied to flexible catheter 90, thereby helping to prevent the inward collapse of flexible catheter 90. In addition, reinforcing member 102 may ameliorate kinking of flexible catheter 90. Reinforcing member 102 may also be sized and positioned within flexible catheter 90 so as to avoid intersecting with apertures 92 defined in flexible catheter. In this exemplary embodiment, apertures 92 may be formed through flexible catheter 90 by drilling or punching out portions of flexible catheter 90, or as otherwise known in the art. Optionally, apertures 92 may be defined through coiled reinforcing member 102 if necessary or desirable.

Figure 14A:
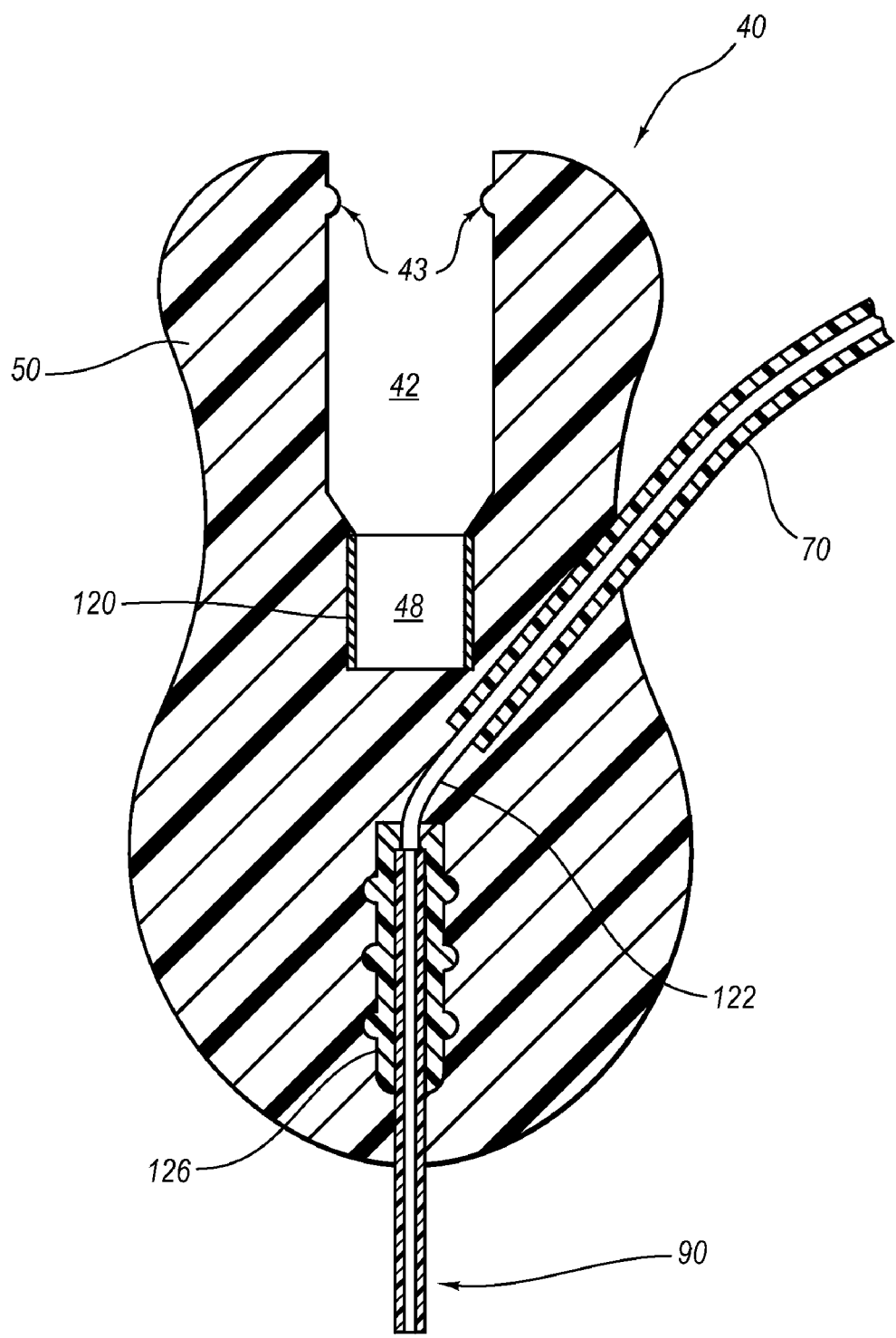
FIG. 14A is a simplified cross-sectional side view of an additional embodiment of a hub.

As will be appreciated by those of ordinary skill in the art, a number of additional insertion assembly embodiments and hub embodiments fall within the spirit and scope of the instant disclosure. For example, as illustrated in the cross-sectional side view of FIG. 14A, hub 40 may be configured to have a substantially pear-shaped cross-section. In this exemplary embodiment, hub 40 may generally comprise a hub body 50, a recess 42 configured to receive a safety clip, and a sleeve 120 positioned about a septum 48. As shown in FIG. 14A, a retaining lip 43 may be provided within recess 42 for retaining a safety clip, such as safety clip 30, therein. An anchor element 126 may also be positioned within and securely affixed to hub body 50. In certain embodiments, flexible catheter 90 may be affixed to anchor element 126 to effectively secure flexible catheter 90 within hub body 50.

In the exemplary embodiment illustrated in FIG. 14A, extension tube 70 may be affixed to and positioned at least partially within hub body 50. A channel 122 may be defined within hub body 50 and structured to extend between the lumen of extension tube 70 and the lumen of flexible catheter 90 to provide a fluid communication path between extension tube 70 and flexible catheter 90. Exemplary sleeve 120 may also be positioned about septum 48 and securely affixed to hub body 50. In at least one embodiment, sleeve 120 compresses septum 48 to help seal the various perforations formed in septum 48 by slender pointed element 22.

Figure 14B:
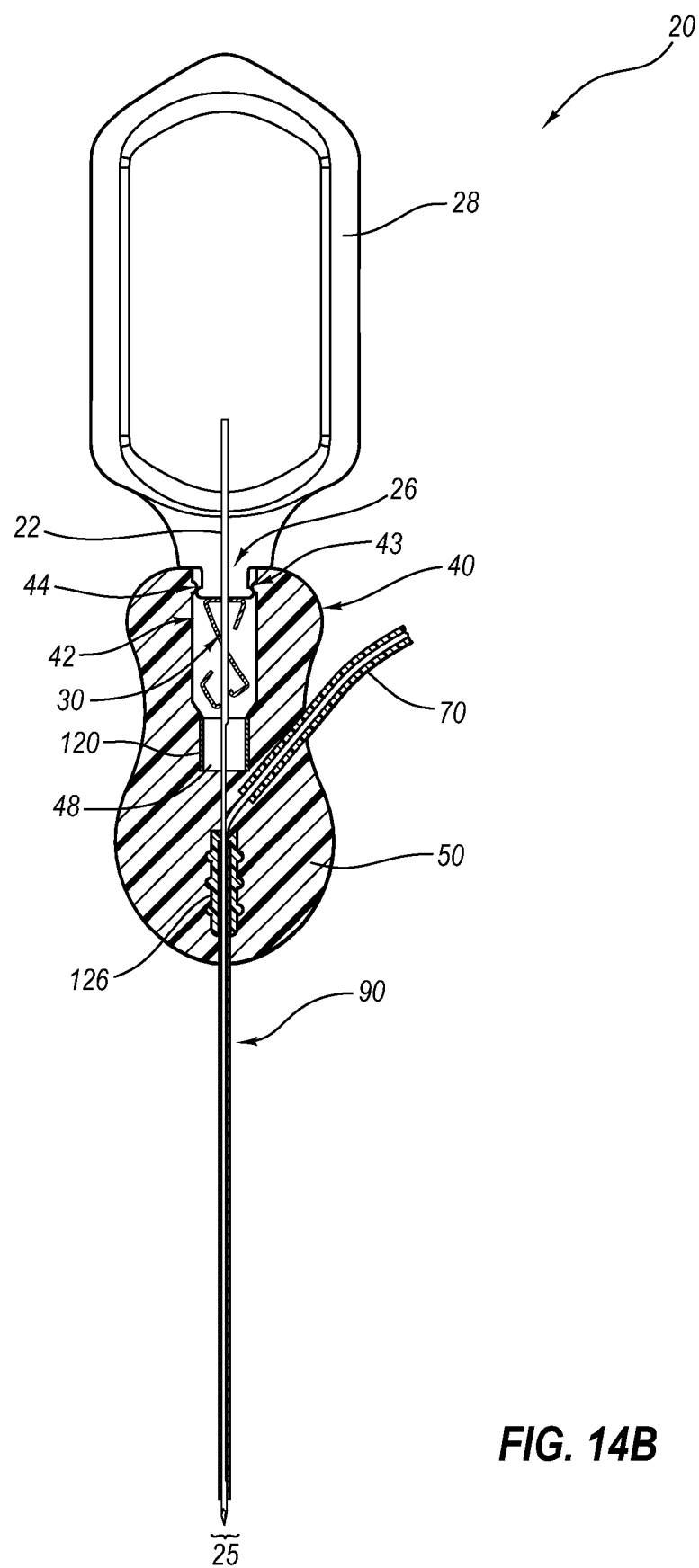
FIG. 14B is a simplified cross-sectional side view of an exemplary insertion assembly positioned within the exemplary hub illustrated in FIG. 14A.

FIG. 14B is a simplified cross-sectional side view of an exemplary insertion assembly 20 positioned within the exemplary hub 40 illustrated in FIG. 14A. As seen in this figure, insertion assembly 20 generally comprises a slender pointed element 22 and a base member 28 configured in accordance with one or more of the exemplary embodiments described and/or illustrated herein. In certain embodiments, insertion assembly 20 may be coupled to hub 40 via a coupling structure 26, a coupling recess 44, and a retaining lip 43.

Figure 15:
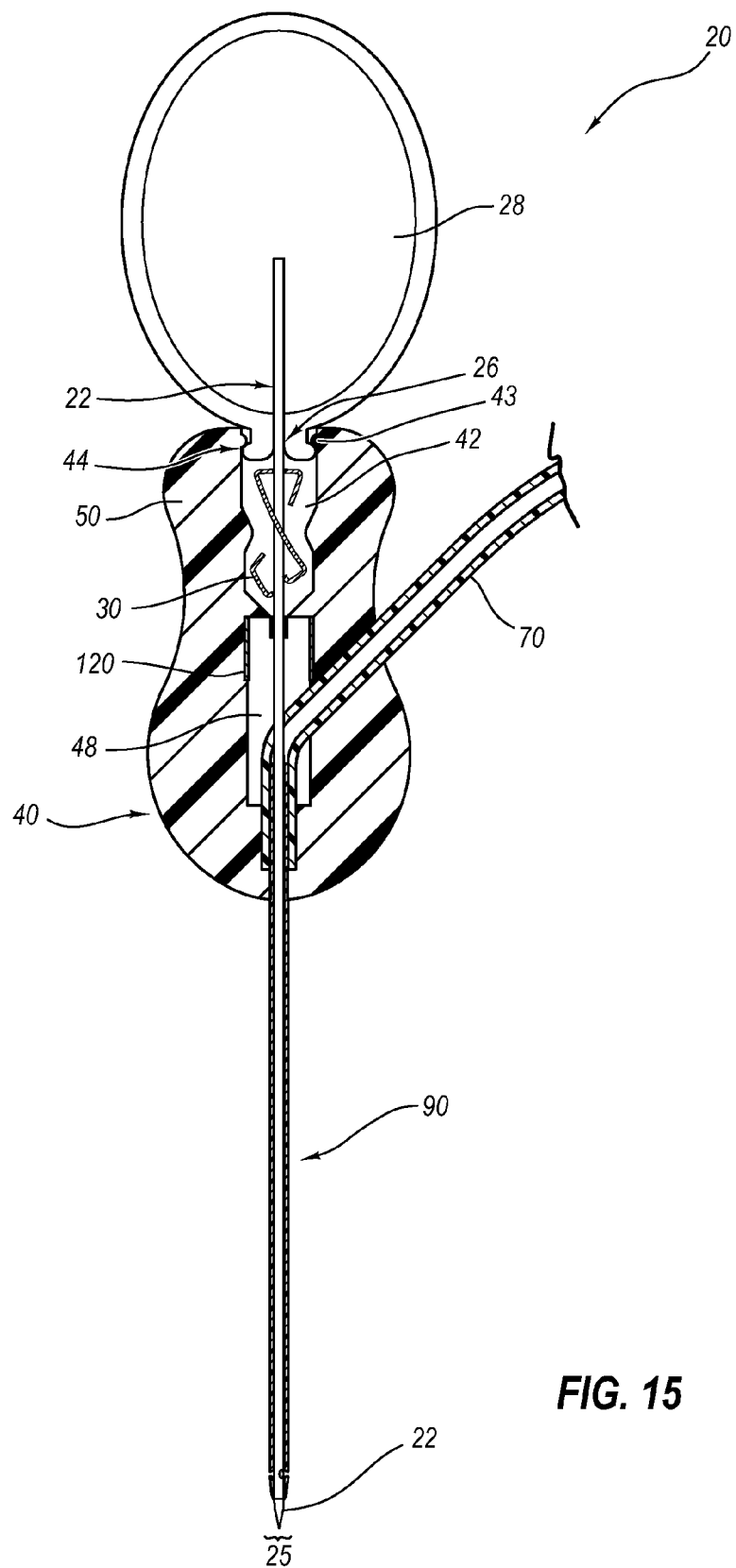
FIG. 15 is a simplified cross-sectional side view of an additional embodiment of an infusion system.

FIG. 15 is a simplified cross-sectional side view of an additional embodiment of an infusion system 10 comprising an insertion assembly 20, a hub 40, a flexible catheter 90, and an extension tube 70. As with previous embodiments, hub 40 may comprise a recess 42, a sleeve 120, and a septum 48. In certain embodiments, at least a portion of both extension tube 70 and flexible catheter 90 may extend within hub body 50. In addition, as illustrated in FIG. 15, at least a portion of flexible catheter 90 may extend within extension tube 70. In other words, extension tube 70 may be configured to receive and surround at least a portion of flexible catheter 90. Accordingly, when insertion assembly 20 is fully inserted within and coupled to hub 40, slender pointed element 22 may penetrate and pass through flexible catheter 90, extension tube 70, or both, as illustrated in FIG. 15. As with previous embodiments, sleeve 120 may compress septum 48 to aid in sealing septum 48 upon removal of slender pointed element 22 from flexible catheter 90 and/or extension tube 70. In an optional embodiment, a single tubular element may extend through hub 40 and function as both flexible catheter 90 and extension tube 70.

Figure 16:
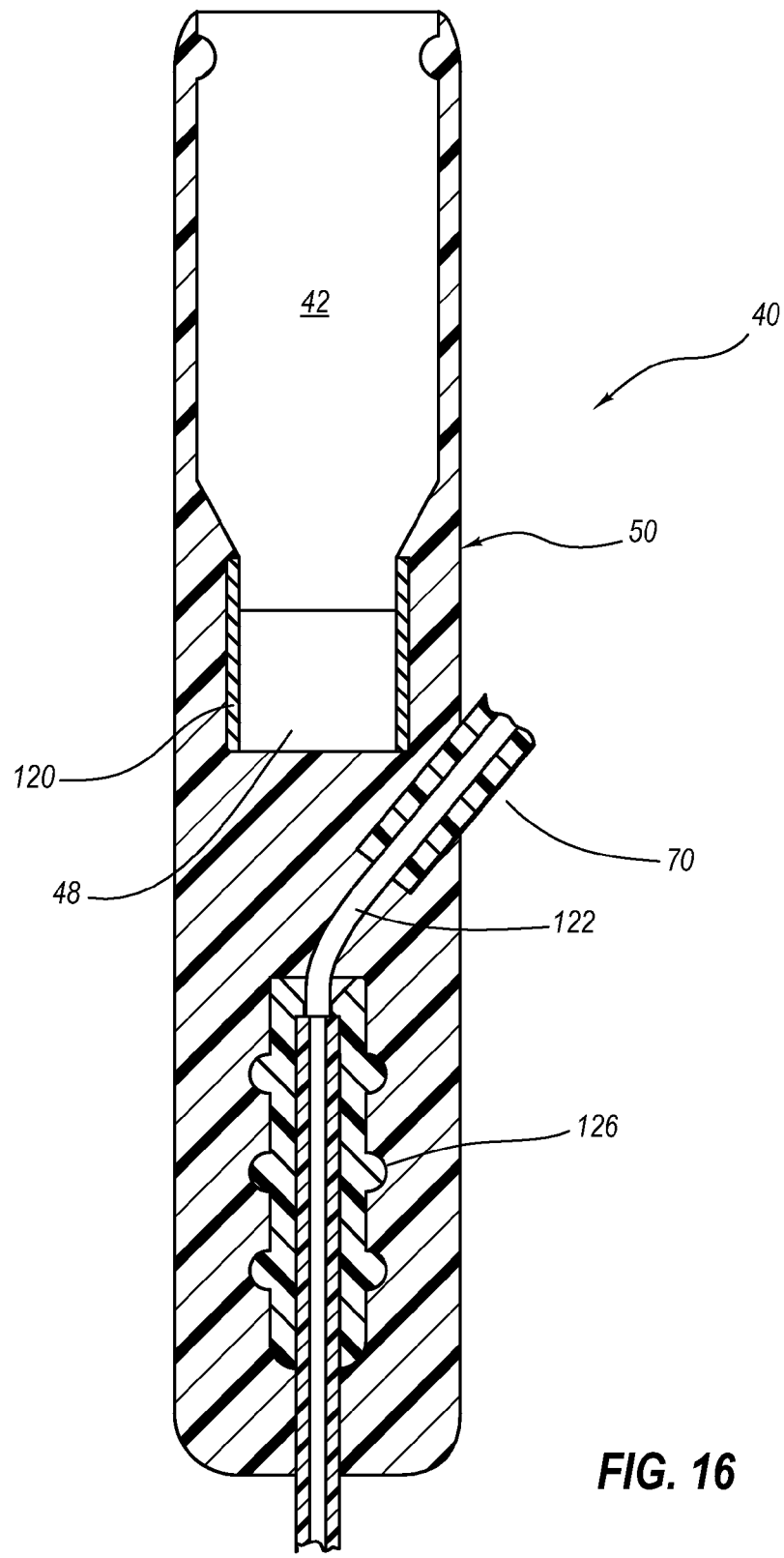
FIG. 16 is a simplified cross-sectional side view of an additional embodiment of a hub.
Figure 19A:
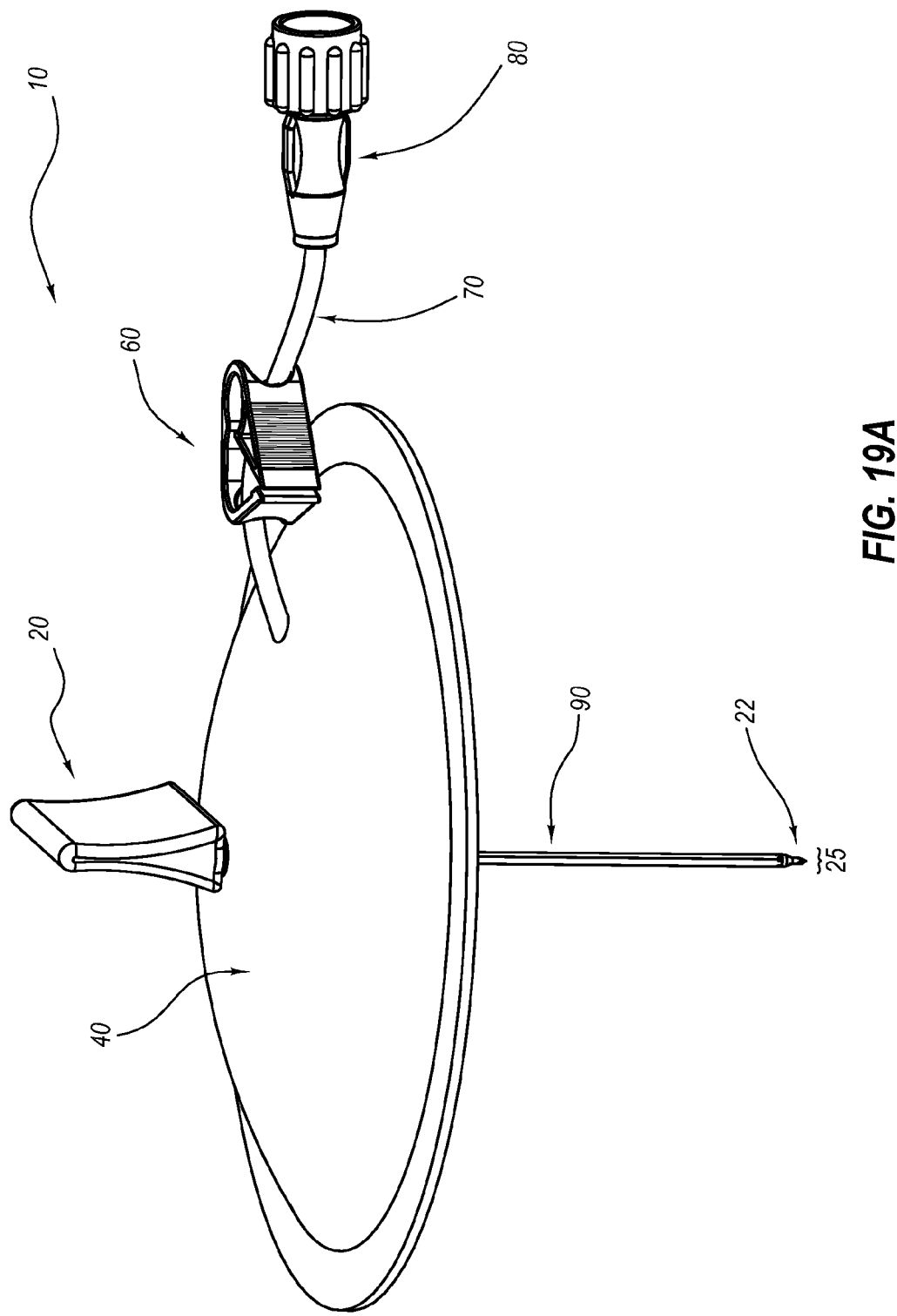
FIG. 19A is a perspective view of an additional embodiment of an infusion system.
Figure 19B:
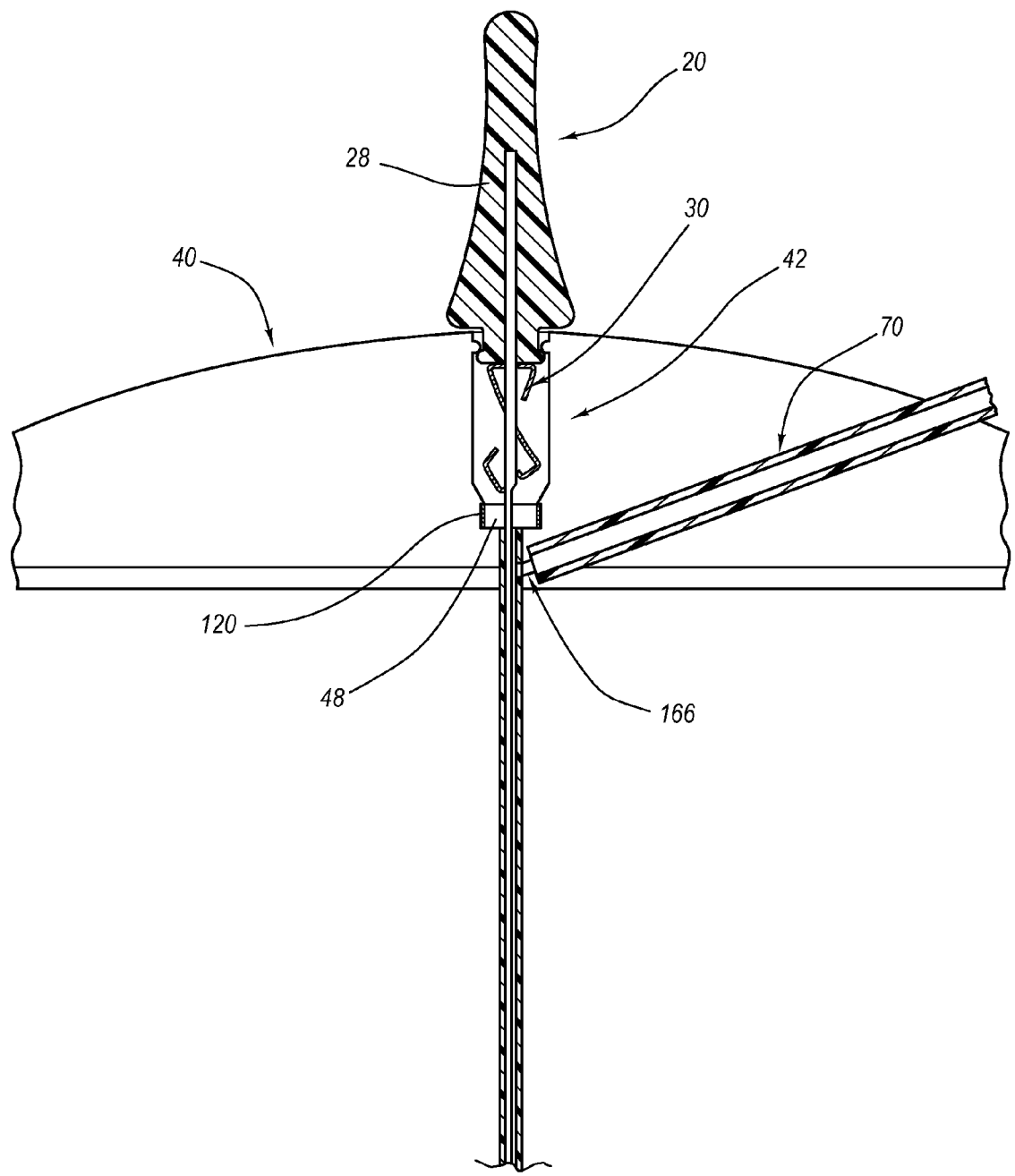
FIG. 19B is a cross-sectional side view of the exemplary infusion system illustrated in FIG. 19A.
Figure 19C:
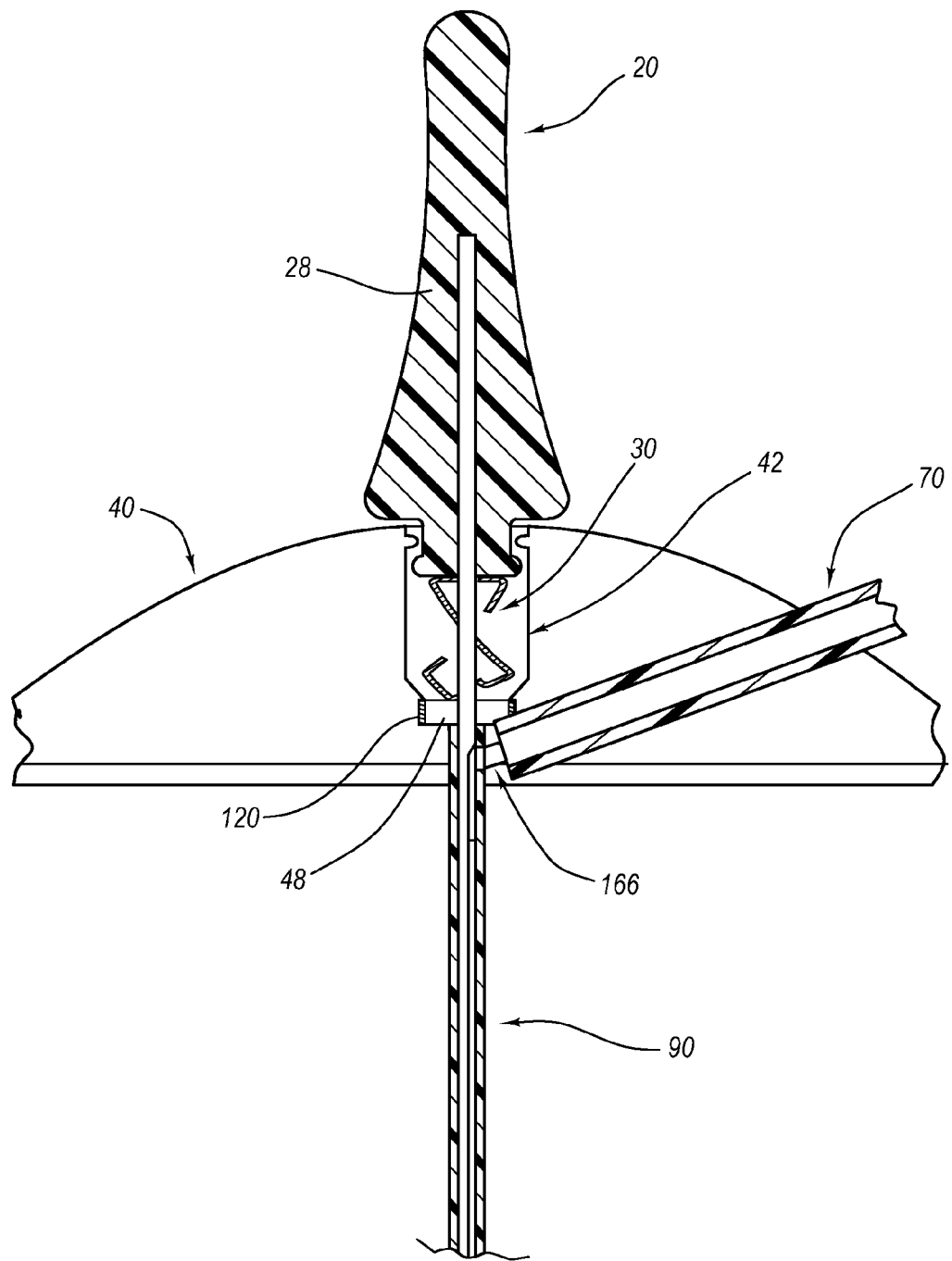
FIG. 19C is a cross-sectional side view of an additional embodiment of an infusion system.

As will be appreciated by those of ordinary skill in the art, hub 40 may be formed in any number of shapes and sizes. For example, hub 40 may be substantially cylindrical in shape (as illustrated in FIG. 16), substantially dome-shaped (as illustrated in FIGS. 19A-19C), substantially wing-shaped (as illustrated in FIGS. 20A-20B and 21A-21E), substantially rectangular or square-shaped (as illustrated in FIGS. 22A-22B and 25A-25B), substantially oblong or oval-shaped (as illustrated in FIGS. 26A-26C, 27A-27B, and 33A-33C), or formed in any other number of suitable shapes and sizes. As will be appreciated by those of skill in the art, the various possible shapes and configurations of hub 40 and insertion assembly 20 may provide various advantages, such as ease of handling by a user and/or compatibility with additional structures.

Figure 17A:
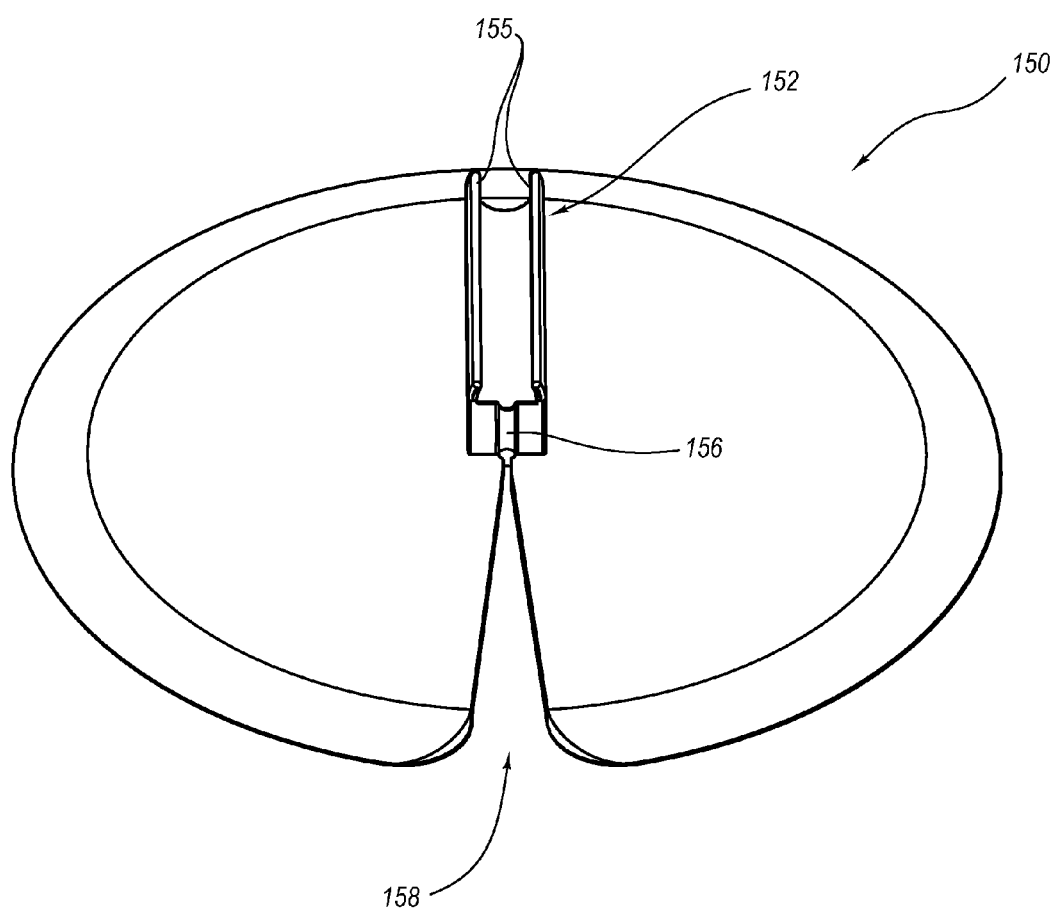
FIG. 17A is a perspective view of an exemplary embodiment of a receiving enclosure for use with an infusion system.
Figure 17B:
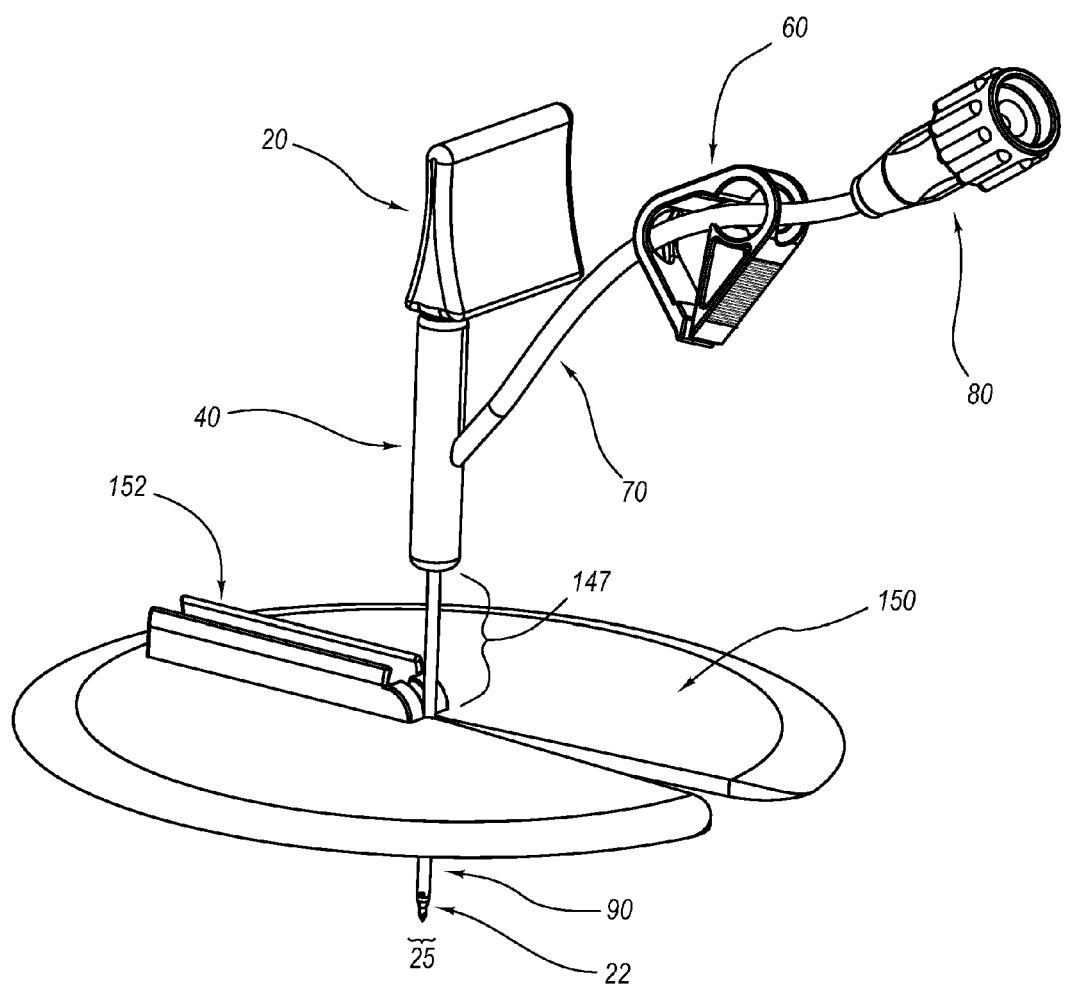
FIG. 17B is a perspective view of an exemplary infusion system positioned within the exemplary receiving enclosure illustrated in FIG. 17A.

FIGS. 17A and 17B are perspective views of an additional embodiment of an infusion system. As illustrated in these figures, this exemplary infusion system may comprise an insertion assembly 20, a hub 40, a flexible catheter 90, an extension tube 70, a clamp 60, and a tube connector 80. In at least one embodiment, the exemplary infusion system illustrated in these figures further comprises a pad member 150 comprising a receiving enclosure 152 configured to receive and at least partially enclose hub 40. More particularly, receiving enclosure 152 may comprise a pair of opposing retaining walls 155 sized and configured to receive and at least partially enclose a hub, such as hub 40 in FIG. 17B. Receiving enclosure 152 may also comprise a rounded channel 156 structured and sized to receive at least a portion of flexible catheter 90. In certain embodiments, rounded channel 156 may aid in ameliorating kinking of extension tube 70 or flexible catheter 90 by preventing sharp bends of flexible catheter 90. Pad member 150 may also comprise an access notch 158 for positioning pad member 150 about flexible catheter 90.

In at least one embodiment, flexible catheter 90 may have a length that exceeds an anticipated insertion length such that, when flexible catheter 90 is fully inserted into a device (such as exemplary access port 320) implanted within a patient, a bendable portion 147 of flexible catheter 90 extends from a skin surface of the patient. More specifically, the length of flexible catheter 90 may be selected such that a portion 147 of the flexible catheter 90 extending outwardly from the skin surface of a patient (such as skin surface 310 illustrated in FIG. 1) may be bent or curved. This exemplary configuration may provide an infusion system that facilitates favorable placement of a hub. For example, after insertion into a device implanted within a patient and upon removal of insertion assembly 20, flexible catheter 90 may be bent so that hub 40 may lie against the surface of the skin or may be otherwise positioned as desired. In the exemplary embodiment illustrated in FIGS. 17A-17B, flexible catheter 90 may be bent to allow hub 40 to be positioned within receiving enclosure 152. Pad 150 may then placed on and/or affixed or taped to the skin surface of a patient. The exemplary infusion system illustrated in FIG. 17B thus represents a relatively low profile apparatus for accessing an implanted device.

Figure 18A:
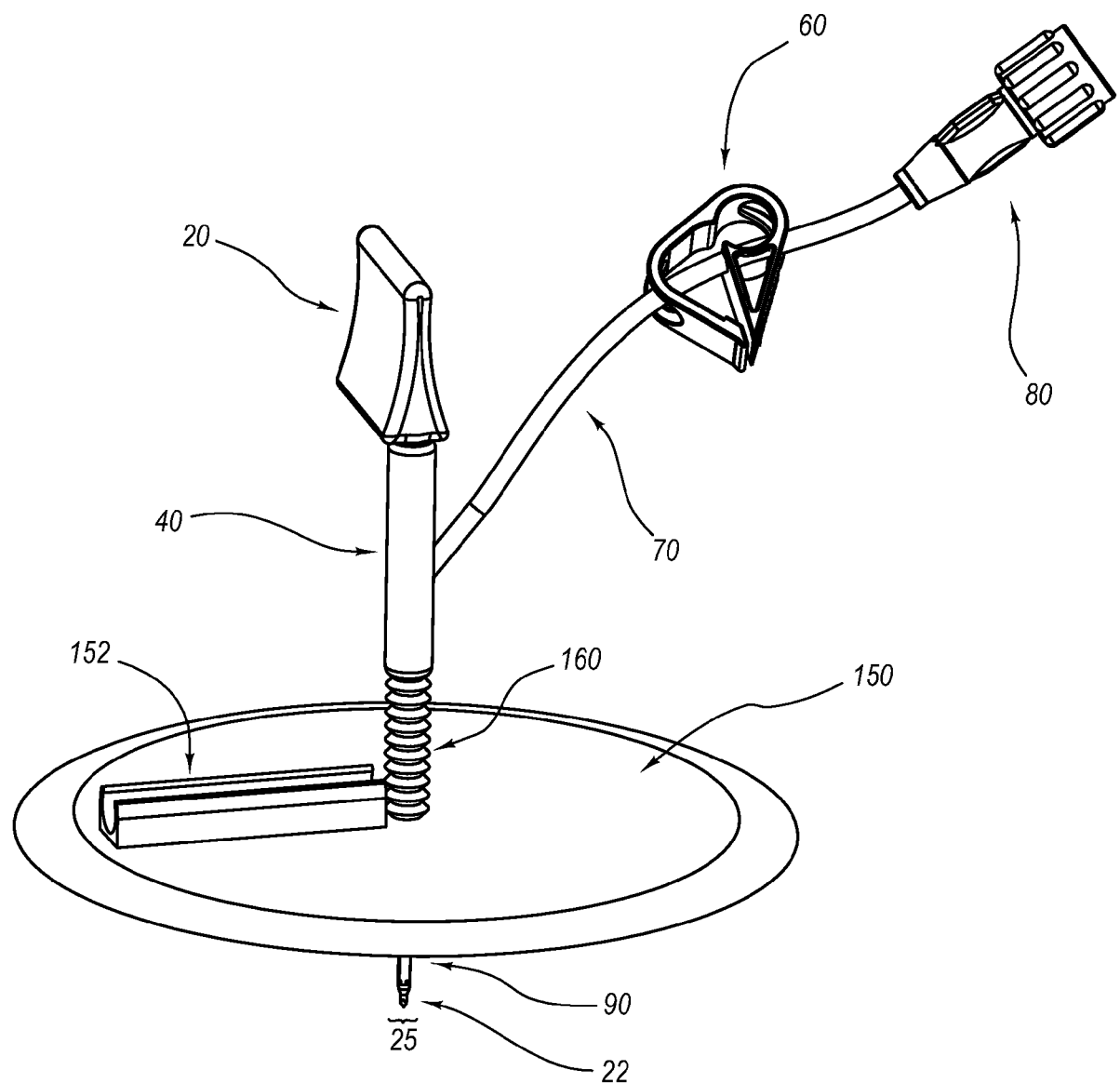
FIG. 18A is a perspective view of an additional embodiment of an infusion system.
Figure 18B:
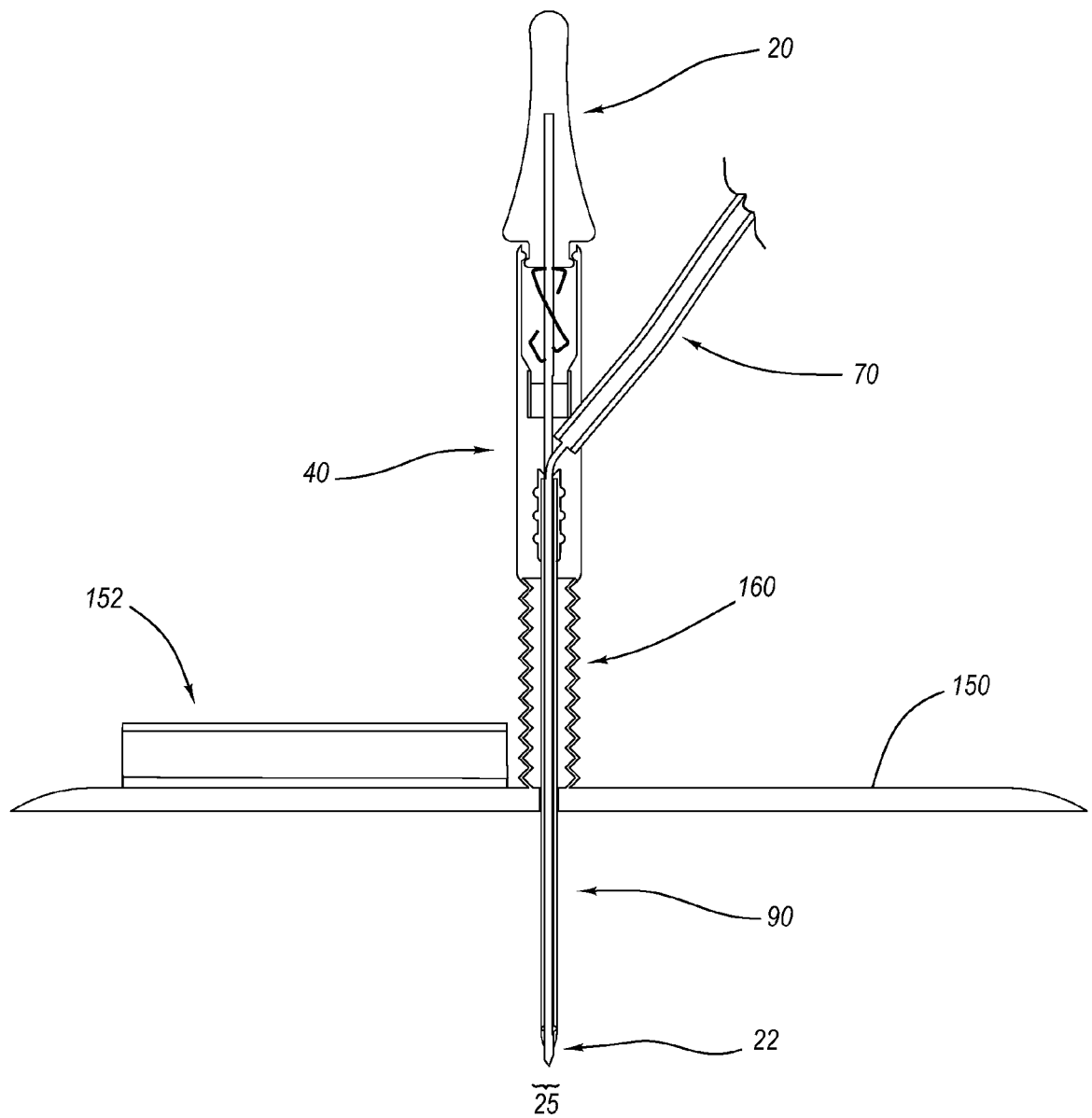
FIG. 18B is a cross-sectional side view of the exemplary infusion system illustrated in FIG. 18A.

As will be appreciated by those of skill in the art, pad member 150 may comprise a receiving enclosure that is configured to accept and retain a hub (of any geometry), an extension tube, a flexible catheter, or combinations thereof, without limitation. In addition, as illustrated in FIGS. 18A and 18B, a sleeve member 160 may surround at least a portion of flexible catheter 90. In particular, as illustrated in FIGS. 18A and 18B, sleeve member 160 may be configured to surround the portion of flexible catheter 90 that extends between hub 40 and pad member 150. In certain embodiments, sleeve member 160 may be folded or creased (e.g., with accordion-type folds) to permit the vertical movement of hub 40 relative to pad member 150. As will be appreciated by those of skill in the art, sleeve member 160 may protect flexible catheter 90, conceal blood traveling through flexible catheter 90 (if flexible catheter 90 is at least partially transparent), or ameliorate kinking of flexible catheter 90.

FIGS. 19A and 19B are perspective and cross-sectional side views, respectively, of an additional embodiment of an infusion system 10 comprising an insertion assembly 20, a hub 40, a flexible catheter 90, an extension tube 70, a clamp 60, and a tube connector 80. As illustrated in these figures, hub 40 may comprise a recess 42 defined within a hub body 50 and a sleeve 120 surrounding a septum 48 positioned within recess 42. In at least one embodiment, fluid communication between extension tube 70 and flexible catheter 90 is provided through a channel 166 formed within hub body 50. In certain embodiments, channel 166 may be formed after flexible catheter 90 and extension tube 70 have been affixed or molded within hub body 50. For example, a machine tool, such as a drill bit or milling bit, may pass within extension tube 70, through a portion of hub body 50, and into flexible catheter 90 to form channel 166 and an aperture in flexible catheter 90. In an additional embodiment, a displacement may be positioned within extension tube 70 and into a preformed aperture in flexible catheter 90, and then hub body 50 may be formed or molded around the assembly.

FIG. 19C is a cross-sectional side view of an additional embodiment of an infusion system. As illustrated in this figure, the vertical (i.e., along the axis of slender pointed element 22) height of hub 40 may be reduced by reducing the vertical height of recess 42 and safety clip 30. As will be appreciated by those of skill in the art, the size and configuration of each component of each exemplary embodiment described and/or illustrated herein may be varied, modified, or otherwise selected, without limitation.

Figure 20A:
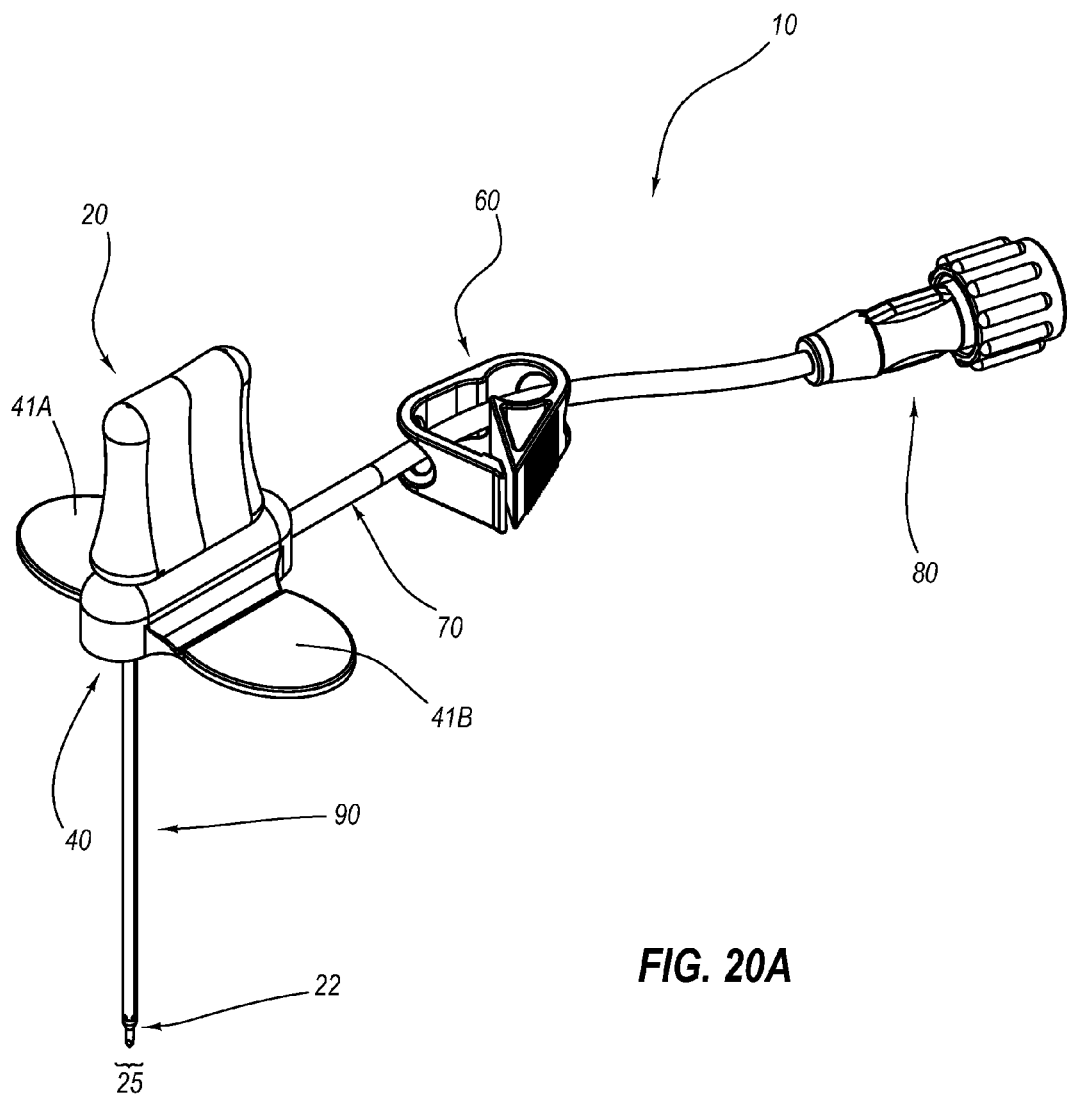
FIG. 20A is a perspective view of an additional embodiment of an infusion system.
Figure 20B:
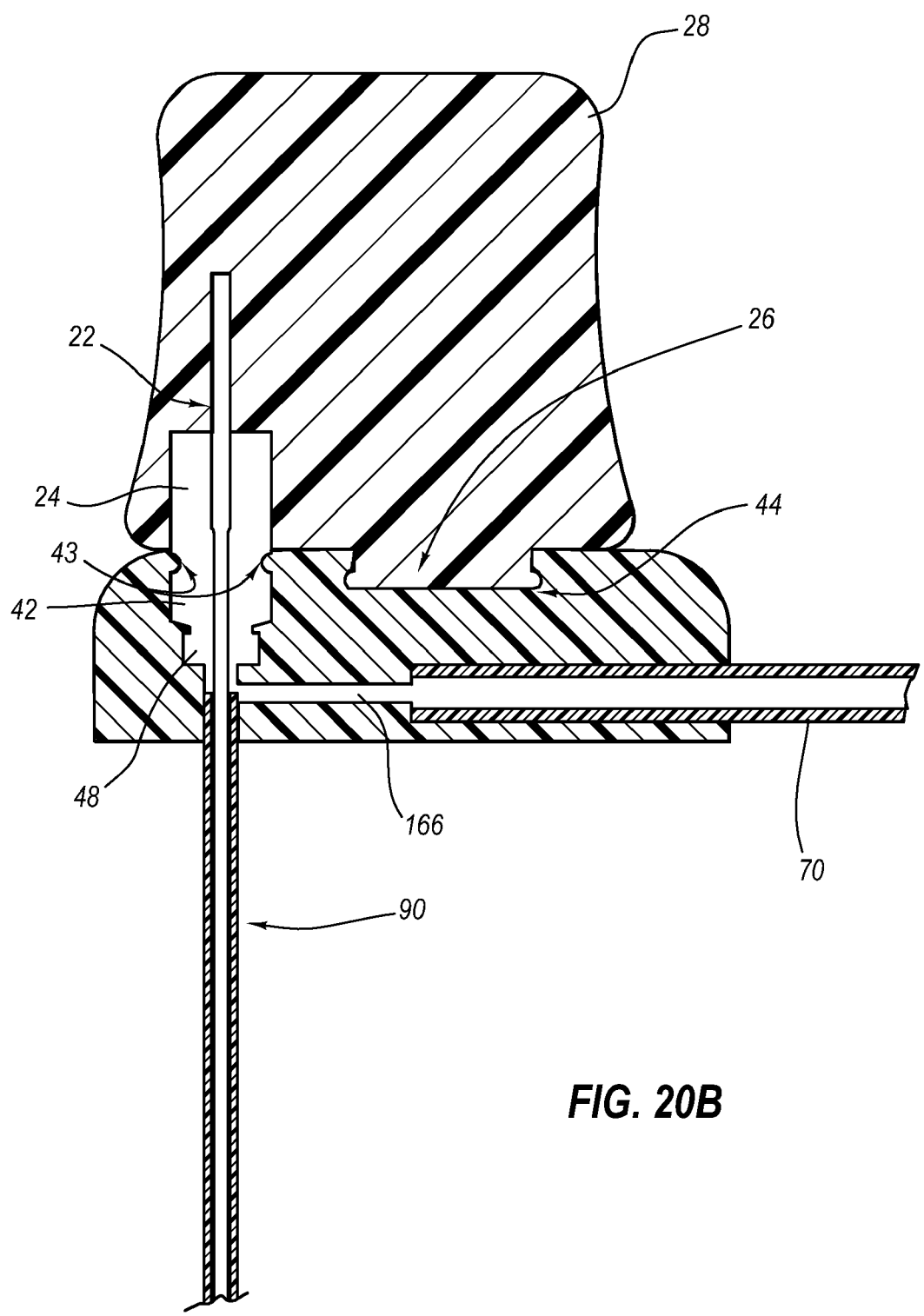
FIG. 20B is a cross-sectional side view of the exemplary infusion system illustrated in FIG. 20A.

FIGS. 20A-20B are perspective and cross-sectional side views, respectively, of an additional embodiment of an infusion system 10 comprising an insertion assembly 20, a hub 40, a flexible catheter 90, an extension tube 70, a clamp 60, and a tube connector 80. As with previous embodiments, hub 40 may generally comprise a hub body 50, a manifold element 61, and a septum 48 compressed by hub body 50 (thus eliminating the need for a sleeve, such as sleeve 120). Hub 40 may also comprise a plurality of wing structures 41A and 41B configured to affix hub 40 to the skin of a patient. In addition, hub 40 may comprise a coupling recess 44 configured to receive a complimentary coupling structure 26 provided on base member 28 of insertion assembly 20. Hub 40 may also comprise a recess 42 having a retaining lip 43 for retaining at least a portion of a safety clip, such as safety clip 30, within recess 42. A channel 166 extending from extension tube 70 to an upper end of flexible catheter 90 may also be defined within hub body 50 for providing fluid communication between extension tube 70 and flexible catheter 90.

Figure 21A:
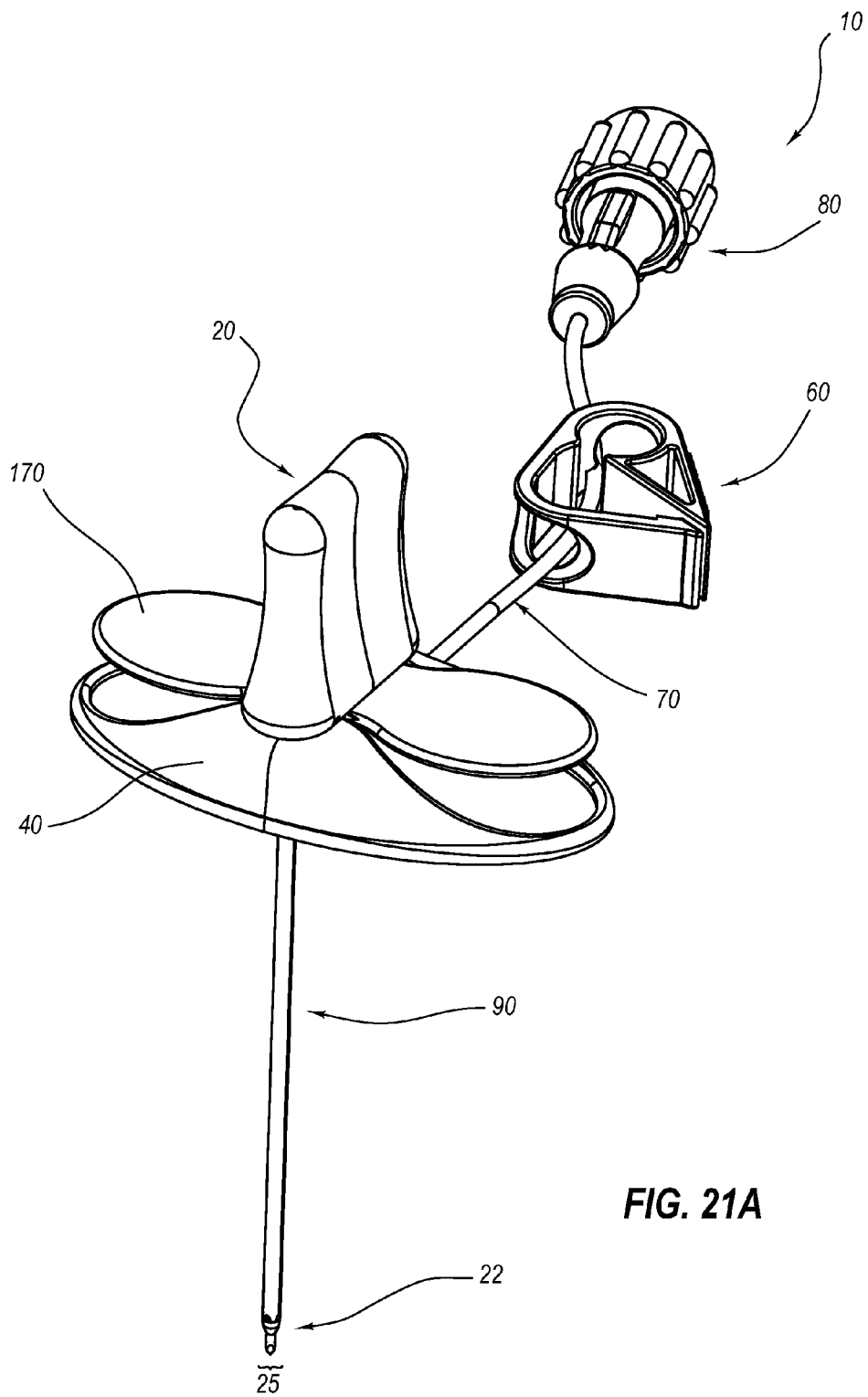
FIG. 21A is a perspective view of an additional embodiment of an infusion system.
Figure 21B:
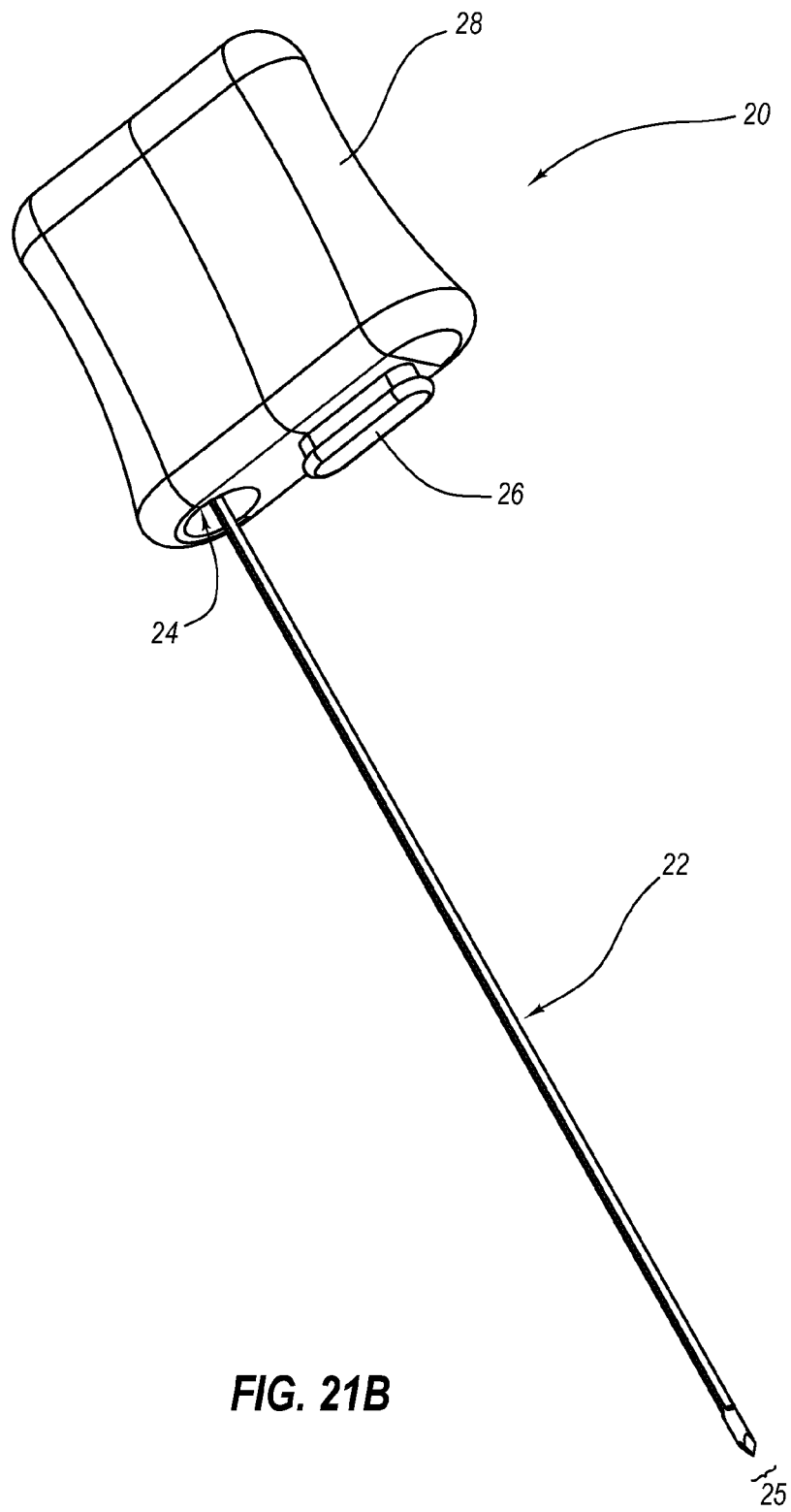
FIG. 21B is a perspective view of a portion of the exemplary infusion system illustrated in FIG. 21A.
Figure 21C:
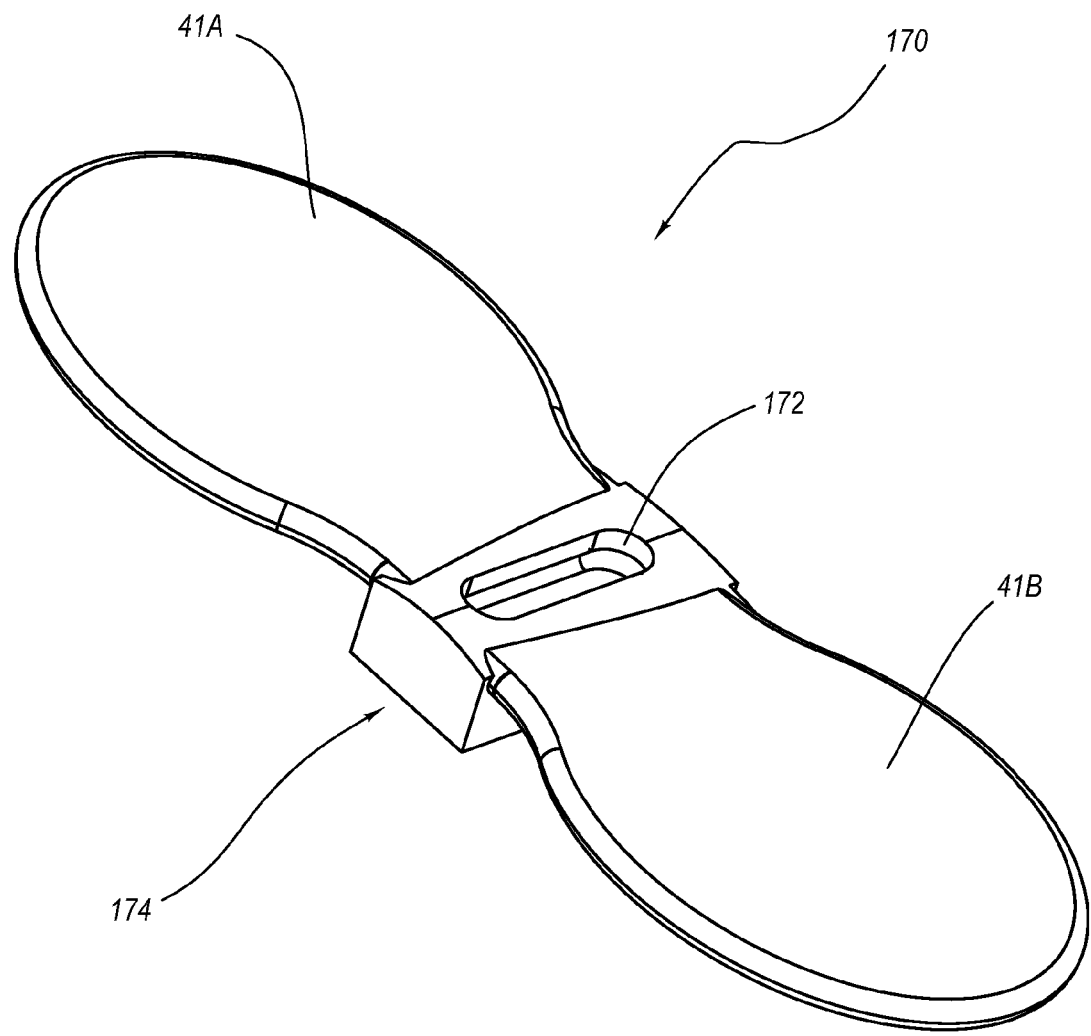
FIG. 21C is a perspective view of a portion of the exemplary infusion system illustrated in FIG. 21A.
Figure 21D:
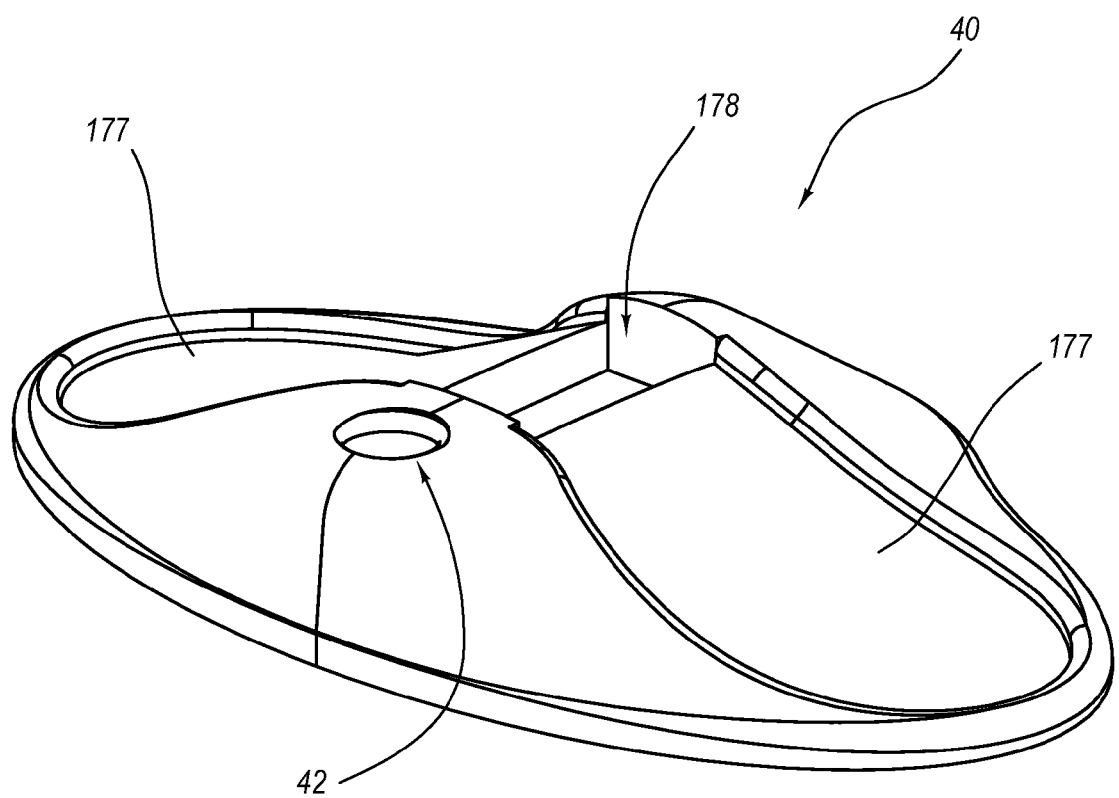
FIG. 21D is a perspective view of a portion of the exemplary infusion system illustrated in FIG. 21A.
Figure 21E:
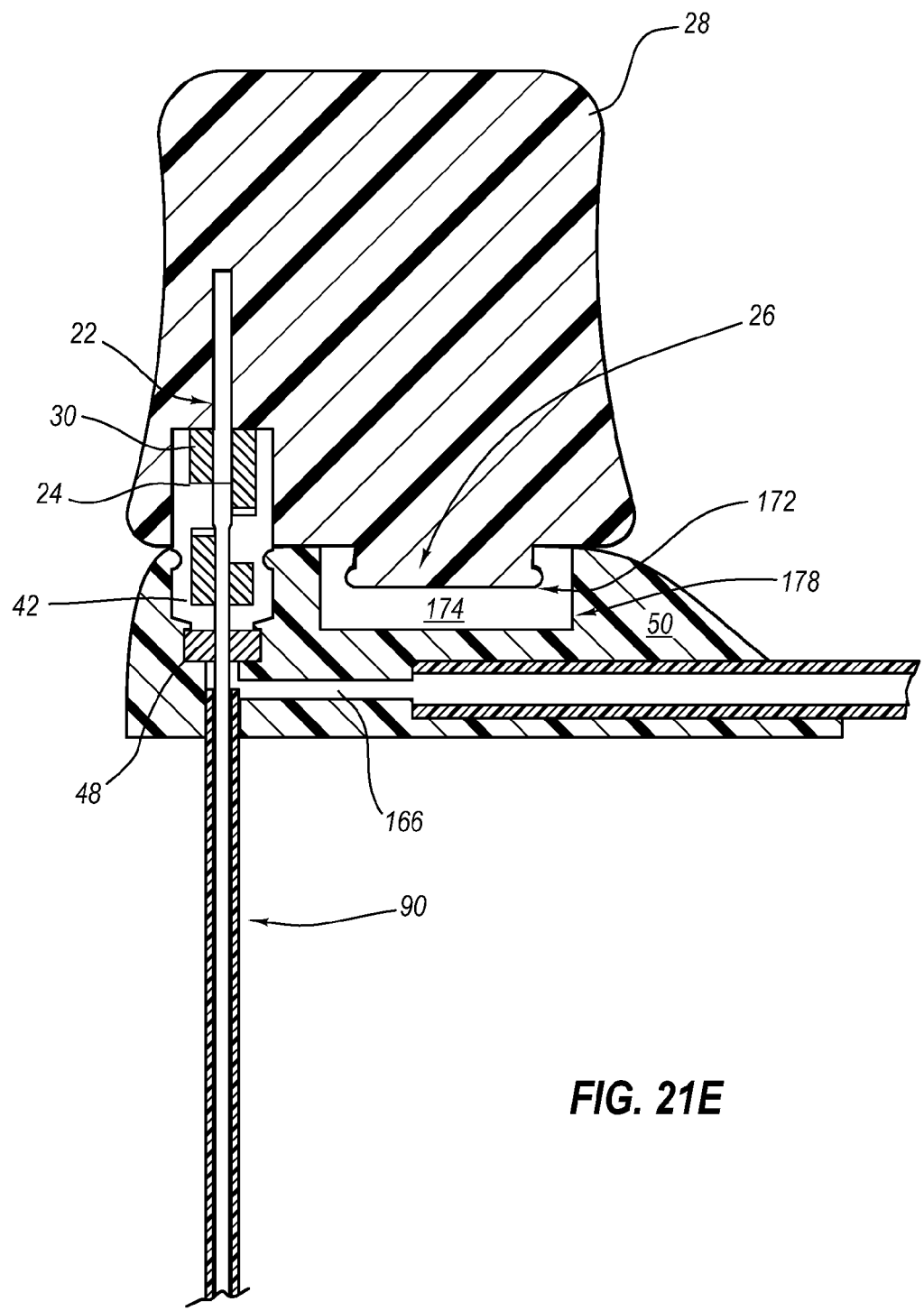
FIG. 21E is a cross-sectional side view of the exemplary infusion system illustrated in FIG. 21A.

FIGS. 21A-21E are perspective and cross-sectional views of various exemplary components of an additional embodiment of an infusion system 10. As seen in FIG. 21A, exemplary infusion system 10 may comprise an insertion assembly 20, a hub 40, a flexible catheter 90, an extension tube 70, a clamp 60, and a tube connector 80. In at least one embodiment, infusion system 10 may also comprise a winged component 170 positioned between insertion assembly 20 and hub 40. As shown in FIG. 21C, winged component 170 may comprise a coupling recess 172 defined within a body 174. A plurality of wing structures 41A and 41B may extend from body 174, as shown in FIG. 21C. In certain embodiments, coupling recess 172 may be configured to receive a complimentary coupling structure 26 provided on a base member 28 of insertion assembly 20. Similarly, as illustrated in FIG. 21D, hub 40 may comprise an opening 178 for accepting the body 174 of winged component 170. Hub 40 may also comprise a recess 42 and wing-shaped depressions 177 for accepting wing structures 41A and 41B of winged component 170. In general, winged component 170 may be affixed to hub 40 by any means known to those of skill in the art, including, for example, by adhering body 174 within opening 178 of hub 40 using an adhesive.

Figure 22A:
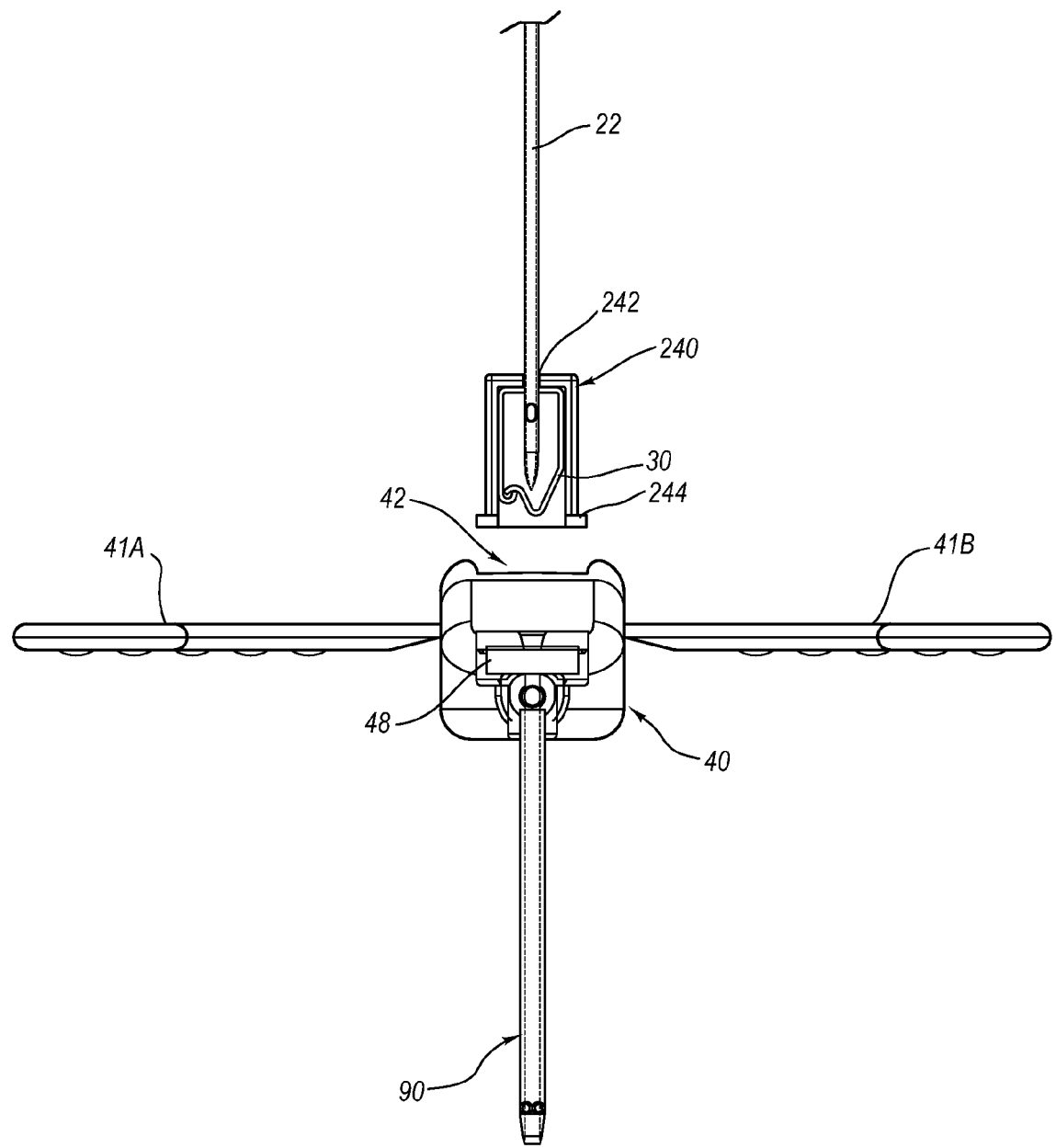
FIG. 22A is a cross-sectional side view of an exemplary safety clip housing in a first position.
Figure 22B:
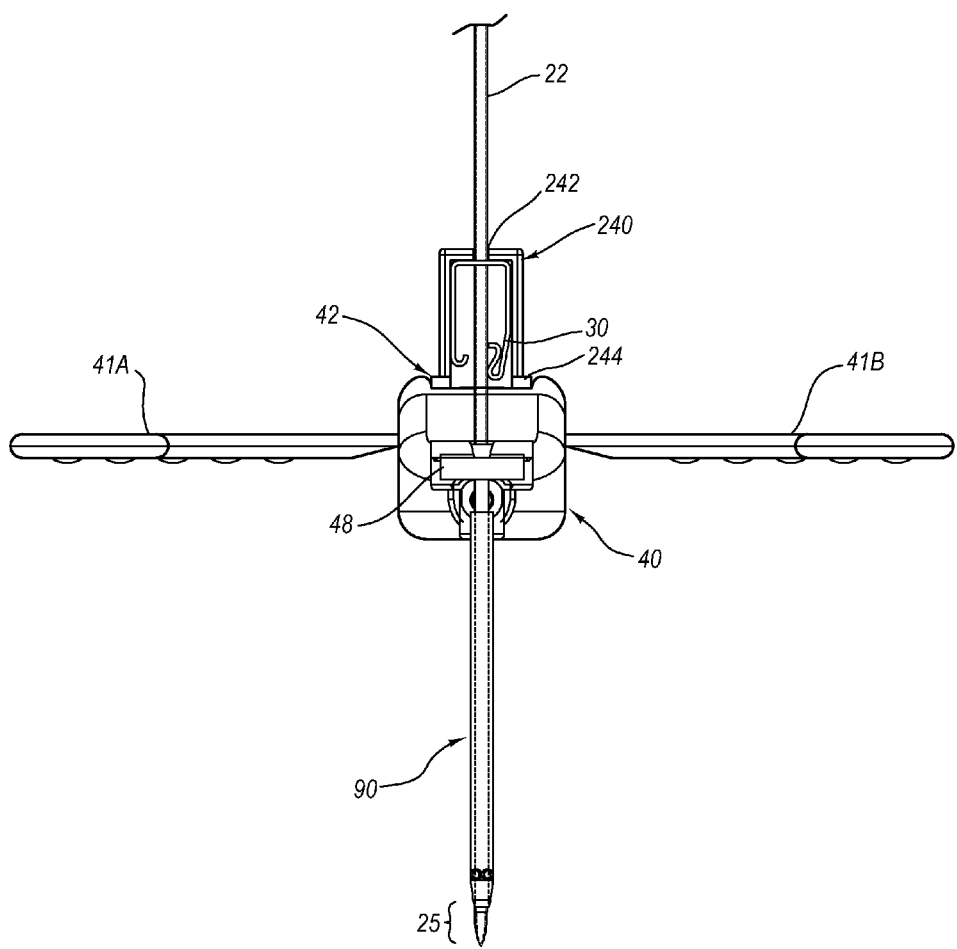
FIG. 22B is a cross-sectional side view of an exemplary safety clip housing in a second position.

FIGS. 22A-22B are cross-sectional side views of an exemplary safety clip housing 240. Safety clip housing 240 generally represents any structure configured to at least partially enclose a safety clip of any shape or size; including, for example, the various safety clip embodiments described and/or illustrated herein. In the exemplary embodiment illustrated in FIGS. 22A-22B, safety clip housing 240 may be configured to house a substantially rectangular safety clip 30. As illustrated in these figures, safety clip housing 240 may comprise a hole 242 sized for receiving a slender pointed element, such as slender pointed element 22. Safety clip housing 240 may also comprise a base member 244 sized to fit within a recess 42 defined in hub 40, as illustrated in FIG. 22B.

Figure 23A:
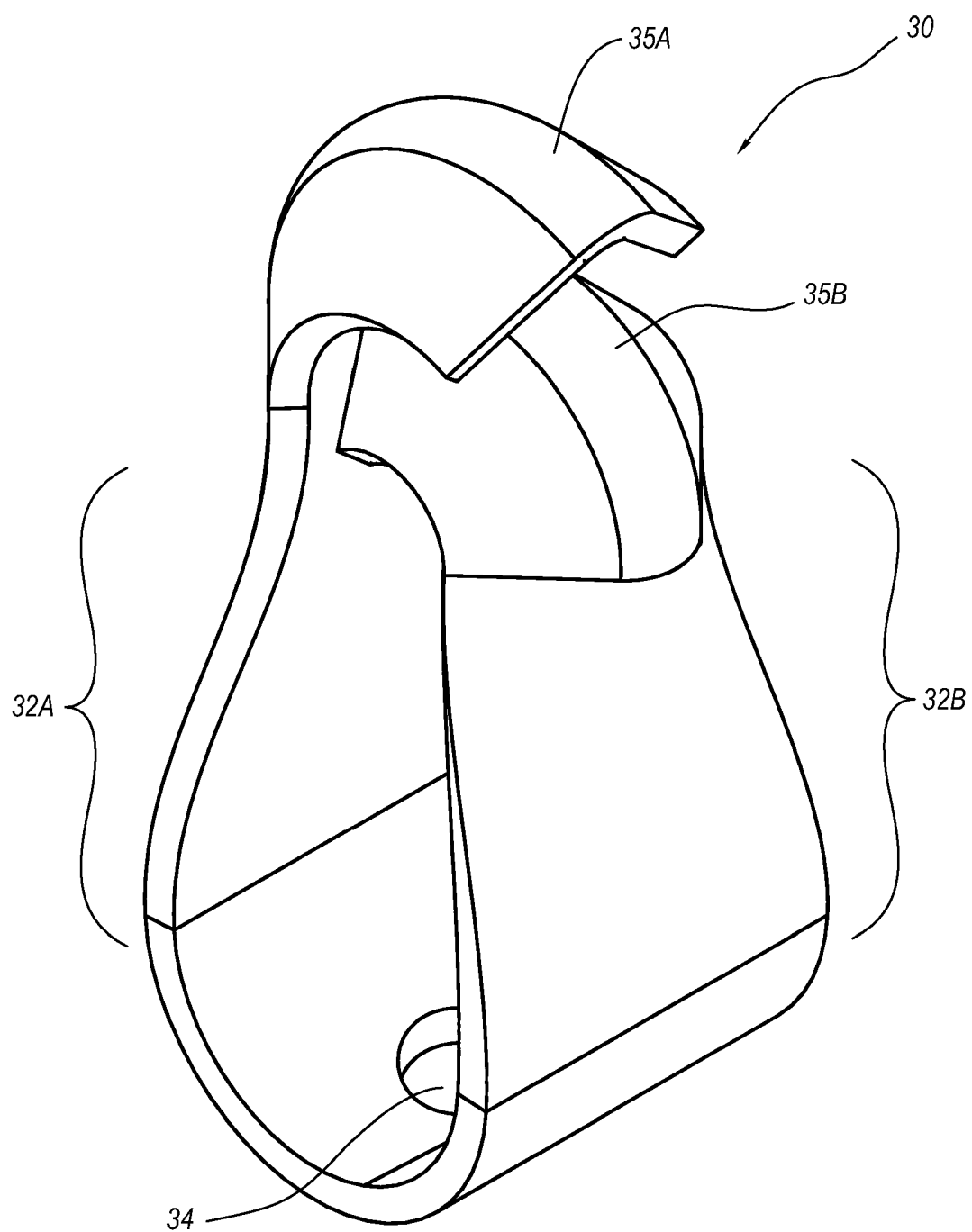
FIG. 23A is a perspective view of an additional embodiment of a safety clip in a first position.
Figure 23B:
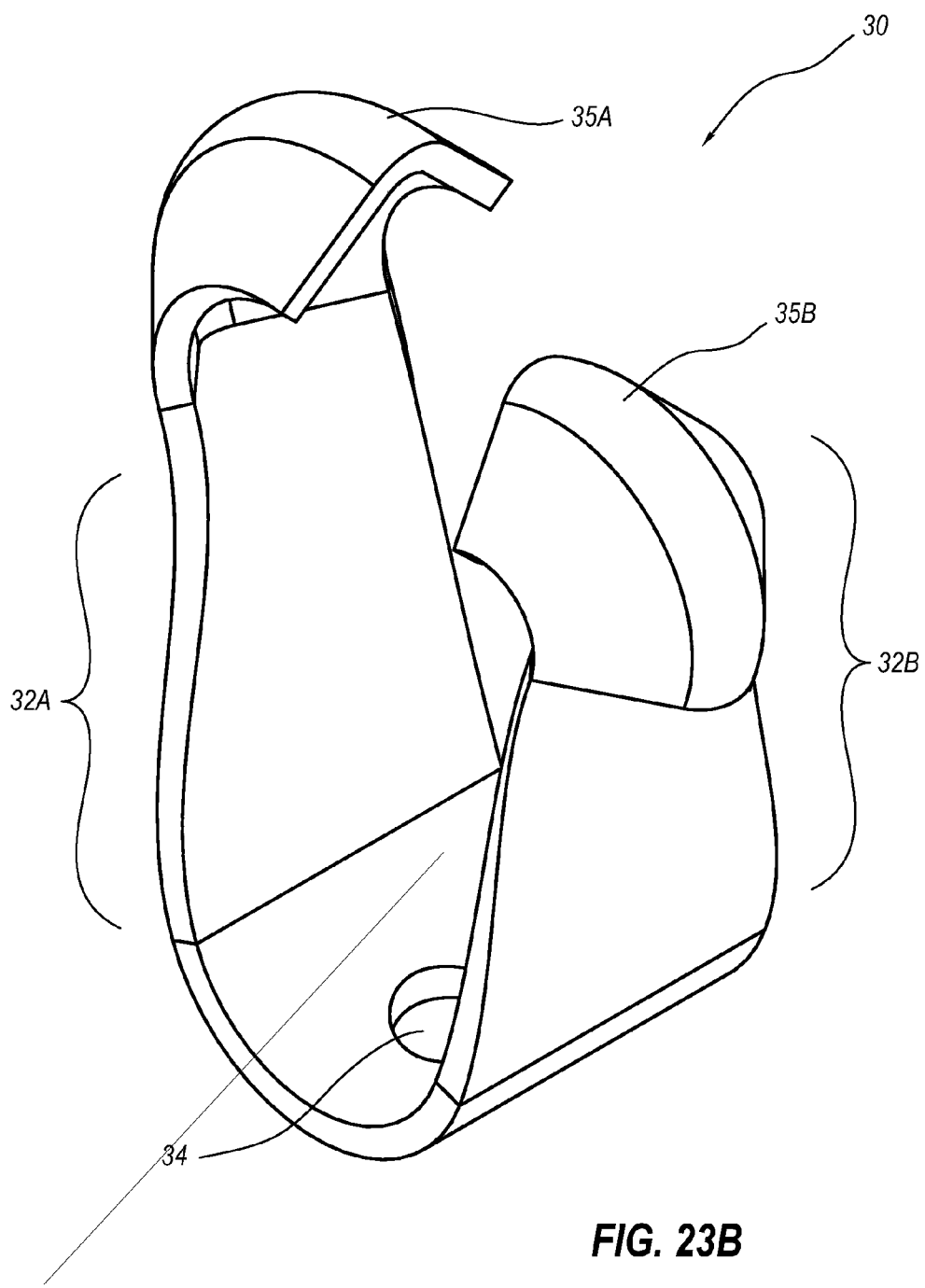
FIG. 23B is a perspective view of an additional embodiment of a safety clip in a second position.

FIGS. 23A and 23B are perspective views of an additional embodiment of a safety clip 30. Safety clip 30 generally represents any self-actuating device for capturing a pointed end of a slender pointed element, such as pointed end 25 of slender pointed element 22 illustrated in FIG. 3A. In the exemplary embodiment illustrated in FIG. 23A, safety clip 30 may comprise a plurality of legs 32A and 32B having curved end regions 35A and 35B, respectively, and a hole 34 sized for receiving a slender pointed element, such as slender pointed element 22. In at least one embodiment, safety clip 30 may be sized to fit within a recess defined in an insertion assembly, such as recess 24 defined in insertion assembly 20 illustrated in FIG. 3B. Safety clip 30 may also be sized to fit within a recess defined in a hub of an infusion system, such as recess 42 of hub 40, or sized to fit within a safety clip housing, such as safety clip housing 240.

In at least one embodiment, safety clip 30 is attached to slender pointed element 22 by passing the pointed end 25 of slender pointed element 22 through hole 34 of safety clip 30, past legs 32A and 32B, and past curved end regions 35A and 35B. Once pointed end 25 of slender pointed element 22 has passed curved end regions 35A and 35B, legs 32A and 32B may clamp around slender pointed element 22 to removably affix the safety clip to slender pointed element 22. As slender pointed element 22, together with safety clip 30, is inserted into recess 42 defined in hub body 50, slender pointed element 22 may continue through safety clip 30 and into a sealable path defined in a hub body, such as hub body 50. In addition, legs 32A and 32B of safety clip 30 may be biased such that, upon removal of slender pointed element 22 from the sealable path defined in hub body 50, curved end regions 35A and 35B may close around the pointed end 25 of slender pointed element 22 to retain the pointed end 25 within the body of safety clip 30. Such a safety clip 30 may prevent inadvertent insertion of slender pointed element 22 into another person, such as a medical practitioner utilizing infusion system 10.

FIGS. 24A-24D are perspective and cross-sectional side views of an additional embodiment of a safety clip 30. As seen in these figures, safety clip 30 may comprise a hole 34 sized for receiving a slender pointed element (such as slender pointed element 22), a first leg 32A comprising an upper arm portion 35A and a lower arm portion 39A, and a second leg 32B comprising an upper arm portion 35B and a lower arm portion 39B. In at least one embodiment, safety clip 30 may be sized to fit within a recess defined in an insertion assembly, such as recess 24 defined in insertion assembly 20 illustrated in FIG. 3B. Safety clip 30 may also be sized to fit within a recess defined in a hub of an infusion system, such as recess 42 of hub 40, or sized to fit within a safety clip housing, such as safety clip housing 240.

In at least one embodiment, upper arm portions 35A and 35B and lower arm portions 39A and 39B of safety clip 30 may be configured to retain the pointed end 25 of slender pointed element 22 within the body of safety clip 30. For example, legs 32A and 32B of safety clip 30 may be biased such that, upon removal of slender pointed element 22 from hub body 50, lower arm portions 39A and 39B may close around the pointed end 25 of slender pointed element 22 to retain the pointed end 25 within the body of safety clip 30. In addition, upper arm portions 35A and 35B may be configured to prevent a protrusion 45 provided on slender pointed element 22 from passing upwards through hole 34. Similarly, lower arm portions 39A and 39B may be configured to allow the protrusion 45 provided on slender element 22 to enter the body of safety clip 30, but to prevent the protrusion 45 from passing downwards past lower arm portions 39A and 39B. Such a safety clip 30 may prevent inadvertent insertion of slender pointed element 22 into another person, such as a medical practitioner utilizing infusion system 10.

Figure 25A:
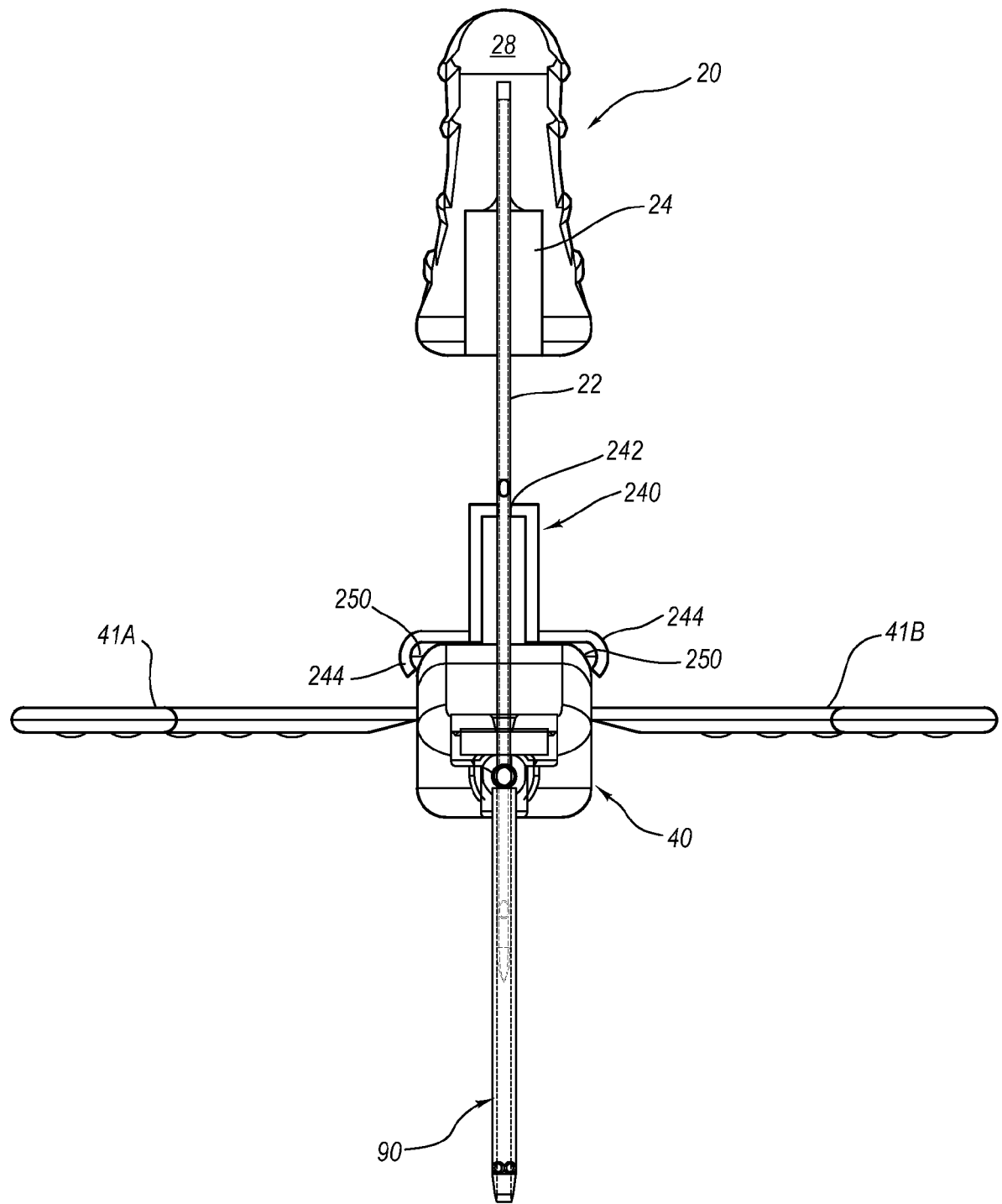
FIG. 25A is a cross-sectional side view of an exemplary safety clip housing removably attached to a hub.
Figure 25B:
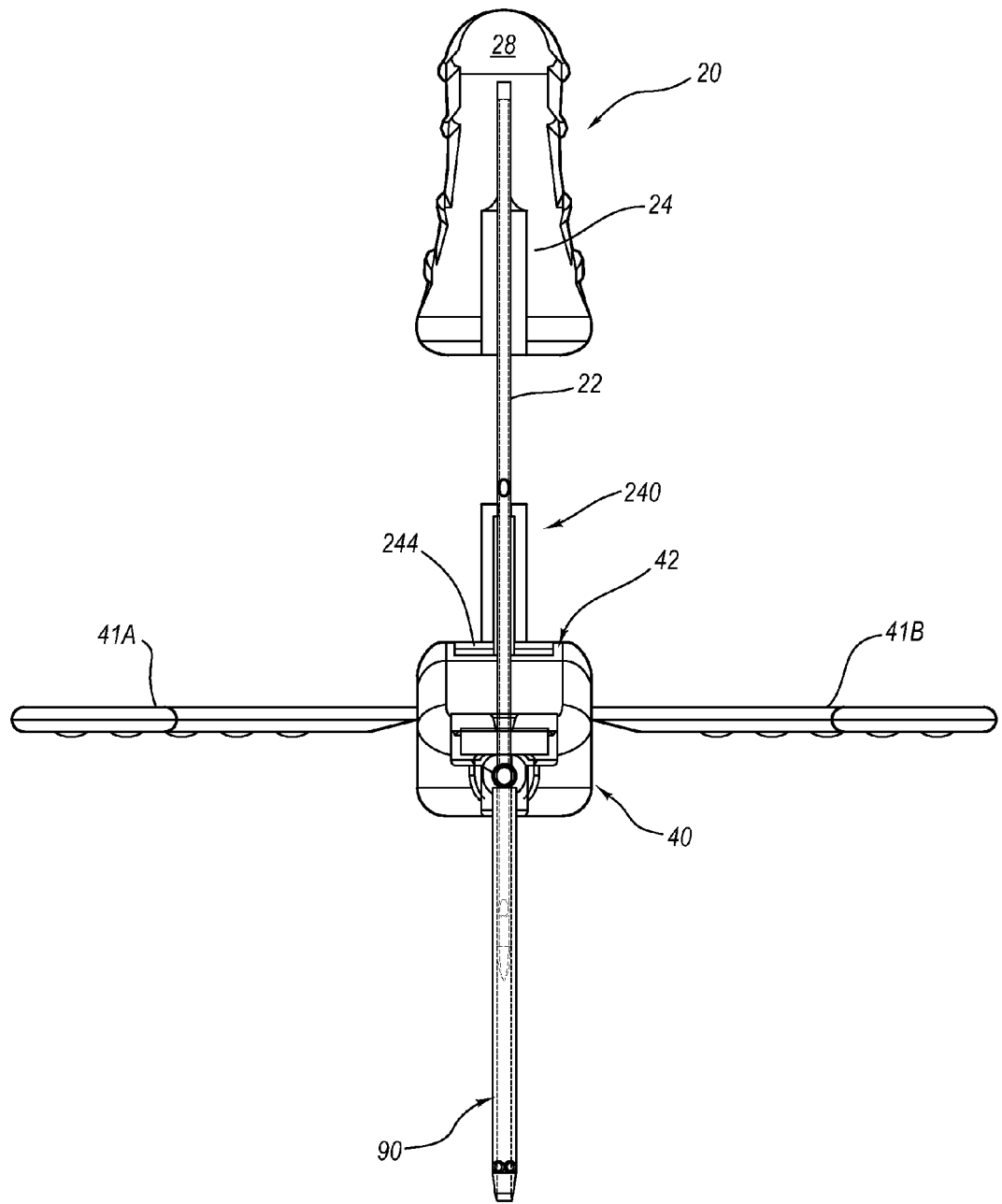
FIG. 25B is a cross-sectional side view of an exemplary safety clip housing adhered to a hub.

As detailed above, one or more of the exemplary safety clip embodiments described and/or illustrated herein may be sized so as to fit within a safety clip housing, such as safety clip housing 240 illustrated in FIGS. 22A-22B. As will be appreciated by those of skill in the art, such a safety clip housing may be attached or affixed to a slender pointed element, to a hub, or both, in any number of ways. For example, as illustrated in the schematic cross-sectional side view of FIG. 25A, a safety clip housing 240 may be configured to be removably attachable to a portion of a hub 40. More specifically, safety clip housing 240 may comprise a base member 244 configured to snap-fit over a plurality of complimentary protrusions 250 provided on hub 40. Optionally, as illustrated in FIG. 25B, base member 244 of safety clip housing 240 may be positioned and permanently adhered within a recess 42 provided in hub 40.

Figure 26A:
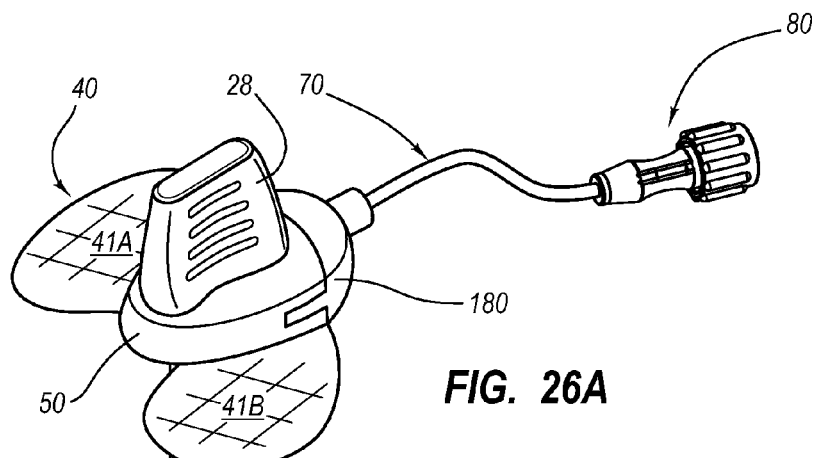
FIGS. 26A-26C are perspective views of an infusion system according to an additional embodiment.
Figure 26B:
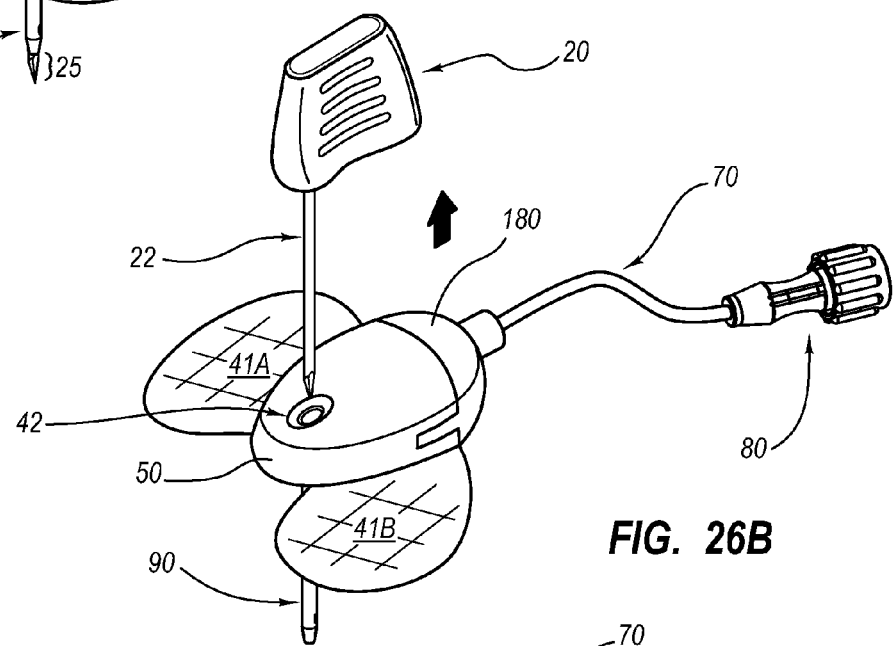
Figure 26C:
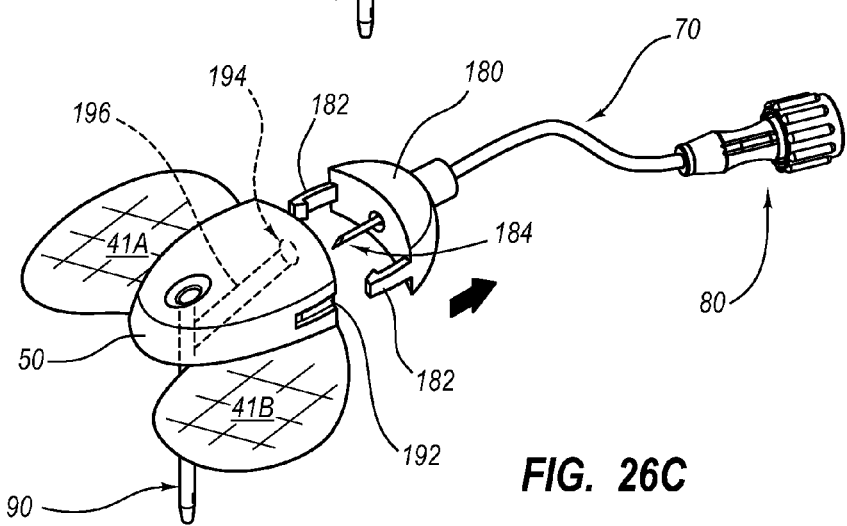

FIGS. 26A-26C are perspective views of an additional embodiment of an infusion system comprising an insertion assembly 20, a hub 40, a flexible catheter 90, an extension tube 70, and a tube connector 80. In at least one embodiment, a removable member 180 in fluid communication with extension tube 70 may be configured to be removably attachable to a hub body 50 of hub 40. For example, hub body 50 may comprise one or more coupling recesses 192 configured to receive complimentary coupling structures 182 provided on removable member 180. Accordingly, removable member 180 may be coupled to hub body 50 by positioning coupling structures 182 within complimentary coupling recesses 192. In certain embodiments, removable member 180 may also comprise a pointed tubular element 184 in fluid communication with extension tube 70. Generally speaking, pointed tubular element 184 may be configured to penetrate a penetrable septum 194 provided within hub body 50. In at least one embodiment, penetrable septum 194 seals a tubing portion 196 in fluid connection with flexible catheter 90. Thus, a fluid communication path between flexible catheter 90 and extension tube 70 may be established by inserting tubular element 184 through septum 194 and into tubing portion 196 housed in hub body 50.

Figure 27A:
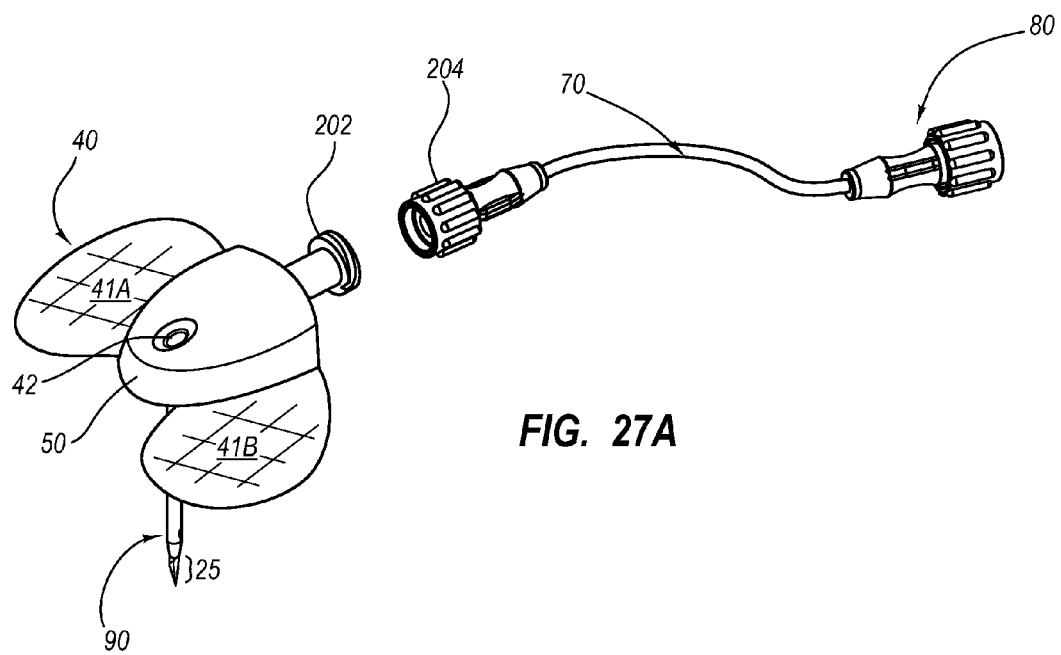
FIGS. 27A and 27B are perspective views of additional embodiments of an infusion system.
Figure 27B:
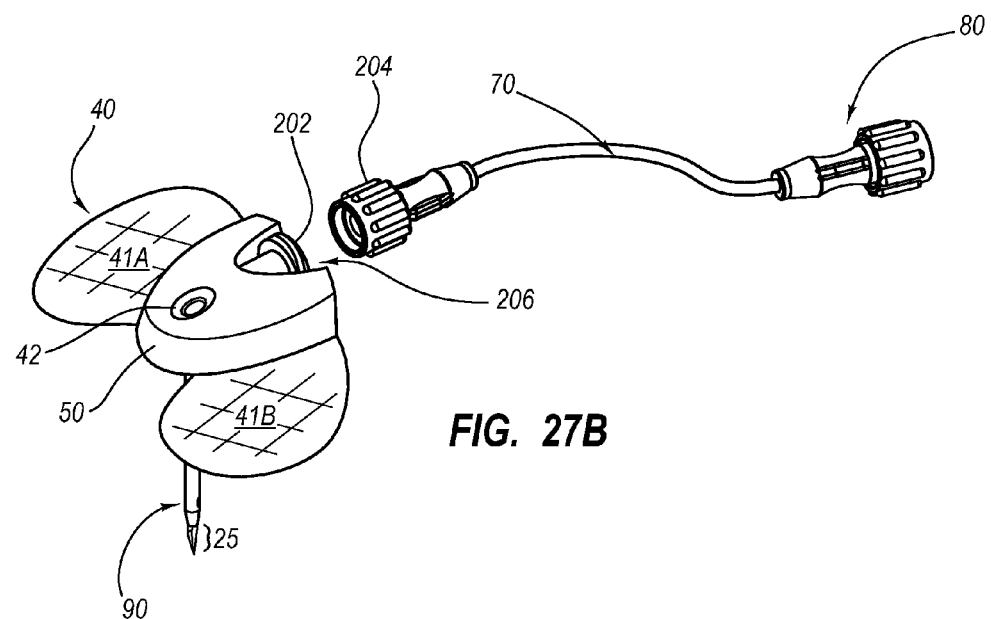

Persons of ordinary skill in the art will appreciate that extension tube 70 may be removably attached to hub 40 and/or flexible catheter 90 in any number of ways. For example, as illustrated in FIG. 27A, extension tube 70 may be removably attached to the hub body 50 of hub 40 by positioning a male tube connector 202 provided on hub body 50 within a complimentary female tube connector 204 attached to extension tube 70. Generally speaking, complimentary tube connectors 202 and 204 represent any form of tubing connection or mechanism known to those of skill in the art; including, for example, a so-called Luer-type fitting or connector. In an additional embodiment, male tube connector 202 may be positioned within a recess 206 defined within hub body 50 of hub 40, as illustrated in FIG. 27B.

Figure 28A:
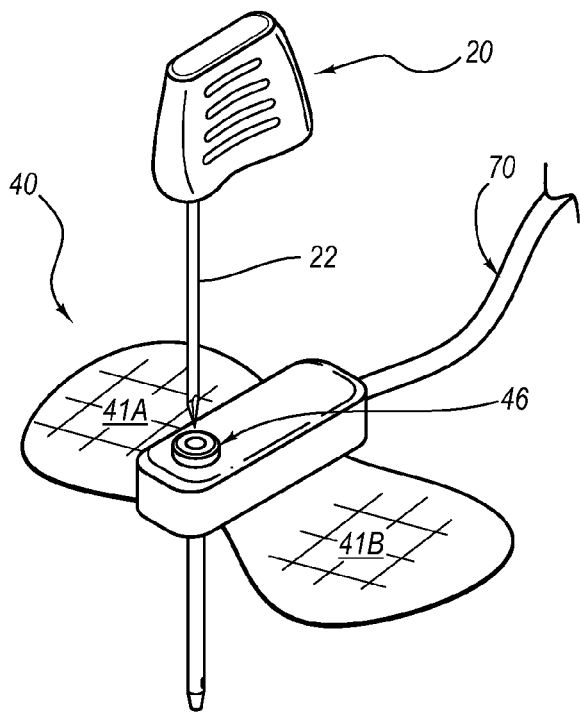
FIG. 28A is a perspective view of an infusion system according to an additional embodiment.
Figure 28B:
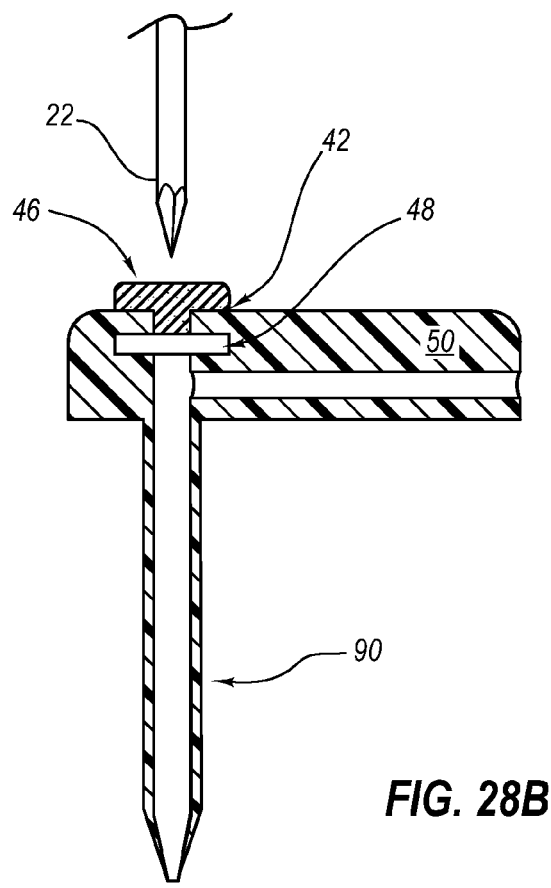
FIG. 28B is a cross-sectional side view of the exemplary infusion system illustrated in FIG. 28A.
Figure 32A:
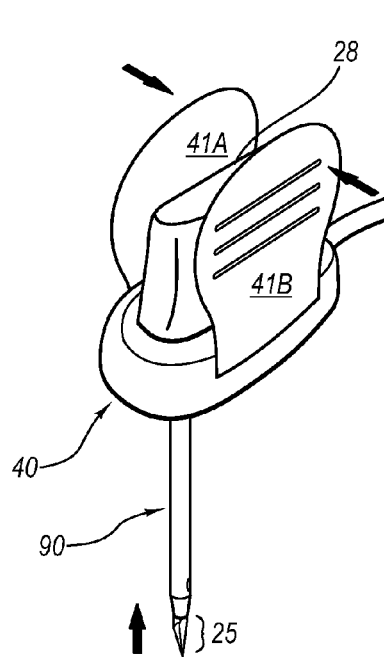
FIGS. 32A-32B are perspective views of an infusion system according to an additional embodiment.
Figure 32B:
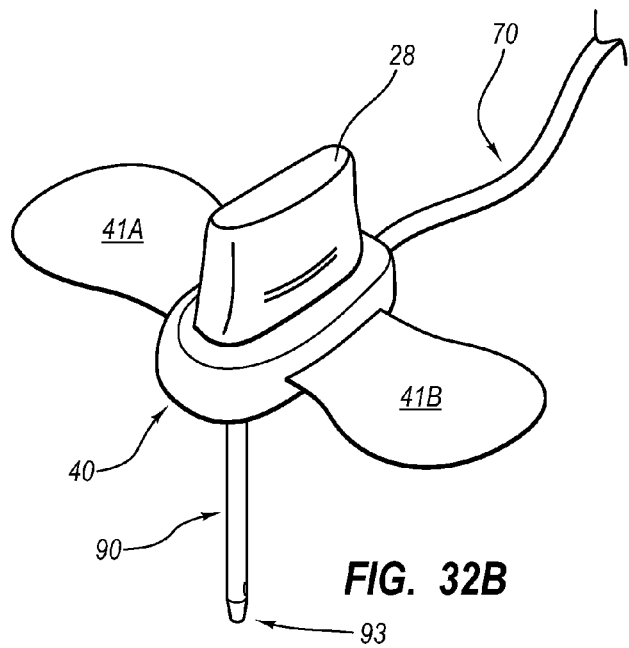
Figures 32C, 32D:
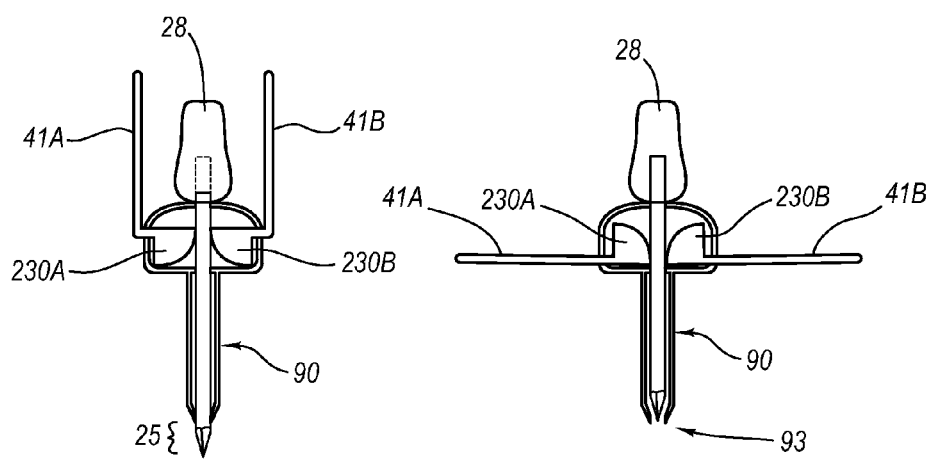
FIGS. 32C-32D are cross-sectional side views of the exemplary infusion system illustrated in FIGS. 32A-32B.

FIGS. 28A and 28B are perspective and cross-sectional views, respectively, of an infusion system according to an additional embodiment. As seen in these figures, this exemplary infusion system may comprise an insertion assembly 20, a base member 40, a flexible catheter 90, and an extension tube 70. In at least one embodiment, a cap element 46 may be inserted within a recess 42 defined in hub body 50. Cap element 46 generally represents any structure or device capable of sealing any aperture or recess defined within any of the components of the exemplary embodiments described and/or illustrated herein. In certain embodiments, cap element 46 may be positioned above septum 48 and configured to seal recess 42 from the environment, thereby preventing bacteria from entering and forming within recess 42. In an additional embodiment, a cap element 46 is disposed within each exposed recess and/or aperture defined in each component of exemplary infusion apparatus 10. Cap element 46 may be formed of any suitable material capable of sealing an aperture or recess; including, for example, medical-grade polymers (such as silicone) and monomers (such as Ethylene Propylene Diene Monomer ("EPDM"), or other suitable materials.

FIG. 29 illustrates an exemplary slender pointed element 22 comprising a pointed end 25. As illustrated in this figure, the pointed end 25 of slender pointed element 22 may be scored or otherwise weakened along line 23. Accordingly, upon completion of an infusion operation, the pointed end 25 of slender pointed element 22 may break off along line 23 upon removal of slender pointed element 22 from hub body 50, leaving the broken pointed end 25 of slender pointed element 22 within septum 48.

In at least one embodiment of infusion system 10, at least a portion of slender pointed element 22 may be retractable into a recess defined in insertion assembly 20. For example, as illustrated in FIGS. 30A-30B, a lever 200 coupled to slender pointed element 22 may be provided in a recess 29 defined in base member 28 of insertion assembly 20. In certain embodiments, lever 200 may be manipulated from a first position illustrated in FIG. 30A to a second position illustrated in FIG. 30B to retract at least a portion of slender pointed element 22 within base member 28. After pointed end 25 of slender pointed element 22 has been retracted past a second opening 93 of flexible catheter 90, a blood draw may be attempted to ensure the proper placement of flexible catheter 90 within the implanted device.

Similarly, as illustrated in FIGS. 31A-31D, a slender pointed element (such as slender pointed element 22 in FIG. 3A) may be retracted into base member 28 by depressing opposing buttons 210 and 214 provided on base member 28. In this exemplary embodiment, buttons 210 and 214 may comprise cantilevered end portions 212 and 216, respectively, that are configured to manipulate a complimentary cantilevered end portion 220 of slender pointed element 22 generally upwards within a recess defined in base member 28. In an additional embodiment, as illustrated in FIGS. 32A-32D, slender pointed element 22 may be retracted into base member 28 by manipulating wing structures 41A and 41B from a first position, illustrated in FIGS. 32A and 32C, into a second position, illustrated in FIGS. 32B and 32D. More particularly, wing structures 41A and 41B may comprise cantilevered end portions 230A and 230B, respectively, that are configured to manipulate slender pointed element 22 generally upwards within a recess defined in base member 28.

Figure 33A:
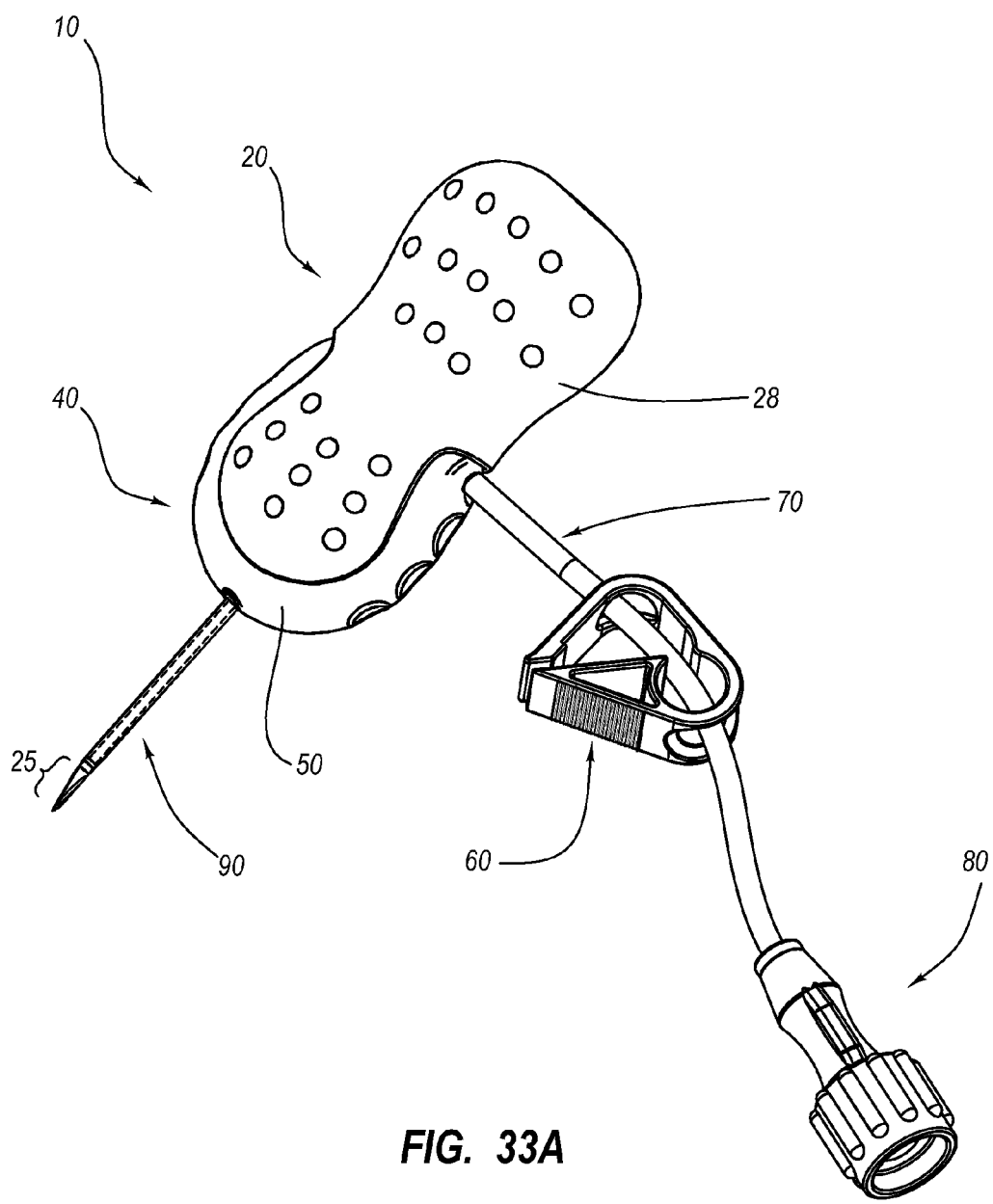
FIGS. 33A-33C are perspective views of an insertion assembly according to an additional embodiment.
Figure 33B:
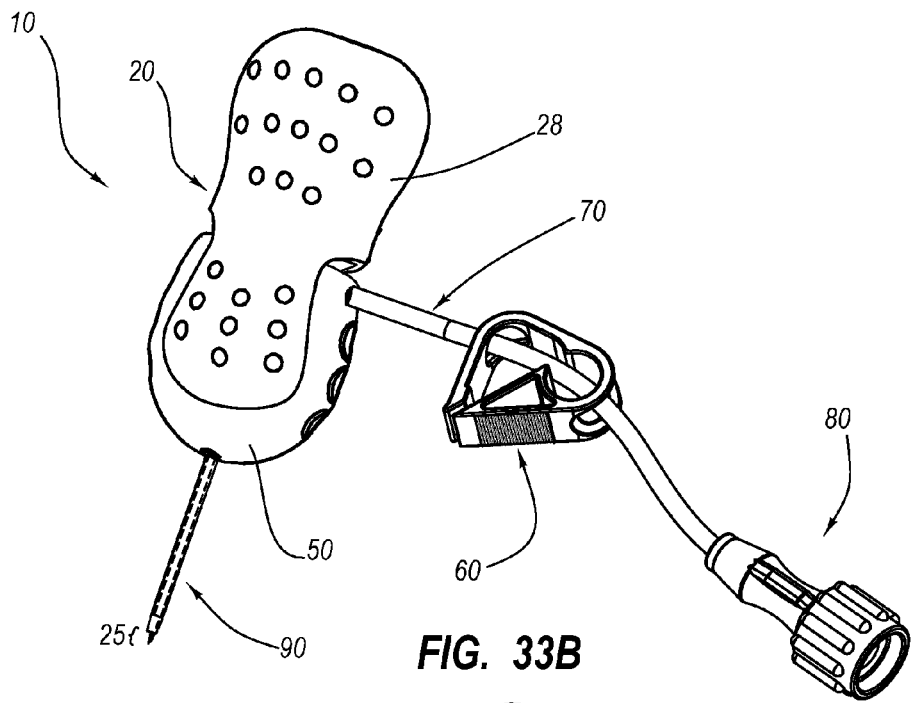
Figure 33C:
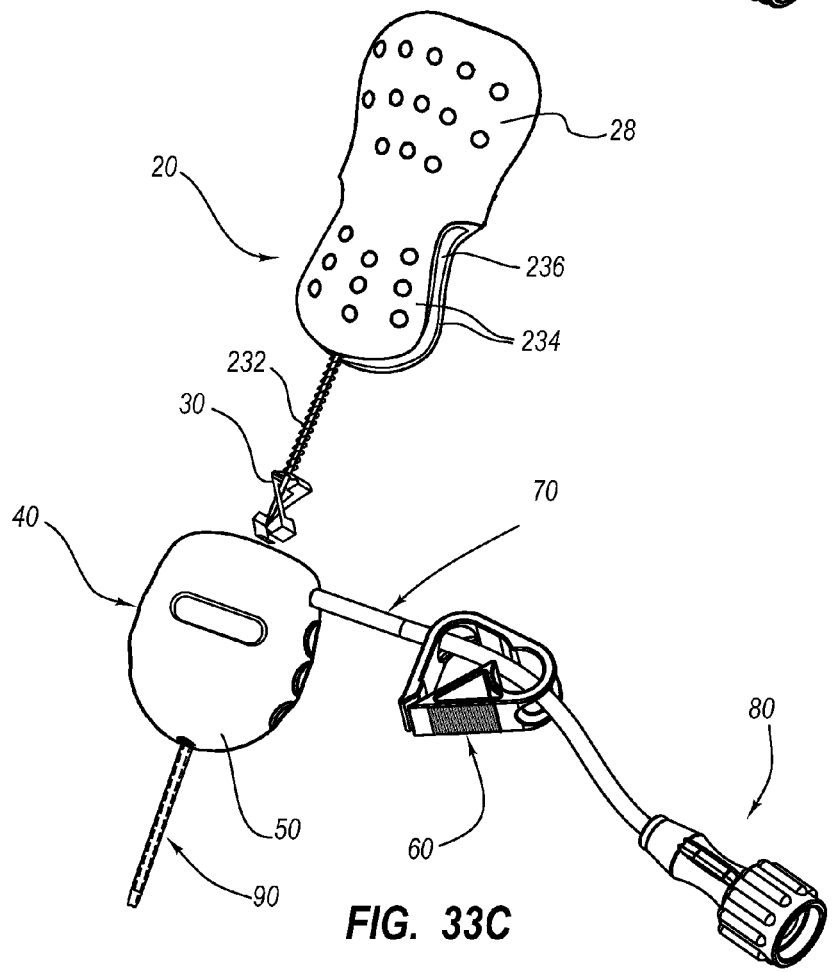

FIGS. 33A-33C are perspective views of an additional embodiment of an infusion apparatus 10. As seen in these figures, infusion apparatus 10 may comprise an insertion assembly 20, a hub 40, a flexible catheter 90, an extension tube 70, a clamp 60, and a tube connector 80. Insertion assembly 20 may comprise a biasing member 232 positioned around a slender pointed element 22 and positioned proximate a safety clip 30. In at least one embodiment, biasing member 232 may bias safety clip 30 away from insertion assembly 20 such that, upon removal of insertion assembly 20 from hub 40, safety clip 30 may positioned around a pointed end 25 of slender pointed element 22 by biasing member 232.

As best seen in FIG. 33C, insertion assembly 20 may also comprise a plurality of coupling arms 234 that define a recess 236 that is configured to receive at least a portion of hub 40. For example, hub 40 may be sized and shaped so as to fit within the recess 236 defined within insertion assembly 20 by coupling arms 234. In at least one embodiment, the exemplary configuration of infusion system 10 in FIGS. 33A-33C may provide various advantages, such as ease of handling by a user and/or compatibility with additional structures.

Figure 34A:
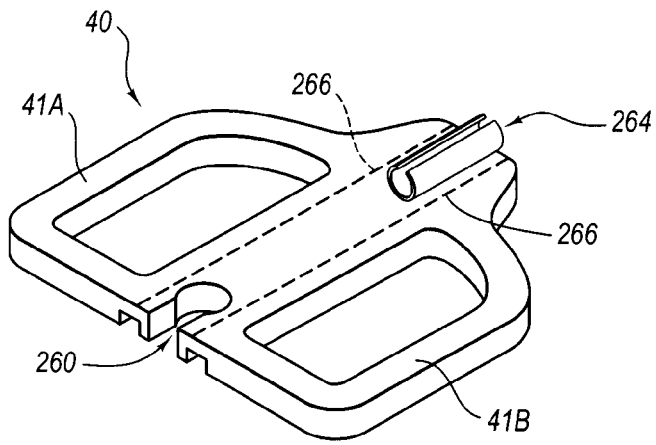
FIGS. 34A-34C are perspective views of an exemplary hub for an infusion system according to an additional embodiment.
Figure 34B:
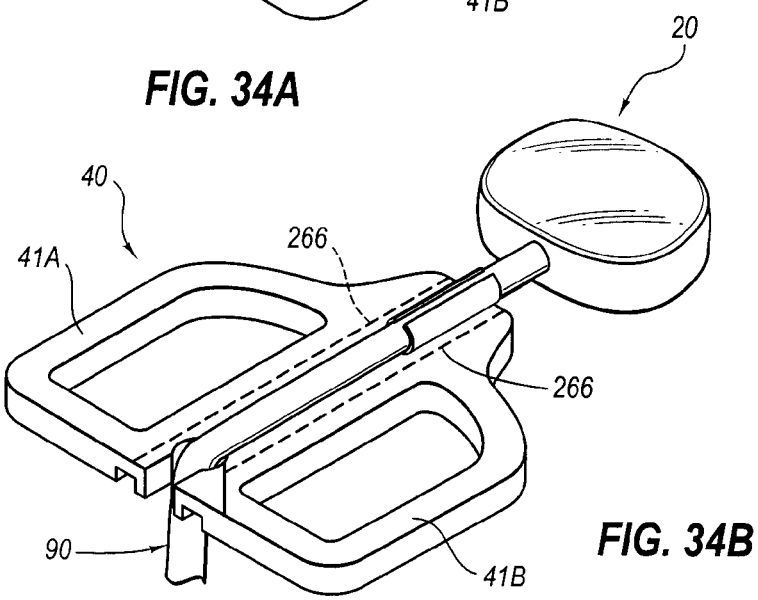
Figure 34C:
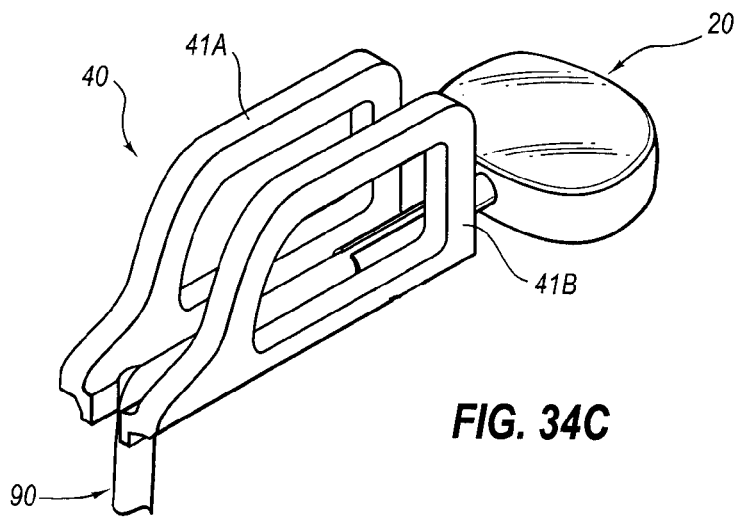

FIGS. 34A-34C are perspective views of an exemplary hub 40 for an infusion system according to an additional embodiment. As seen in these figures, exemplary hub 40 may comprise a plurality of wing structures 41A and 41B. In at least one embodiment, wing structures 41A and 41B are configured to affix exemplary hub 40 to the skin of a patient. For example, wing structures 41A and 41B may be taped, adhesively affixed, or otherwise attached to the surface of a patient's skin, such as skin surface 310 in FIG. 1. In additional embodiment, a sheet of material, such as TEGADERM®, may be used to affix hub 40 to the surface of a patient's skin.

As seen in FIG. 34A, hub 40 may comprise a recess 260 and a receiving enclosure 264. In at least one embodiment, recess 260 is sized and configured to receive at least a portion of a flexible catheter, such as flexible catheter 90 in FIGS. 34B-34C. Similarly, receiving enclosure 264 may be sized and configured to retain at least a portion of a flexible catheter, such as flexible catheter 90 in FIGS. 34B-34C. In certain embodiments, wing structures 41A and 41B of hub 40 may be configured to fold inwardly along a folding line 266. As best seen in FIGS. 34B and 34C, after positioning at least a portion flexible catheter 90 within recess 260 and receiving enclosure 264, wing structures 41A and 41B may be folded inwardly upward. In one embodiment, wing structures 41A and 41B may be affixed to a patient's skin when in a downward, extended position, illustrated in FIG. 34B. In addition, flexible catheter 90 and/or a slender pointed element, such as slender pointed element 22 in FIG. 3A, may be removed from hub 40 when wing structures 41A and 41B are in an upward, folded position, illustrated in FIG. 34C.

As detailed above, one or more of the exemplary embodiments described and/or illustrated herein may be employed in accessing a device, such as exemplary access port 320, implanted within a patient. In at least one embodiment, a method of accessing an implanted device using a infusion system may comprise: 1) positioning at least a portion of slender pointed element 22 within flexible catheter 90; 2) penetrating a septum of an implanted device, such as septum 326 of access port 320, using the slender pointed element 22 positioned within the flexible catheter 90; and 3) positioning at least a portion of flexible catheter 90 within the implanted device. For example, a clinician may grasp base member 28 of insertion assembly 20 and may guide the pointed end 25 of slender pointed element 22 into recess 42 of hub 40, through septum 48, and into flexible catheter 90. The clinician may then guide the pointed end 25 of slender pointed element 22 (positioned within flexible catheter 90) through the skin surface 310 and subcutaneous zone 312 of a patient and into a port septum 326. The clinician may then confirm that flexible catheter 90 is positioned within chamber 324 of access port 320 by drawing blood through extension tube 70 using a syringe attached to tube connector 80. Thus, blood may be drawn through apertures 92 of flexible catheter 90 and through at least one cavity formed between an inner surface of flexible catheter 90 and an outer surface of slender pointed element 22. Blood may then travel through hub 40 (i.e., manifold element 61) and through extension tube 70 to confirm that slender pointed element 22 and flexible catheter 90 of infusion system 10 are properly placed within port chamber 324.

Subsequent to confirmation of proper placement of slender pointed element 22 and flexible catheter 90, base member 28 of insertion assembly 20 may be grasped and slender pointed element 22 may be removed from hub 40, while flexible catheter 90 may remain positioned within chamber 324 of access port 320. Septum 48 may seal any hole or aperture created by the removal of slender pointed element 22. Upon removal of slender pointed element 22, flexible catheter 90 may be positioned or oriented in any number of ways; including for example, by positioning flexible catheter 90 substantially perpendicularly to skin surface 310. Safety clip 30 may remain attached to hub 40 (i.e., within recess 42) until the pointed tip 25 of slender pointed element 22 becomes encased by safety clip 30 (via movement of legs 32A and 32B), after which time safety clip 30 may be removed from recess 42 of hub 40. Hub 40, extension tube 70, tube connector 80, or combinations thereof may then be taped to skin surface 310 of the patient. Optionally, wing structures 41A and 41B may be adhesively affixed to skin surface 310.

Accordingly, each of the exemplary infusion system embodiments described and/or illustrated herein may provide vascular access (via an implanted device) for any number of procedures; including, for example, infusion, blood aspiration, hemodialysis, hemofiltration, peritoneal dialysis, or other procedures as known in the art. Advantageously, the use of sharp implements may be reduced or eliminated, thereby reducing the danger of inadvertent sticks or punctures.

The preceding description has been provided to enable others skilled in the art to best utilize various aspects of the exemplary embodiments described herein. This exemplary description is not intended to be exhaustive or to be limited to any precise form disclosed. Many modifications and variations are possible without departing from the spirit and scope of the instant disclosure. For example, each component in each exemplary embodiment described and/or illustrated herein may be formed in any number of suitable shapes, sizes, and configurations. In addition, the various infusion system embodiments described herein may be adapted for use in connection with high pressure operations, commonly referred to as "power injection" processes. Accordingly, the various components of the exemplary embodiments provided herein may be adapted to handle pressure of about 400 psi or higher.

The embodiments described and/or illustrated herein are in all respects illustrative and not restrictive. Accordingly, reference should be made to the appended claims and their equivalents for determining the scope of the instant disclosure. For ease of use, the words "including" and "having," as used in the specification and claims, are interchangeable with and have the same meaning as the word "comprising."

What is claimed is:

1. An infusion apparatus for providing access to an implanted device, comprising:
   an insertion assembly;
   a hub including a body comprising a sealable path extending from a first opening in a first end of the body to a second opening in a second end of the body, a septum disposed in the sealable path and compressed in the hub body;
   a unitary manifold element positioned in the hub body, a first portion of the manifold element positioned in the sealable path retaining the septum and preventing movement of the septum along the sealable path toward the second opening;
   a flexible catheter having a proximal end inserted into the second opening and attached to the hub;
   an extension tube in fluid communication with the hub through a third opening, a passageway formed in the hub body between the third opening and the sealable path, the manifold element having a second portion positioned in the passageway fluidly connecting the extension tube to the flexible catheter; and
   a cap element in the sealable path at an end of the manifold element first portion, the cap element preventing movement of the septum in a direction toward the first opening.

2. The infusion apparatus of claim 1, wherein the hub further comprises a plurality of wing structures.

3. The infusion apparatus of claim 1, wherein the insertion assembly comprises a slender pointed element and both the sealable path and the flexible catheter are configured to receive at least a portion of the slender pointed element.

4. The infusion apparatus of claim 3, wherein the extension tube is connected to a removable member, the removable member including a needle insertable through the third opening and a coupling structure mating with a recess in the hub body.

5. The infusion apparatus of claim 3, wherein the flexible catheter comprises at least one aperture defined proximate a distal end of the flexible catheter and the slender pointed element comprises at least one longitudinally extending indentation defined along the slender pointed element.

6. The infusion apparatus of claim 5, wherein a cross-sectional area defined between an exterior surface of the slender pointed element and an interior surface of the flexible catheter approximates the cross-sectional area of a hollow needle gauge.

7. The infusion apparatus of claim 3, wherein:
the flexible catheter comprises at least one aperture defined proximate a distal end of the flexible catheter; and
the slender pointed element is at least partially hollow and comprises at least one aperture defined within the slender pointed element for communicating fluid with the at least one aperture defined in the flexible catheter.

8. The infusion apparatus of claim 3, wherein at least a portion of the slender pointed element is retractable into a recess defined in the insertion assembly.

9. The infusion apparatus of claim 3, further comprising a safety clip configured to retain a pointed end of the slender pointed element within the safety clip when the slender pointed element is removed from the hub and to allow the pointed end of the slender pointed element to pass through the safety clip when the slender pointed element is inserted into the hub.

10. The infusion apparatus of claim 1, wherein the flexible catheter has a length that exceeds an anticipated insertion length such that, when the flexible catheter is fully inserted into a device implanted within a patient, a bendable portion of the flexible catheter extends from a skin surface of the patient.

11. The infusion apparatus of claim 10, further comprising a pad member including a receiving enclosure configured to retain at least a portion of the hub.

12. The infusion apparatus of claim 1, further comprising a reinforcing member at least partially imbedded within the flexible catheter.

13. The infusion apparatus of claim 1, wherein the extension tube is removably attached to the hub.

14. A hub for an infusion set, comprising:
a hub body including a first path extending along a first longitudinal axis from a first opening in a first end of the body to a second opening in a second opposite end of the body, and a second path extending along a second longitudinal axis generally perpendicular to the first longitudinal axis from a third opening to the first path;
a unitary manifold element positioned in the hub body extending into the first path and the second path, the manifold element defining a plenum in fluid communication with the first, second, and third openings;
a flexible catheter having a proximal end inserted through the second opening and positioned at least partially in the manifold element, an outer surface of the flexible catheter attached to an inner surface of the manifold element;
an extension tube having a distal end inserted through the third opening of the hub body, the manifold element providing fluid communication between the extension tube and the flexible catheter; and
a compressed septum positioned in the first path and retained between the unitary manifold element and a securement cap, the securement cap including an aperture in fluid communication with the first path.

15. The hub according to claim 14, wherein a distal end of the extension tube is positioned at least partially in the manifold element, an outer surface of the extension tube attached to an inner surface of the manifold element.

16. An infusion set, comprising:
the hub according to claim 14; and
an infusion assembly including a slender pointed element, the distal end of the slender pointed element extending beyond a distal end of the flexible catheter when the infusion assembly is coupled to the hub for insertion into an implanted port.

* * * * *